United States Patent [19]

Navia et al.

[11] Patent Number: 5,849,296
[45] Date of Patent: *Dec. 15, 1998

[54] CROSSLINKED PROTEIN CRYSTALS

[75] Inventors: Manuel A. Navia, Lexington; Nancy L. St. Clair, Charlestown, both of Mass.

[73] Assignee: Vertex Pharmaceuticals, Inc., Cambridge, Mass.

[*] Notice: The term of this patent shall not extend beyond the expiration date of Pat. No. 5,618,710.

[21] Appl. No.: 476,267

[22] Filed: Jun. 7, 1995

Related U.S. Application Data

[63] Continuation of Ser. No. 17,510, Feb. 12, 1993, Pat. No. 5,618,710, which is a continuation-in-part of Ser. No. 864,424, Apr. 6, 1992, abandoned, which is a continuation-in-part of Ser. No. 720,237, Jun. 24, 1991, abandoned, which is a continuation-in-part of Ser. No. 562,280, Aug. 3, 1990, abandoned.

[51] Int. Cl.$^6$ .......................... A61K 39/395; C12N 1/00; C12P 1/00; C07K 17/00

[52] U.S. Cl. .................... 424/178.1; 424/159.1; 424/164.1; 424/179.1; 424/94.1; 424/94.6; 424/94.63; 435/41; 435/109; 435/195; 435/198; 435/212; 435/218; 435/817; 435/174; 436/518; 514/2; 530/402; 530/413; 530/810

[58] Field of Search .................... 435/174, 176, 435/177, 180, 8, 816, 41, 109, 195, 198, 212, 218, 817; 424/178.1, 159.1, 164.1, 179.1, 94.1, 94.6, 94.63; 436/518; 514/2; 530/402, 413, 810

[56] References Cited

U.S. PATENT DOCUMENTS

| Re. 33,441 | 11/1990 | Wumpelmann et al. | 435/94 |
|---|---|---|---|
| 4,390,632 | 6/1983 | Carter | 436/10 |
| 4,411,996 | 10/1983 | Lloyd | 435/94 |
| 4,693,985 | 9/1987 | Degen et al. | 436/531 |
| 4,699,882 | 10/1987 | Visuri | 435/188 |
| 4,892,825 | 1/1990 | Wumpelmann et al. | 435/94 |
| 5,120,650 | 6/1992 | Visuri | 435/176 |
| 5,618,710 | 4/1997 | Navia et al. | 435/174 |

FOREIGN PATENT DOCUMENTS

| 0 092 829 | 11/1983 | European Pat. Off. . |
|---|---|---|
| 0 166 427 | 1/1986 | European Pat. Off. . |
| 0 169 767 | 1/1986 | European Pat. Off. . |
| 0 175 582 | 3/1986 | European Pat. Off. . |
| 0 195 311 | 9/1986 | European Pat. Off. . |
| 0 341 503 | 11/1989 | European Pat. Off. . |
| 0 367 302 | 5/1990 | European Pat. Off. . |
| WO 85/03247 | 8/1985 | WIPO . |
| WO 91/05857 | 5/1991 | WIPO . |

OTHER PUBLICATIONS

G. M. Alter et al., "Kinetic Properties of Carboxypeptidase B in Solutions and Crystals", *Biochemistry*, 16, pp. 3663–3668 (1977).

S.A. Barker et al., "Enzymatic Processes for High–Fructose Corn Syrup," In: *Enzymes and Immobilized Cells in Biotechnology*, Menlo Park, CA (1985).

G.J. Bartling et al., "Protein Modification in Nonaqueous Media—A New Method of Enzyme Cross–Linking", *Enzyme*, 18, pp. 310–316 (1974).

S.J. Bayne et al., "Enzymatically Active, Cross–Linked Pig Heart Lactate Dehydrogenase Crystals", *Carlsberg Res. Comm.*, 41, pp. 211–216 (1976).

W.H. Bishop et al., "Isoelectric Point of a Protein in the Crosslinked Crystalline State: β–Lactoglobulin", *J. Mol. Biol.*, 33, pp. 415–421 (1968).

A. Dyer et al., "A Thermal Investigation of the Stability of Crystalline Cross–Linked Carboxypeptidase A", *Thermochimica Acta*, 8, pp. 455–464 (1974).

D.J. Haas, "Preliminary Studies on the Denaturation of Cross–Linked Lysozyme Crystals", *Biophys. J.*, 8, pp. 549–555 (1968).

H.C. Hedrich et al., "Large–Scale Purification, Enzymic Characterization, and Crystallization of the Lipase from *Geotrichum Candidum*", *Enzyme & Microb. Technol.*, 13, p. 840–847 (1991).

J.V. Hupkes, "Practical Process Conditions for the Use of Immobilized Glucose Isomerase," *Starch*, 30, pp. 24–28 (1978).

P.J. Kasvinsky et al., "Activity of Glycogen Phosphorylase in the Crystalline State", *J.Biol. Chem.*, 251, pp. 6852–6859 (1976).

H. Kirsten et al., "Catalytic Activity of Non–Cross–Linked Microcrystals of Aspartate Aminotransferase in Poly(ethylene glycol)", *Biochem. J.*, 211, pp. 427–434 (1983).

A.M. Klibanov, "Enzymatic Catalysis in Anhydrous Organic Solvents", *Trends in Biochem. Sci.*, 14, pp. 141–144 (1989).

G. Lindeberg, "A Convenient Synthesis of Aspartame", *J. Chem. Ed.*, 64, pp. 1062–1064 (1987).

D. Lombardo et al., "Crystallization and Preliminary X–ray Study of Horse Pancreatic Lipase", *J. Mol. Biol.*, 205, pp. 259–261 (1989).

(List continued on next page.)

Primary Examiner—David M. Naff
Attorney, Agent, or Firm—Fish & Neave; James F. Haley, Jr.; Margaret A. Pierri

[57] ABSTRACT

A protein such as an enzyme or antibody is immobilized by crosslinking crystals of the protein with a multifunctional crosslinking agent. The crosslinked protein crystals may be lyophilized for storage. A preferred protein is an enzyme such as thermolysin, elastase, asparaginase, lysozyme, lipase or urease. Crosslinked enzyme crystals preferably retain at least 91% activity after incubation for three hours in the presence of a concentration of Pronase™ that causes the soluble uncrosslinked form of the enzyme to lose at least 94% of its initial activity under the same conditions. A preferred enzyme:Pronase™ ratio is 1:40. Enzyme crystals that are crosslinked may be microcrystals having a cross-section of $10^{-1}$ mm or less. Crosslinked enzyme or antibody crystals may be used in an assay, diagnostic kit or biosensor for detecting an analyte, in an extracorporeal device for altering a component of a fluid, in producing a product such as using crosslinked thermolysin crystals to produce aspartame, in separating a substance from a mixture, and in therapy.

15 Claims, 19 Drawing Sheets

OTHER PUBLICATIONS

S. Luesner, "Applications of Microbial Enzymes To Produce High Fructose Corn Syrup and Other Corn Sweeteners" (publication date unknown).

T.H. Maugh, II, "A Renewed Interest in Immobilized Enzymes", *Science*, 223, pp. 474–476 (1984).

T. Nakagawa et al., "Development of Effective Cross–Linking Method for Bioactive Substance–Enzyme Immobilization Using Glutaraldehyde Oligomers", *Chem. Pharm. Bull.*, 37, pp. 2463–2466 (1989).

K. Polvinen et al., "Pilot–Scale Production and Properties of Lignin Peroxidases", In: Enzymes in Biomass Conversion, Am. Chem. Soc., Boston, MA, Apr. 22–27 (1990).

F.A. Quiocho et al., "Intermolecular Cross Linking of a Protein in the Crystalline State: Carboxypeptidase–A", *Proc. Nat. Acad. Sci.*, 52, pp. 833–839 (1964).

F. A. Quiocho et al., "Effects of Changes in Some Solvent Parameters on Carboxypeptidase A in Solution and in Cross–Linked Crystals", *Proc. Nat. Acad. Sci.*, 57, pp. 525–537 (1967).

D.M. Shotton et al., "Conformational Changes and Inhibitor Binding at the Active Site of Elastase", *Cold Spring Harbour Symp Quant. Bio.*, XXXVI, pp. 91–105 (1972).

C.A. Spilburg et al., "Kinetic Properties of Crystalline Enzymes. Carboxypeptidase A", *Biochemistry*, 16, pp. 1142–1150 (1977).

T. Tashima et al., "Structure of a New Oligomer of Glutaraldehyde Produced by Aldol Condensation Reaction", *J. Org. Chem.*, 56, pp. 694–697 (1991).

V.P. Torchlin et al., "The Principles of Enzyme Stabilization: III. The Effects of the Length of Intra–Molecular Cross–Linkages on the Thermostability of Enzymes", *Biochem. Biophys. Acta*, 522, pp. 277–283 (1978).

V.P. Torchlin et al., "Principles of Enzyme Stabilization: V. The Possibility of Enzyme Selfstabilization Under the Action of Potentially Reversible Intramolecular Cross–Linkages of Different Length", *Biochem. Biophys. Acta*, 568, pp. 1–10 (1979).

E. Tuchsen et al., "Kinetic Properties of Subtilisin Type Carlsberg in the Crystalline State", *Carlsberg Res. Comm.*, 42, pp. 407–420 (1977).

K. Visuri et al., "Purification and Characterisation of Crystalline β–Amylase From Barley", *Eur. J. Biochem.*, 28, pp. 555–565 (1972).

K. Visuri et al., "Enzymatic Production of High Fructose Corn Syrup (HFCS) Containing 55% Fructose in Aqueous Ethanol", *Biotech. & Bioeng.*, 30, pp. 917–920 (1987).

K. Visuri, "Industrial Scale Crystallization of Glucose Isomerase", Enzyme Engineering X: International Conference, Sep. 24–29, 1989, Kashilkojima, Japan.

K. Visuri, "Method of Producing Cross–Linked Glucose Isomerase", Szabadalmi Kozlony es Vedjegyertesito, Budapest, 1990. Abstract T/52 817 (Original in Hungarian, English translation).

K. Visuri, "Crosslinked Crystalline Glucose Isomerase As Industrial Catalyst", Lecture in Detmold Starch Convention (1992).

A. Yonath et al., "Crystallographic Studies of Protein Denaturation and Renaturation. 1. Effects of Denaturants on Volume and X–ray Pattern of Cross–Linked Triclinic Lysozyme Crystals", *Biochemistry*, 16, pp. 1413–1417 (1977).

Product Information SPEYME® CIGI, Genecor International, (publication date unknown).

K.M. Lee et al., "Crosslinked Crystalline Horse Liver Alcohol Dehydrogenase As a Redox Catalyst: Activity and Stability Toward Organic Solvent", *Bioorganic Chem.*, 14, pp. 202–210 (1986).

Nakanishi et. al., Bio/Technology, vol. 3, 1985, pp. 459–464.

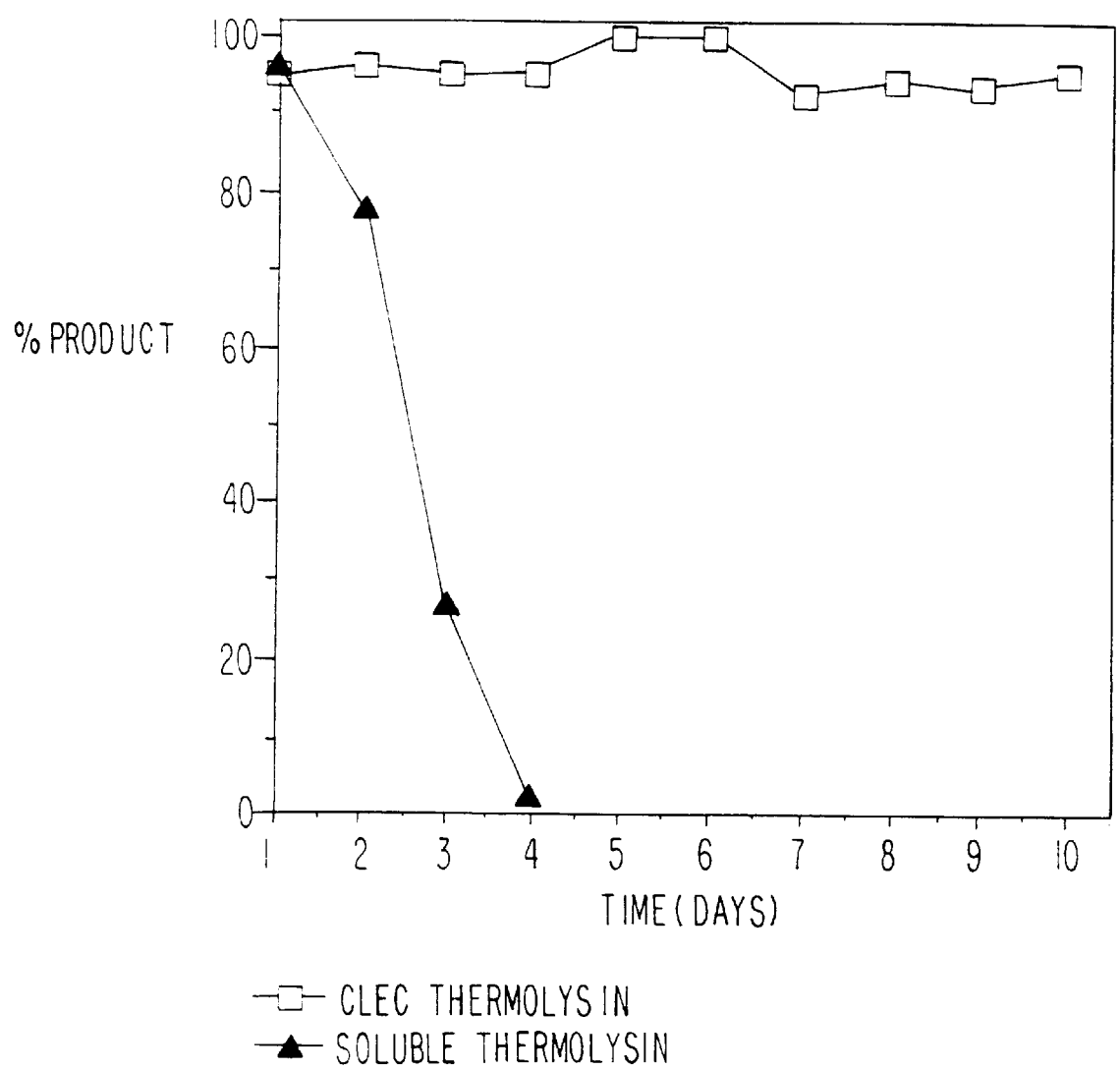

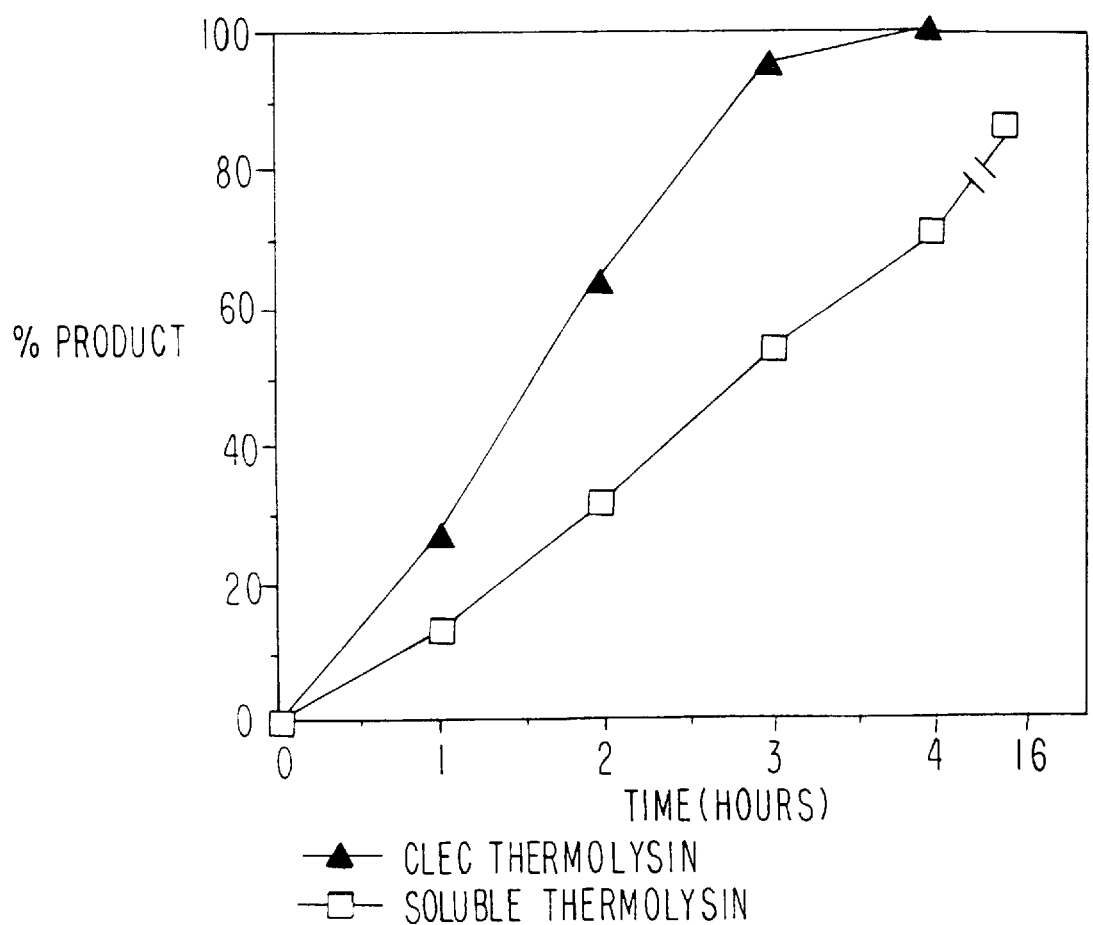

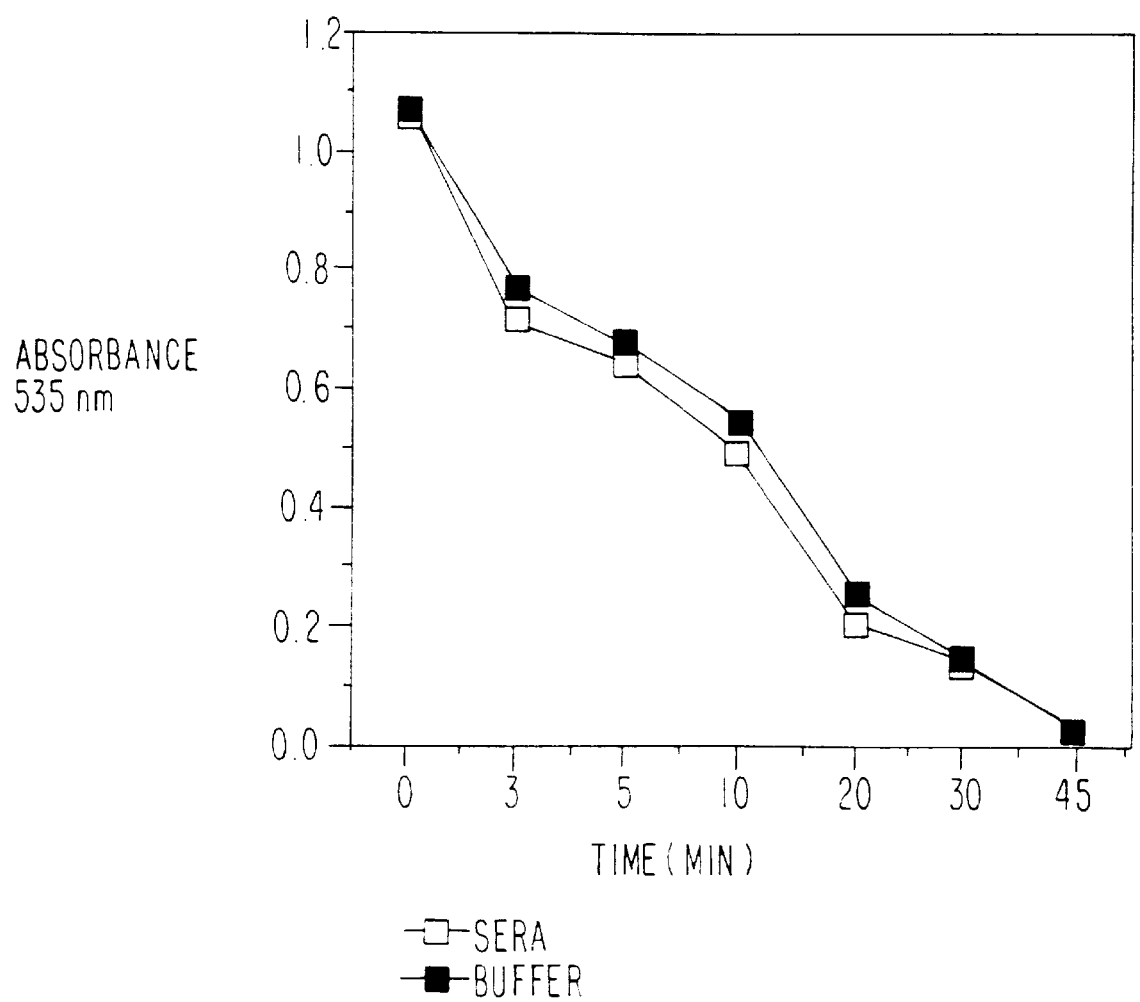

CROSSLINKED PROTEIN CRYSTALS

RELATED APPLICATIONS

This is a continuation of Ser. No. 08/017,510, Feb. 12, 1993, U.S. Pat. No. 5,618,710, which is a continuation-in-part of Ser. No. 07/864,424, Apr. 6, 1992, abandoned, which is a continuation-in-part of Ser. No. 07/720,237, Jun. 24, 1991, abandoned, which is a continuation-in-part of Ser. No. 07/562,280, Aug. 3, 1990, abandoned.

The teachings of Ser. Nos. 07/864,424, 07/720,237 and 07/562,280 are incorporated herein by reference.

BACKGROUND OF THE INVENTION

Enzymes are used as industrial catalysts for the large and laboratory scale economical production of fine and specialty chemicals (Jones, J. B., Tetrahedron 42: 3351–3403 (1986)), for the production of foodstuffs (Zaks et. al., Trends in Biotechnology 6: 272–275 (1988)), and as tools for the synthesis of organic compounds (Wong, C. -H., Science 244: 1145–1152 (1989); CHEMTRACTS-Org. Chem. 3: 91–111 (1990); Klibanov, A. M., Acc. Chem. Res. 23: 114–120 (1990)).

Enzyme-based manufacturing can significantly reduce the environmental pollution burden implicit in the large scale manufacturing of otherwise unusable chemical intermediates, as shown in the large scale production of acrylamide using the enzyme, nitrile hydratase (Nagasawa, T. and Yamada, H., Trends in Biotechnology 7: 153–158 (1989)).

Enzymes are also used in biosensor applications to detect various substances of clinical, industrial and other interest (Hall, E., "Biosensors", Open University Press (1990)). In the clinical area, enzymes may be used in extracorporeal therapy, such as hemodialysis and hemofiltration, where the enzymes selectively remove waste and toxic materials from blood (Klein, M. and Langer, R., Trends in Biotechnology 4: 179–185 (1986)). Enzymes are used in these areas because they function efficiently as catalysts for a broad range of reaction types, at modest temperatures, and with substrate specificity and stereoselectivity. Nonetheless, there are disadvantages associated with the use of soluble enzyme catalysts which have limited their use in industrial and laboratory chemical processes (Akiyama et. al., CHEMTECH 627–634 (1988)).

Enzymes are expensive and relatively unstable compared to most industrial and laboratory catalysts, even when they are used in aqueous media where enzymes normally function. Many of the more economically interesting chemical reactions carried out in common practice are incompatible with aqueous media, where, for example, substrates and products are often insoluble or unstable, and where hydrolysis can compete significantly. In addition, the recovery of soluble enzyme catalyst from product and unreacted substrate in the feedstock often requires the application of complicated and expensive separation technology. Finally, enzymes are difficult to store in a manner that retains their activity and functional integrity, for commercially reasonable periods of time (months to years) without having to resort to refrigeration (4° C. to −80° C. to liquid $N_2$ temperatures), or to maintenance in aqueous solvents of suitable ionic strength, pH, etc.

Enzyme immobilization methods have, in many instances, circumvented these disadvantages. Immobilization can improve the stability of enzyme catalysts and protect their functional integrity in the harsh solvent environments and extreme temperatures characteristic of industrial and laboratory chemical processes (Hartmeier, W., Trends in Biotechnology 3: 149–153 (1985)). Continuous flow processes may be operated with immobilized enzyme particles in columns, for example, where the soluble feedstock passes over the particles and is gradually converted into product. As used herein, the term enzyme immobilization refers to the insolubilization of enzyme catalyst by attachment to, encapsulation of, or by aggregation into macroscopic ($10^{-1}$ mm) particles.

A number of useful reviews of enzyme immobilization methods have appeared in the literature (Maugh, T. H., Science 223: 474–476 (1984); Tramper, J., Trends in Biotechnology 3: 45–50 (1985)). Maugh describes five general approaches to the immobilization of enzymes. These include: adsorption on solid supports (such as ion-exchange resins); covalent attachments to supports (such as ion-exchange resins, porous ceramics or glass beads); entrapment in polymeric gels; encapsulation; and the precipitation of soluble proteins by cross-linking them with bifunctional reagents in a random and undefined manner. In addition, one can immobilize whole cells (usually dead and made permeable) which have expressed the desired enzyme activity at high levels (e.g., Nagasawa, T. and Yamada, H., Trends in Biotechnology 7: 153–158 (1989)).

Each of these immobilization procedures has its own advantages and limitations and none can be considered optimal or dominating. In most of them, the enzyme catalyst ultimately represents only a small fraction of the total volume of material present in the chemical reactor. As such, the bulk of the immobilized medium is made up of inert, but often costly carrier material. In all of them, the immobilizing interactions of the enzyme catalyst molecules with each other and/or with the carrier material tend to be random and undefined. As a result, although these interactions confer some enhanced stability to the enzyme catalyst molecules, their relative non-specificity and irregularity makes that stabilization sub-optimal and irregular. In most cases, access to the active site of the enzyme catalyst remains ill-defined. In addition, the immobilization methods described above fail to deal with problems associated with storage and refrigeration. Nor can conventionally immobilized enzymes generally be manipulated, as in being exchanged into one or another solvent of choice, without risk to the structural and functional integrity of the enzyme. In practical terms, except for the attached tether to the carrier particle, conventionally immobilized enzymes bear close resemblance to soluble enzymes, and share with them a susceptibility to denaturation and loss of function in harsh environments. In general, immobilization methods lead to a reduction of observed enzyme-catalyzed reaction rates relative to those obtained in solution. This is mostly a consequence of the limits of inward diffusion of substrate and outward diffusion of product within the immobilized enzyme particle (Quiocho, F. A., and Richards, F. M., Biochemistry 5: 4062–4076 (1967)). The necessary presence of inert carrier in the immobilized enzyme particles increases the mean free path between the solvent exterior of the immobilized enzyme particle and the active site of the enzyme catalyst and thus exacerbates these diffusion problems. When dealing with immobilized cells, the diffusion problem is particularly severe, even if cell walls and membranes are made permeable to substrate and product in some way. One would further be concerned with the multitude of contaminating enzymatic activities, metabolites, and toxins contained in cells, and with the stability of cells in harsh solvents or extreme temperature operating environments. An improved immobilization technique which avoids the limitations of the presently available methods would be helpful in promoting the use of enzymes as industrial catalysts, particularly if it were shown to be useful on a large scale (Daniels, M. J., Methods in Enzymology 136: 371–379 (1987)).

SUMMARY OF THE INVENTION

The present invention relates to a method of immobilizing a protein, particularly an enzyme or an antibody, by forming crystals of the enzyme or antibody and, generally, also crosslinking the resulting crystals through use of a bifunctional reagent; crosslinked immobilized enzyme crystals (referred to as CLECs or CLIECs) made by this method; crosslinked immobilized antibody crystals (referred to as CLACs); the lyophilization of the resulting crystals as a means of improving the storage, handling, and manipulation properties of immobilized enzymes and antibodies; a method of making a desired product by means of a reaction catalyzed by a CLEC or a set of CLECs; and methods in which the CLACs of the present invention are used, such as a method of separating or purifying a substance or molecule of interest, in which a CLAC which recognizes (binds) the substance or molecule of interest serves as an immunospecific reagent. In another embodiment, a CLAC can be used for detection of a substance or molecule of interest in a sample, such as a biological sample, water, or other sample; this embodiment is useful, for example, for diagnostic purposes. In a further embodiment, CLACs of the present invention can be used for therapeutic purposes, in much the same manner monoclonal antibodies are now used therapeutically; in many instances, a CLAC of a particular enzyme can simply replace or substitute for presently-used (non-CLAC) antibodies. A particular advantage to CLACs is their enhanced resistance to degradation (e.g., enhanced protease resistance), relative to that of non-CLAC antibodies.

In the method of the present invention by which enzyme crystals are produced, small protein crystals (crystals of approximately $10^{-1}$ mm in size) are grown from aqueous solutions, or aqueous solutions containing organic solvents, in which the enzyme catalyst is structurally and functionally stable. In a preferred embodiment, crystals are then crosslinked with a bifunctional reagent, such as glutaraldehyde. This crosslinking results in the stabilization of the crystal lattice contacts between the individual enzyme catalyst molecules constituting the crystal. As a result of this added stabilization, the crosslinked immobilized enzyme crystals can function at elevated temperatures, extremes of pH and in harsh aqueous, organic, or near-anhydrous media, including mixtures of these. That is, a CLEC of the present invention can function in environments incompatible with the functional integrity of the corresponding uncrystallized, uncrosslinked, native enzyme or conventionally immobilized enzyme catalysts. CLACs can be made in a similar manner, using commercially available antibodies or antibodies produced against a specific antigen or hapten; entire antibodies or antibody fragments (e.g., FAb fragments) can be used to produce a corresponding CLAC.

In addition, CLECs made by this method can be subjected to lyophilization, producing a lyophilized CLEC which can be stored in this lyophilized form at non-refrigerated (room) temperatures for extended periods of time, and which can be easily reconstituted in aqueous, organic, or mixed aqueous-organic solvents of choice, without the formation of amorphous suspensions and with minimal risk of denaturation.

The present invention also relates to CLECs produced by the present method and to their use in laboratory and large scale industrial production of selected materials, such as chiral organic molecules, peptides, carbohydrates, lipids, or other chemical species. Presently, these are typically prepared by conventional chemical methods, which may require harsh conditions (e.g. aqueous, organic or near-anhydrous solvents, mixed aqueous/organic solvents or elevated temperatures) that are incompatible with the functional integrity of uncrystallized, uncrosslinked, native enzyme catalyst. Other macromolecules with catalytic activity can also be incorporated into the proposed CLEC technology. These might include catalytic antibodies (Lerner, R. A., Benkovic, S. J., and Schultz, P. G., Science 252:659–667 (1991)) and catalytic polynucleotides (Cech, T. R., Cell 64:667–669 (1991); Celander, D. W., and Cech, T. R. Science, 251:401–407 (1991)).

The present invention also relates to a method of making a selected product by means of a reaction catalyzed by a CLEC of the present invention.

In an example of the method and practice of the present invention, the enzyme thermolysin, a zinc metalloprotease, was used to synthesize a chiral precursor of the dipeptidyl artificial sweetener, aspartame. (Example 1) The enzyme thermolysin was crystallized from a starting aqueous solution of 45% dimethyl sulfoxide, and 55% 1.4M calcium acetate, 0.05M sodium cacodylate, pH 6.5. The resulting crystals were cross-linked with glutaraldehyde to form a thermolysin CLEC. The thermolysin CLEC was then transferred from the aqueous crystallization solution in which it was made, into a solution of ethyl acetate containing the substrates, N-(benzyloxycarbonyl)-L-aspartic acid (Z—L—Asp) and L-phenylalanine methyl ester (L—Phe—OMe). The thermolysin CLEC was then used to catalyze a condensation reaction of the two substrates to synthesize N-(benzyloxycarbonyl)-L-aspartyl-L-phenylalanine methyl ester (Z—L—Asp—L—Phe—OMe), which is the dipeptidyl precursor of the artificial sweetener aspartame. Using any one of many known techniques (see, e.g. Lindeberg, G., J. Chem Ed. 64: 1062–1064 (1987)) the L-aspartic acid in the synthesized dipeptidyl precursor can be deprotected by the removal of the benzyloxycarbonyl (Z—) group to produce aspartame (L—Asp—L—Phe—OMe).

In a second example of the method and practice of the present invention, the enzyme thermolysin was used to produce thermolysin CLECs. The activity and stability of thermolysin CLECs were compared to that of soluble thermolysin under optimum conditions and conditions of extreme pH and temperature, following incubation in the presence of organic solvents and following incubation in the presence of exogenous protease. (Example 2) See also Example 3, which describes further work with thermolysin CLEC.

The enzyme thermolysin was crystallized from a solution of 1.2M calcium acetate and 30% dimethyl sulfoxide pH 8.0. The resulting crystals were crosslinked with glutaraldehyde at a concentration of 12.5% to form a thermolysin CLEC. The thermolysin CLEC was then lyophilized by a standard procedure (Cooper, T. G., The Tools of Biochemistry, pp. 379–380 (John Wiley and Sons, NY (1977)) to form a lyophilized enzyme CLEC of thermolysin. This lyophilized CLEC was then transformed directly into the different aqueous, organic, and mixed aqueous/organic solvents of choice without an intervening solvent exchange procedure, without formation of amorphous suspensions, and with minimal risk of denaturation. These solvents included acetonitrile, dioxane, acetone, and tetrahydrofuran, but not to the exclusion of others. Following incubation, activity was assayed spectrophotometrically by cleavage of the dipeptide substrate FAGLA (furylacryloyl-glycyl-L-leucine amide).

In a third example of the method and practice of the present invention, the enzyme elastase (porcine pancreatic) was crystallized from an aqueous solution of 5.5 mg/ml protein in 0.1M sodium acetate at pH 5.0 at room temperature (Sawyer, L. et al., J. Mol. Biol. 118:137–208). The resulting crystals were crosslinked with glutaraldehyde at a concentration of 5% to form an elastase CLEC. (Example 4) The elastase CLEC was lyophilized as described in Example 2.

In a fourth example of the method and practice of the present invention, and as disclosed here, the enzyme esterase (porcine liver) was crystallized from an aqueous solution of 15 mg/ml protein in 0.25M calcium acetate at pH 5.6 at room temperature. The resulting crystals were crosslinked with glutaraldehyde at a concentration of 12.5% to form an esterase CLEC. (Example 5) The esterase CLEC was lyophilized as described in Example 2.

In a fifth example of the method and practice of the present invention, and as disclosed here, the enzyme lipase (*Geotrichum candidum*) was crystallized from an aqueous solution of 20 mg/ml protein in 50 mM Tris at pH 7 at room temperature. The resulting crystals were crosslinked with glutaraldehyde at a concentration of 12.5% to form a lipase CLEC. The lipase CLEC was lyophilized as described in Example 2. In addition, *Candida cylindracea* lipase has been crystallized and crosslinked, as described herein; the resulting CLEC was shown to retain significant enzymatic activity. Further, porcine pancreatic lipase has been crystallized and crosslinked; preliminary assessment of the resulting CLEC showed that it retained less activity than either of the other lipases (*G. candidum* or *C. cylindracea*). (See Examples 6, 10 and 11).

In a sixth example of the method and practice of the present invention, the enzyme lysozyme (hen egg white) was crystallized from an aqueous solution of 40 mg/ml protein in 40 mM sodium acetate buffer containing 5% sodium chloride at pH 7.4 at room temperature (Blake, C. C. F. et al., Nature, 196:1173 (1962)). The resulting crystals were crosslinked with glutaraldehyde at a concentration of 20% to form a lysozyme CLEC. (Example 7) The lysozyme CLEC was lyophilized as described in Example 2.

In a seventh example of the method and practice of the present invention, the enzyme asparaginase (*Escherichia coli*) was crystallized from an aqueous solution of 25 mg/ml protein in 50 mM sodium acetate and 33% ethanol at pH 5.0 at 4° C. The crystallization is a modification of the procedure described by Grabner et al. [U.S. Pat. No. 3,664,926 (1972)]. As disclosed here, the resulting crystals were crosslinked with glutaraldehyde at a concentration of 7.5% to form an asparaginase CLEC. (Example 8) The asparaginase CLEC was lyophilized as described in Example 2.

In an eighth example of the method and practice of the present invention, the enzyme urease (Jack Bean) was crystallized and the resulting urease crystals were crosslinked. (Example 9) The urease CLEC was lyophilized, as described in Example 2. Enzymatic activity of the urease CLEC was compared with that of soluble urease. In addition, enzymatic activity of urease CLEC in aqueous buffer was compared with activity in sera, a biologically relevant medium; activity in sera was comparable to activity in aqueous buffer.

Other enzymes which can be immobilized in a similar manner and used to catalyze an appropriate reaction include luciferase. Other enzymes, such as those listed in Tables 1–5, can also be crystallized and crosslinked using the present method, to produce a desired CLEC which can, in turn, be used to catalyze a reaction which results in production of a selected product or to catalyze a reaction which is an intermediate step (i.e. one in a series of reactions) in the production of a selected product. It is recognized that although crosslinking helps stabilize the majority of crystals, it is neither necessary nor desirable in all cases. Some crystalline enzymes retain functional and structural integrity in harsh environments even in the absence of crosslinking. Although in the preferred embodiment, the crystal is crosslinked, crosslinking is not always necessary to produce an enzyme crystal useful in the present method.

CLECs have several key characteristics that confer significant advantages over conventional enzyme immobilization methods presently in use. CLECs dispense with the need for a separate, inert support structure. Lack of an inert support will improve substrate and product diffusion properties within CLECs and provides enzyme concentrations within the crystal that are close to the theoretical packing limit for molecules of such size. High enzyme concentrations can lead to significant operational economies through the increased effective activity of a given volume of catalyst, reduction in substrate contact time with enzyme and overall reduction in plant size and capital costs (Daniels, M. J., Methods in Enzymol. 136: 371–379 (1987)). The uniformity across crystal volume and enhanced stability of the constituent enzyme in CLECs creates novel opportunities for the use of enzyme catalysis in harsh conditions, such as elevated temperature, and aqueous, organic or near-anhydrous solvents, as well as mixtures of these. In addition, the restricted solvent access and regular protein environment implicit in a crystal lattice should lead to improved metal ion and co-factor retention for CLECs vs. conventional immobilized enzyme systems.

BRIEF DESCRIPTION OF THE DRAWINGS

FIG. 17 is a graphic representation of results of assessment of urease CLEC enzymatic activity in aqueous buffer and in sera.

DETAILED DESCRIPTION OF THE INVENTION

Figure 1:
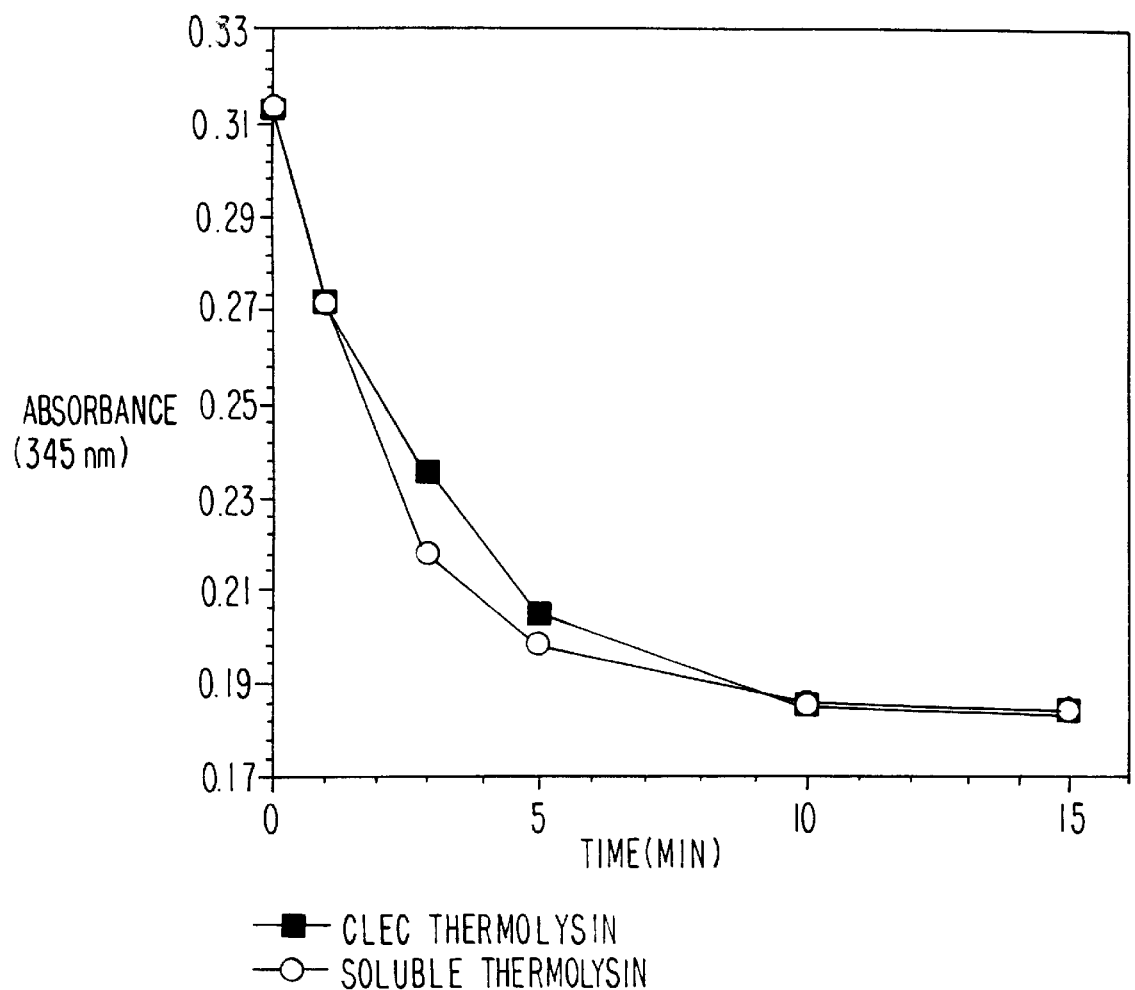
FIG. 1 is a graphic representation of results of assessment of enzymatic activity of soluble and thermolysin CLEC.

A simple, general procedure that assures stability and function for a given enzyme or set of enzymes under conditions which are of interest to the synthetic chemist and which are too harsh for use with enzymes using presently available methods, would be very useful. Cross-linked immobilized enzyme crystals (referred to as CLECs or CLIECs) as described here can be used for this purpose. Stabilization of the crystal lattice and of the constituent enzyme catalysts in the crystal by the cross-linking reaction permits the use of CLECs in environments, including aqueous, organic or near-anhydrous solvents, mixtures of these solvents, extremes of pH and elevated temperatures, which are incompatible with enzyme function using presently available methods. In addition, the stabilization of the crystal lattice in CLECs makes possible the lyophilization of CLECs by standard methods. Lyophilized CLECs can be stored for commercially attractive periods of time (months to years) in the absence of refrigeration, and facilitate the rapid and uncomplicated utilization of CLECs in industrial and laboratory scale processes by the simple addition of solvents of choice, without need for intervening solvent exchange processes. CLECs are also highly resistant to digestion by exogenous proteases. The method of the present invention facilitates the use of versatile enzyme catalysts in mainstream industrial chemical processes, as well as in the laboratory synthesis of novel compounds for research.

Although crosslinking contributes to the stability of a crystal enzyme, it is neither necessary nor desirable in all cases. Some crystallized enzymes retain functional and structural integrity in harsh environments even in the absence of crosslinking. The preferred embodiment of the present method includes cross-linking of a crystal enzyme and is described in detail in the following sections. It is to be understood, however, that crystallized enzymes which are not subsequently cross-linked can be used in some embodiments of the present invention.

The regular interactions between the constituent enzyme molecules in the crystal lattice of a CLEC result in well defined pores of limited size leading to the enzyme molecules within the body of a CLEC. As a result, substrates larger than the available pore size will not penetrate the body of the CLEC particle.

As a consequence of the limited pore size, many enzymatic reactions of commercial and academic interest involving substrates larger than the pore size of the CLECs would be beyond the scope of the present invention. This would include most reactions involving large polymers, such as proteins, polynucleotides, polysaccharides, and other organic polymers, where the number of polymeric subunits would be such as to make the polymer larger than the crystal pore size in CLECs. In such instances, however, catalysis can still take place on the CLEC surface.

The present invention is a method of immobilizing a selected protein, particularly an enzyme, by crystallizing and crosslinking the protein, resulting in production of a crosslinked immobilized enzyme crystal (CLEC) which can be used to catalyze production of a selected product, such as a peptide, carbohydrate, lipid or chiral organic molecule. The selected product can be produced by altering a single substrate (e.g., to produce a breakdown product or other product) or by combining the substrate with an additional substance or substances (e.g., a second substrate, molecule or compound to be added through the action of the CLEC). The present invention further relates to such CLECs and to a method of making a selected product by means of a CLEC-catalyzed reaction or CLEC-catalyzed step in a series of reactions. In one embodiment of the present invention, the dipeptidyl precursor of aspartame has been produced in a condensation reaction catalyzed by cross-linked immobilized thermolysin made by the present method. In another embodiment of this invention, the indicator substrate, FAGLA, has been cleaved to produce a colorimetric product, whose presence is indicative of enzyme activity in a thermolysin CLEC. FAGLA hydrolysis has been used as a model reaction to indicate the robustness of the thermolysin CLEC in a number of environments that would be normally incompatible with that enzyme's activity.

In other embodiments of this invention, the enzymes elastase, esterase, lipase, asparaginase, and lysozyme have been used to cleave various indicated substances, such as p-nitrophenyl acetate (esterase and lipase), succinyl-(ala)3-p-nitroanilide (elastase), 4-methylumbelliferyl N-acetyl-chitrioside (lysozyme) and NADH (asparaginase) and urea (urease).

By the method of this invention, one of ordinary skill in the art can adapt a protocol for making a desired product by means of a reaction catalyzed by an immobilized enzyme. The enzyme of interest, when crystallized from an appropriate solution, can be cross-linked with glutaraldehyde or other suitable bifunctional reagent in the crystallization solution to produce a CLEC of that enzyme. Subsequently, the CLEC of the enzyme of choice can be lyophilized as described in Example 2.

There are several advantages which the use of a CLEC offers over presently-available enzyme-catalyzed methods. For example, the cross-linked crystal matrix in a CLEC provides its own support. Expensive carrier beads, glasses, gels, or films are not required in order to tie down the enzyme catalyst, as they are in presently-available immobilization methods. As a result, the concentration of enzyme in a CLEC is close to the theoretical packing limit that can be achieved for molecules of a given size, greatly exceeding densities achievable even in concentrated solutions. The entire CLEC consists of active enzyme (and not inactive carrier), and thus, the diffusion-related reduction of enzyme reaction rates usually observed with conventionally immobilized enzymes relative to enzymes in solution should be minimized, since the mean free path for substrate and product between active enzyme and free solvent will be greatly shortened for CLECs (compared to a conventional immobilized enzyme carrier particles). These high protein densities will be particularly useful in biosensor, analytical and other applications requiring large amounts of protein in small volumes. In industrial processes, the superior performance and compactness of CLECs results in significant operating economies, by increasing the effective activity of a given volume of catalyst, thereby allowing reductions in plant size, as well as capital costs (Daniels, M. J., Methods in Enzymol. 136: 371–379 (1987)). CLECs are relatively monodisperse, with a macroscopic size and shape reflecting natural crystal growth characteristics of the individual enzyme catalysts. Replacement of existing carrier-immobilized enzyme media with CLECs should not be difficult, since both systems are comparable in size and shape, and both can be similarly recovered from feedstock by any number of simple methods, including basic economical operations such as filtration, centrifugation, decantation of solvent, and others.

In addition, the use of lyophilized CLECs permits routine handling and storage of these materials prior to use (dry storage at room temperature without refrigeration, for extended periods of time). Lyophilized CLECs also allow for routine formulation by direct addition of solvents and substrates of interest, without lengthy solvent exchange processes, or the formation of amorphous suspensions. The lyophilized CLEC form extends the general utility of the enzymes as catalysts to a broader spectrum of enzymes and functional conditions.

A second advantage of a CLEC is that cross-linking of the crystallized enzyme stabilizes and strengthens the crystal lattice and the constituent enzyme molecules, both mechanically and chemically. As a result, a CLEC may be the only means of achieving significant concentrations of active enzyme catalyst in harsh aqueous, organic, near-anhydrous solvents, or in aqueous-organic solvent mixtures. The use of enzymes as catalysts in organic syntheses has been hampered by their tendency to denature in the presence of non-aqueous solvents, and particularly, in mixtures of aqueous and non-aqueous solvents (Klibanov, A. M., Trends in Biochemical Sciences, 14:141–144 (1989)). In CLECs, the restriction of conformational mobility that leads to stability is provided by the inter-molecular contacts and cross-links between the constituent enzyme molecules making up the crystal lattice, rather than by the near-absence of water in the medium. As a result, intermediate water concentrations can be tolerated by enzymes when formulated as CLECs, as has previously not been possible (see Table 12). In commercial applications, aqueous-organic solvent mixtures allow manipulation of product formation by taking advantage of relative solubilities of products and substrates. Even in aqueous media, enzyme catalysts, immobilized or soluble, are subject to mechanical forces within a chemical reactor that can lead to denaturation and a shortened half-life. The chemical cross-links within the CLEC provide the necessary mechanical strength (Quiocho and Richards, Proc. Natl. Acad. Sci. (USA) 52: 833–839 (1964)) that results in increased reactor life for the enzyme catalyst.

A third advantage of a CLEC is that as a result of its crystalline nature, a CLEC can achieve uniformity across the entire cross-linked crystal volume. Crystalline enzymes as described herein are grown and cross-linked in an aqueous environment and, therefore, the arrangement of molecules within the crystal lattice remains uniform and regular. This uniformity is maintained by the intermolecular contacts and chemical cross-links between the enzyme molecules constituting the crystal lattice, even when exchanged into other aqueous, organic or near-anhydrous media, or mixed aqueous/organic solvents. In all of these solvents, the enzyme molecules maintain a uniform distance from each other, forming well-defined stable pores within the CLECs that facilitate access of substrate to the enzyme catalysts, as well as removal of product. Uniformity of enzyme activity is critical in industrial, medical and analytical applications where reproducibility and consistency are paramount.

A fourth advantage of using a CLEC is that it should exhibit an increased operational and storage half-life. Lattice interactions, even in the absence of cross-linking, are known to stabilize proteins, due in part to restrictions of the conformational degrees of freedom needed for protein denaturation. In CLECs, the lattice interactions, when fixed by chemical cross-links, are particularly important in preventing denaturation, especially in mixtures of aqueous and non-aqueous solvents (Klibanov, A. M., Trends in Biochemical Sciences 14: 141–144 (1989)). Enzymes that have been in the crystalline state for months or years routinely retain a high percentage of their catalytic activity. Cross-linked immobilized enzyme crystals stored in anhydrous solvents will be even further protected from microbial contamination and damage, which is a serious problem in storing large quantities of protein in a nutrient rich, aqueous environment.

In the case of a lyophilized CLEC, the immobilized enzyme is stored in the absence of solvent. That, and the stabilization achieved by cross-linking allows for the storage in the absence of refrigeration for long periods of time.

A fifth advantage of using a CLEC is that it should exhibit enhanced temperature stability as a consequence of the cross-links stabilizing the crystal lattice. Carrying out reactions at a higher temperature than that used with conventional methods would increase reaction rates for the chemical reactions of interest, both thermodynamically, and by enhancing the diffusion rate into and out of the crystal lattice of CLECs. These combined effects would represent a major improvement in reaction efficiency, because they would maximize the productivity of a given quantity of enzyme catalyst, which is generally the most expensive component of the reaction process (Daniels, M. J., Methods in Enzymol. 136: 371–379 (1987)). The temperature stability exhibited by CLECs is remarkable because most enzyme systems require mild reaction conditions. CLECs would also be stabilized against denaturation by transient high temperatures during storage.

A final advantage of use of a CLEC is that pores of regular size and shape are created between individual enzyme molecules in the underlying crystal lattice. This restricted solvent accessibility greatly enhances the metal ion or cofactor retention characteristics of CLEC as compared to conventionally immobilized enzymes and enzymes in solution. This property of CLEC will permit the use of economically superior continuous-flow processes in situations (see e.g. Oyama et. al. Methods in Enzymol. 136 503–516 (1987)) where enzyme would otherwise be inactivated by metal ion or cofactor leaching. For example, in the thermolysin-mediated synthesis of the dipeptidyl aspartame precursor, Z—L—Asp—L—Phe—OMe, conventionally immobilized enzyme is known to lose catalytic activity in continuous-flow column processes, in part through the leaching of calcium ions essential for thermolysin activity. In practice, leaching of calcium ions has forced the use of less efficient batch processes (Nakanishi et. al., Biotechnology 3: 459–464 (1985)). Leaching occurs when calcium ion complexes are formed with substrate Z—L—Asp, in competition with the natural calcium binding sites on the surface of the enzyme, resulting in the loss of catalytic activity. The high density of enzyme, and the correspondingly limited volume accessible to solvent in the interstices of the CLECs, discourages the formation of the competing L—Asp—$Ca^{++}$ complexes responsible for metal ion leaching.

In addition, crystallized, crosslinked antibodies, or CLACs, made by a method similar to that used to produce CLECs, are the subject of the present invention. As described with reference to CLECs, although crosslinking contributes to the stability of a crystallized antibody, it is neither necessary nor desirable in all instances. Crystallized antibodies which are not subsequently crosslinked can be used in some embodiments of the present invention. CLACs of the present invention have the same advantages as described herein for CLECs. A particularly useful advantage is the enhanced resistance to degradation (e.g., protease degradation) of CLACs.

Preparation of CLECs—Enzyme Crystallization

In the method of the present invention, a cross-linked immobilized enzyme crystal (or CLEC) is prepared as follows:

Enzyme crystals are grown by the controlled precipitation of protein out of aqueous solution, or aqueous solution containing organic solvents. Conditions to be controlled include, for example, the rate of evaporation of solvent, the presence of appropriate co-solutes and buffers, and the pH and temperature. A comprehensive review of the various factors affecting the crystallization of proteins has been published by McPherson (Methods Enzymol. 114: 112 (1985)). In addition, both McPherson and Gilliland (J. Crystal Growth 90: 51–59 (1988)) have compiled comprehensive lists of all proteins and nucleic acids that have been reported as crystallized, as well as the conditions that lead to their crystallization. A compendium of crystals and crystallization recipes, as well as a repository of coordinates of solved protein and nucleic acid crystal structures, is maintained by the Protein Data Bank (Bernstein et. al. J. Mol. Biol. 112: 535–542 (1977)) at the Brookhaven National Laboratory. Such references can be used to determine the conditions necessary for the crystallization of a given protein or enzyme previously crystallized, as a prelude to the formation of an appropriate CLEC, and can guide the formulation of a crystallization strategy for proteins that have not. Alternatively, an intelligent trial and error search strategy (see eg., Carter, C. W. Jr. and Carter, C. W., J. Biol. Chem. 254: 12219–12223 (1979)) can, in most instances, produce suitable crystallization conditions for most proteins, including, but not limited to, those discussed above, provided that an acceptable level of purity can been achieved for these. The level of purity required can vary widely from protein to protein. In the case of lysozyme, for example, the enzyme has been crystallized directly from its unpurified source, the hen egg-white (Gilliland, G. L., J. Crystal Growth 90: 51–59 (1988)). For use as CLECs in the method of this invention, the large single crystals which are needed for X-ray diffraction analysis are not required, and may, in fact, be undesirable because of diffusion problems related to crystal size. Microcrystalline showers (ie., crystals in the order of $10^{-1}$ mm in size/cross section) are suitable for CLECs and are often observed, although seldom reported in the X-ray crystallographic literature. Micro-crystals are very useful in the method of this invention to minimize problems with diffusion (see eg., Quiocho, F. A., and Richards, F. M., Biochemistry 5: 4062–4076 (1967)).

In general, crystals are produced by combining the protein to be crystallized with an appropriate aqueous solvent or aqueous solvent containing appropriate precipitating agents, such as salts or organics. The solvent is combined with the protein at a temperature determined experimentally to be appropriate for the induction of crystallization and acceptable for the maintenance of protein stability and activity. The solvent can optionally include co-solutes, such as divalent cations, co-factors or chaotropes, as well as buffer species to control pH. The need for co-solutes and their concentrations are determined experimentally to facilitate crystallization. In an industrial scale process, the controlled precipitation leading to crystallization can best be carried out by the simple combination of protein, precipitant, co-solutes, and optionally buffers in a batch process. Alternative laboratory crystallization methods, such as dialysis, or vapor diffusion can also be adapted. McPherson (Methods Enzymol. 114: 112 (1985)), and Gilliland (J. Crystal Growth 90: 51–59 (1988)) include a comprehensive list of suitable conditions in their reviews of the crystallization literature. Occasionally, incompatibility between the cross-linking reagent and the crystallization medium might require exchanging the crystals into a more suitable solvent system.

Many of the proteins for which crystallization conditions have already been described in the literature, have considerable potential as practical enzyme catalysts in industrial and laboratory chemical processes, and are directly subject to formulation as CLECs within the method of this invention. Table 1 is a sampling of enzymes that have already been crystallized. Note that the conditions reported in most of these references have been optimized for the growth of large, diffraction quality crystals, often at great effort. Some degree of adjustment of conditions for the smaller crystals used in making CLECS might be necessary in some cases.

TABLE 1

| Enzyme | Microbial or biological source | References (including those cited therein) |
| --- | --- | --- |
| • alcohol dehydrogenase | horse liver | Eklund et al., J. Mol. Biol. 146: 561–587(1981) |
| • alcohol oxidase | *Pichia pastoris* | Boys et al., J. Mol. Biol. 208: 211–212 (1989) |
| | | Tykarska et al., J. Protein Chem. 9: 83–86(1990) |
| • aldolase (fructose-bisphosphate) | rabbit muscle | Eagles et al., J. Mol. Biol. 45: 533–544 (1969) |
| | | Heidmer et al., Science 171: 677–680 (1971) |
| | calf muscle human muscle | Goryunov et al., Biofizika 14: 1116–1117(1969) |

TABLE 1-continued

| Enzyme | Microbial or biological source | References (including those cited therein) |
|---|---|---|
| | | Millar et al., Trans. Roy. Soc. Lond. B293: 209–214(1981) |
| | Drosophila melanogaster | Brenner et al., J. Biol. Chem. 257: 11747–11749(1982) |
| • aldolase (PKDG) | Pseudomonas putida | Vandlen et al., J. Biol. Chem. 248: 2251–2253(1973) |
| • alkaline phosphatase | Escherichia coli | Sowadski et al., J. Mol. Biol. 150: 245–272(1981) |
| • asparaginase | Erwinia carotova | North et al., Nature 224: 594–595 (1969) |
| | Escherichia coli | Epp et al., Eur. J. Biochem. 20: 432–437(1971) |
| | Escherichia coli | Yonei et al., J. Mol. Biol. 110: 179–186(1977) |
| | Proteus vulgaris | Tetsuya et al., J. Biol. Chem. 248: 7620–7621(1972) |
| • carbonic anhydrase | human erythrocyte (C) | Kannan et al., J. Mol. Biol. 12: 740–760(1965) |
| | human erythrocyte (B) | Kannan et al., J. Mol. Biol. 63: 601–604(1972) |
| | bovine erythrocyte | Carlsson et al., J. Mol. Biol. 80: 373–375(1973) |
| • catalase | horse erythrocyte | Glauser et al., Acta Cryst. 21: 175–177(1966) |
| | Micrococcus luteus | Marie et al., J. Mol. Biol. 129: 675–676(1979) |
| | Penicillium vitale | Vainshtein et al., Acta Cryst. A37: C29(1981) |
| | bovine liver | Eventoff et. al., J. Mol. Biol. 103: 799–801(1976) |
| • creatine kinase | bovine heart | Gilliland et al., J. Mol. Biol. 170: 791–793(1983) |
| | rabbit muscle | McPherson, J. Mol. Biol. 81: 83–86 (1973) |
| • glutaminase | Actenobacter glutanimasificans | Wlodawer et al., J. Mol. Biol. 99: 295–299(1975) |
| | Pseudomonoas 7A | Wlodawer et al., J. Mol. Biol. 112: 515–519(1977) |
| • glucose oxidase | Asperigillus niger | Kalisz et al., J. Mol. Biol. 213: 207–209(1990) |
| • β-lactamases | Staphylococcus aureus | Moult et al., Biochem J. 225: 167–176(1985) |
| | Bacillus cereus | Sutton et al., Biochem J. 248: 181–188(1987) |
| • lacate dehydrogenase | porcine | Hackert et al., J. Mol. Biol. 78: 665–673(1973) |
| | chicken | Pickles et al, J. Mol. Biol. 9: 598–600 (1964) |
| | dogfish | Adams et al., J. Mol. Biol. 41: 159–188 (1969) |
| | Bacillus stearothermophilus | Schar et al., J. Mol. Biol. 154: 349–353 (1982) |
| • lipase | Geotrichum candidum | Hata et al, J. Biochem. 86: 1821–1827 (1979) |
| | horse pancreatic Mucor meihei | Lombardo et al., J. Mol. Biol. 205: 259–261(1989) |
| | | Brady et al., Nature 343: 767–770 (1990) |
| | human pancreatic | Winkler et al, Nature 343: 771–774 (1990) |
| • luciferase | Firefly | Green, A.A., et al., Biochem. Biophys. Acta. 20: 170(1956) |
| • luciferase | Vibrio harveyii | Swanson et al., J. Biol. Chem. 260: 1287–1289(1985) |
| • nitrile hydratase | Brevibacterium R312 | Nagasawa et al., Biochem. Biophys. Res. Commun. 139: 1305–1312 (1986) |
| | P. chlororaphis B23 | Nagasawa et. al., Eur J. Biochem. 162: 691–698(1987) |
| • peroxidase | horseradish | Braithwaite et al., J. Mol. Biol. 106: 229–230 (1976) |
| | horseradish roots (Type E4) Japanese radish | Aibara et al., J. Biochem. 90: 489–496 (1981) Morita, Acta Cryst. A28: S52(1979) |
| • peroxidase (chloride) | Caldaromyces fumago | Rubin et al., J. Biol. Chem. 257: 7768–7769(1982) |

TABLE 1-continued

| Enzyme | Microbial or biological source | References (including those cited therein) |
| --- | --- | --- |
| • peroxidase (cytochrome) | Sarchomyces cerevisae | Poulos et al, J. Biol. Chem, 253: 3730–3735(1978) |
| • peroxidase (glutathione) | bovine erythrocyte | Ladenstein et al., J. Mol. Biol. 104: 877–882(1979) |
| • subtilisin | Bacillus subtilis (Novo) | Drenth et al., J. Mol. Biol. 28: 543–544 (1967) |
| | Bacillus amyloliquefaciens (BPN) | Wright et al., Nature 221: 235–242 (1969) |
| | Bacillus subtilis (Carlsberg) | Petsko et al., J. Mol. Biol. 106: 453–456(1976) |
| • superoxide dismutase | bovine | Richardson et al., J. Biol. Chem. 247: 6368–6369(1972) |
| | spinach | Morita et al., J. Mol. Biol. 86: 685–686 (1974) |
| | Saccharomyces cerevisiae, Escherichia coli | Beem et al., J. Mol. Biol. 105: 327–332 (1976) |
| | Bacillus stearothermophillus | Bridgen et al., J. Mol. Biol. 105: 333–335(1976) |
| | Pseudonionas ovalis | Yamakura et al., J. Biol. Chem. 251: 4792–4793(1976) |
| • thermolysin | Bacillus thermoproteolyticus | Matthews et al., Nature New Biol. 238: 37–41(1972) |
| • urease | jack bean | Sumner, J. B., J. Biol. Chem. 69: 435 (1926) |
| • xylose isomerase | Streptomyces rubiginosus | Carrell et al., J. Biol. Chem. 259: 3230–3236(1984) |
| | Arthrobacter B3728 | Akins et al., Biochym. Biophys Acta 874: 375–377(1986) |
| | Streptomyces olivochromogenes | Farber et al., Protein Engineering 1: 459–466(1987) |
| | Streptomyces violaceoniger | Glasfeld et al., J. Biol. Chem. 263: 14612–14613(1988) |
| | Actinoplanes missouriensis | Rey et al., Proteins: Struc. Func. Genet. 4: 165–172 (1988) |

Preparation of CLECs—Cross-linking Reaction

Once crystals are grown in a suitable medium, they can be cross-linked. Cross-linking results in stabilization of the crystal lattice by introducing covalent links between the constituent enzyme molecules in the crystal. This makes possible the transfer of enzyme into an alternate reaction environment that might otherwise be incompatible with the existence of the crystal lattice, or even with the existence of intact undenatured protein. Cross-linking can be achieved by a wide variety of bifunctional reagents, although in practice, simple, inexpensive glutaraldehyde has become the reagent of choice. (For a representative listing of other available cross-linking reagents, one can consult, for example, the 1990 catalog of the Pierce Chemical Company). Cross-linking with glutaraldehyde forms strong covalent bonds between primarily lysine amino acid residues within and between the enzyme molecules in the crystal lattice that constitute the crystal. The cross-linking interactions prevent the constituent enzyme molecules in the crystal from going back into solution, effectively insolubilizing or immobilizing the enzyme molecules into microcrystalline (ideally $10^{-1}$ mm) particles. The macroscopic, immobilized, insolubilized crystals can then be readily separated from the feedstock containing product and unreacted substrate by simple procedures such as filtration, decantation, and others. They can also be used in CLEC packed columns in continuous flow processes, where they exhibit enhanced cofactor and metal ion retention properties.

By the method of this invention, CLECs are obtained for use as enzyme catalysts in existing and novel environments. The enhanced stability of the CLECs, which results from the cross-linking reaction, makes it possible to transfer the CLEC into a solvent (e.g., aqueous, organic or near-anhydrous solvents, or a mixture of these), in which it would otherwise be incompatible, and to carry out chemical reactor operation at elevated temperatures of extremes of pH. The macroscopic CLEC catalyst particles can also be readily manipulated, allowing recovery from feedstock by simple methods, such as filtration, centrifugation, or decantation of solvent. In addition, these can be used in packed columns in continuous flow processes.

Preparation of CLECs—Lyophilization

A suspension of one volume of cross-linked thermolysin crystals in ten volumes of demineralized water at pH 7.0 was lyophilized overnight using a VirTis Model #24 lyophilizer. Lyophilized crystals were stored at room temperature or at 4° C. prior to reconstitution, which was accomplished by adding ten volumes of the solvent of choice directly onto crystals taken from storage. Re-hydrated crystals were reconstituted in 10 mM calcium acetate buffer at pH 7.0 for the FAGLA cleavage experiments. Reconstituted lyophilized CLECs were routinely stored at room temperature. In contrast, soluble enzyme required storage at −70° C. to maintain specific activity longer than a week. This protocol was used for all the enzymes described in the exemplification included here.

Synthesis of Aspartame Precursor with Thermolysin CLEC

The method of the present invention, by which cross-linked crystal enzymes are produced, is described below and exemplified by the production of cross-linked immobilized enzyme crystals of thermolysin for use in the production of the dipeptidyl precursor of aspartame, in ethyl acetate, which is a near-anhydrous organic, solvent. Thermolysin, a protein which has been crystallized and whose structure has been solved at 1.6 Å resolution (Holmes and Matthews, J. Mol. Biol. 160: 623–639 (1982)), is one example of an enzyme which can be used as a CLEC in the present method. Thermolysin is used in the manufacture of the artificial sweetener aspartame (Isowa et. al. U.S. Pat. No. 4,436,925 (1984); Lindeberg, J. Chem. Ed. 64: 1062–1064 (1987); Nakanishi et. al., Biotechnology 3: 459–464 (1985); Oyama, et. al., Methods in Enzymol. 136: 503–516 (1987)). At the present time, most aspartame appears to be produced by a conventional synthetic chemistry approach, although use of conventionally immobilized thermolysin in near-anhydrous media has produced encouraging results (Oyama et. al., J. Org. Chem. 46: 5242–5244 (1981); Nakanishi et. al., Biotechnology 3: 459–464 (1985)). Improvement in the enzymatic approach to aspartame production, such as is possible through use of the present method, would make it competitive with the presently-used method, both in terms of convenience and cost (Oyama, et. al., *Methods in Enzymol.* 136: 503–516 (1987)).

Assessment of Thermolysin CLECs

Figure 5C:
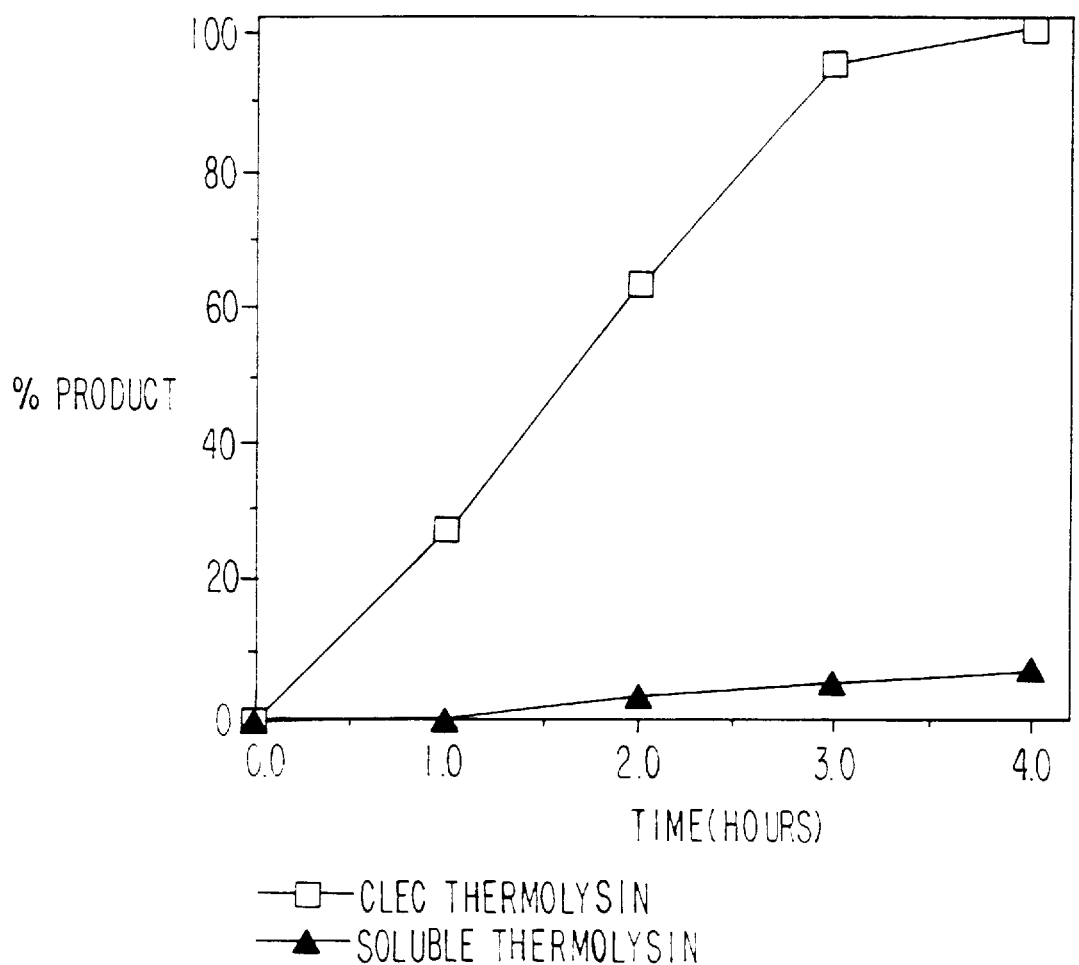
FIG. 5 is a series of graphic representations (A–C) of results of assessment of continuous batch synthesis of the aspartame precursor using soluble thermolysin and CLEC thermolysin.

The method of the present invention has also been used to produce thermolysin CLECs which have been assessed as to their pH dependence and stability, stability at elevated temperature, resistance to exogenous proteolysis and stability in the presence of an organic solvent. Thermolysin CLECs were compared to soluble thermolysin, as described in detail in Example 2 and FIGS. 1–4. Results of the assessment showed the following:

1. As to pH dependence and stability, both forms demonstrate maximum activity at pH 7 and demonstrate similar activity in the acidic range. In the alkaline pH range, the CLEC maintains maximum activity to pH 10; the soluble thermolysin has 75% activity at pH 8.5, only 25% activity at pH 9 and is completely inactive at pH 9.5.
2. The additional stabilization achieved in CLECs results in enzymatic activity at higher temperatures than is possible with soluble thermolysin. Enhanced stability of CLEC thermolysin at lower temperatures makes storage simpler than it is for the soluble enzyme. Thermal stability and resistance to autolysis was also demonstrated for thermolysin CLECs, which retained maximum activity after five days of incubation at 65° C. In contrast, soluble thermolysin lost 50% of its initial activity after two hours incubation and demonstrated negligible activity after 24 hours incubation at 65° C.
3. Enzymatic activity of thermolysin CLECs was unaffected by four days' incubation in the presence of the powerful streptococcal protease, Pronase®. In contrast, soluble thermolysin was rapidly degraded and lost all activity after 90 minutes incubation.
4. Thermolysin CLECs and soluble thermolysin exhibited markedly different stability in the presence of organic solvents, as shown in Table 12. The thermolysin CLECs retained greater than 95% maximum activity following incubation with all organic solvents assessed. Additional work with soluble and CLEC thermolysin catalysed synthesis is described in Example 6 and FIG. 5.

These features of thermolysin CLECs and other enzyme CLECs make them particularly useful, since they are easier to store, more stable and less easily inactivated or degraded than corresponding soluble enzymes.

Assessment of Elastase CLECs

Figure 6:
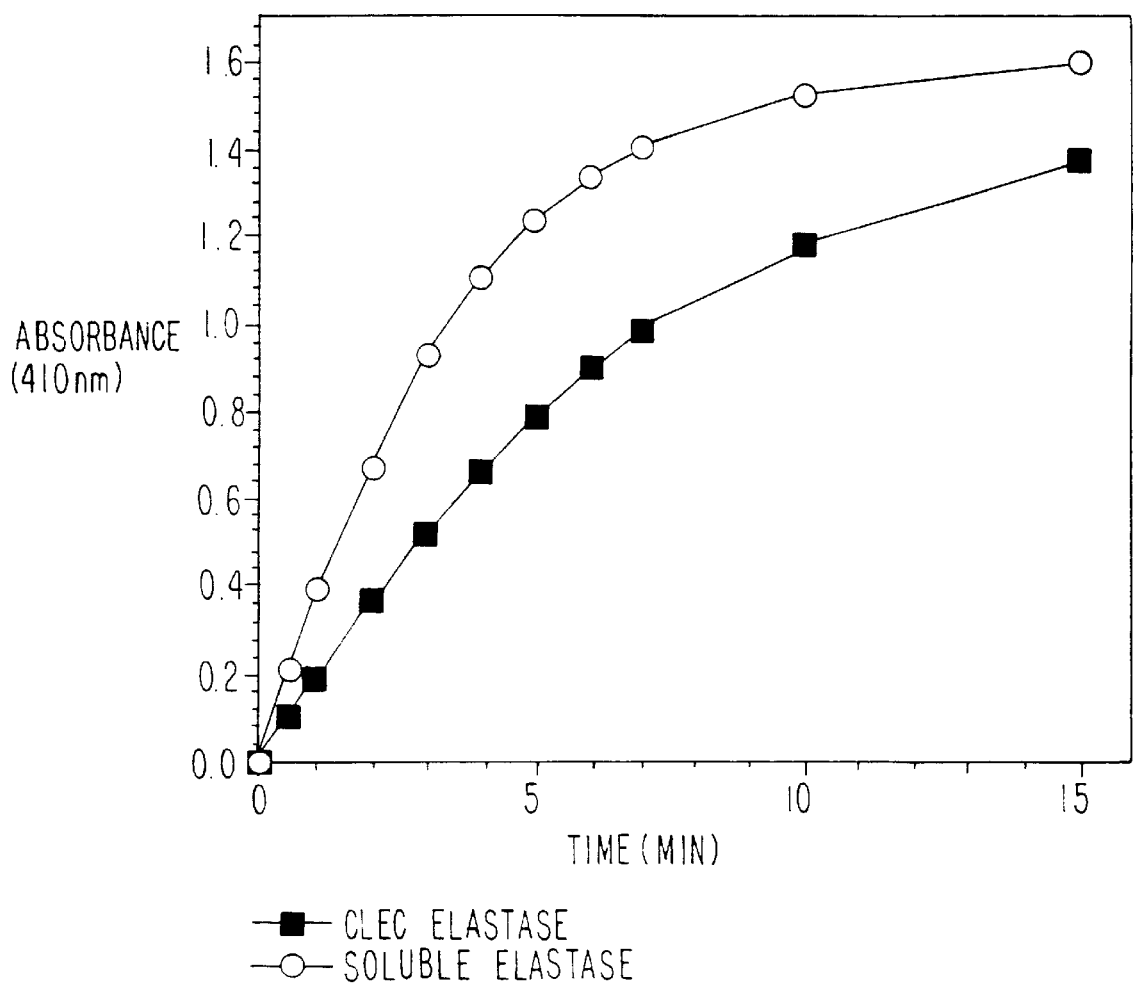
FIG. 6 is a graphic representation of results of the assessment of enzymatic activity for soluble elastase and the corresponding elastase CLEC.
Figure 7:
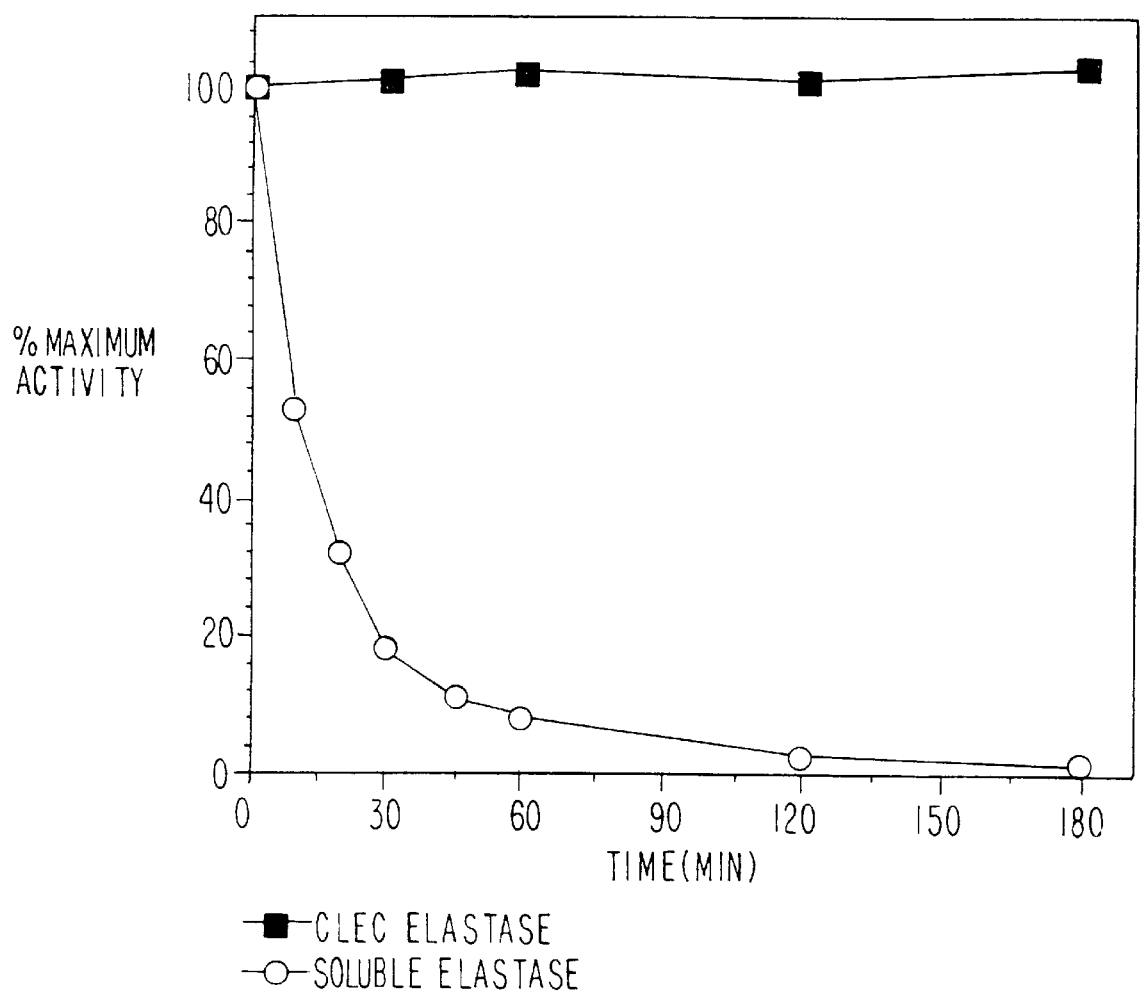
FIG. 7 is a graphic representation of the resistance of soluble elastase and the corresponding elastase CLEC to exogenous proteolytic degradation.

The method of the present invention has also been used to produce elastase CLECs which have been assessed as to their activity and resistance to exogenous proteolysis. Elastase CLECs were compared to soluble elastase, as described in detail in Example 4 and FIGS. 6 and 7. Results of the assessment demonstrated the following:

1. Elastase CLECs retain approximately 50% activity compared to soluble enzyme.
2. Soluble elastase was rapidly degraded by protease. Activity of soluble elastase was reduced to 50% of initial activity following ten minutes incubation in the presence of protease. After one hour incubation the soluble enzyme had lost more than 90% of its initial activity. In contrast the enzymatic activity of the elastase CLEC was unaffected by incubation with protease.

Assessment of Esterase CLECs

The method of the present invention has also been used to produce esterase CLECs which have been assessed as to their activity and resistance to exogenous proteolysis. Esterase CLECs were compared to soluble esterase, as described in detail in Example 5 and FIGS. 8 and 9. Results of the assessment demonstrated the following:

1. Esterase CLECs retain approximately 50% activity compared to soluble enzyme.
2. Soluble esterase was highly susceptible to proteolytic degradation. Activity of soluble esterase was reduced to 50% of initial activity following ten minutes incubation in the presence of protease. After one hour incubation the soluble enzyme had lost more than 90% of its initial activity. In contrast the enzymatic activity of the esterase CLEC was unaffected by incubation with protease.

Assessment of Lipase CLECs

The method of the present invention has also been used to produce lipase CLECs which have been assessed as to their activity. Lipase CLECs were compared to soluble lipase, as described in detail in Examples 6 and 10 and FIG. 9. Results of the assessment demonstrated that *G. candidum* and *C. cylindracea* lipase CLECs retain significant activity, compared to soluble enzyme (Examples 6 and 10) and that the porcine pancreatic lipase retained activity to a limited extent. (Example 11)

Assessment of Lysozyme CLECs

Figure 11:
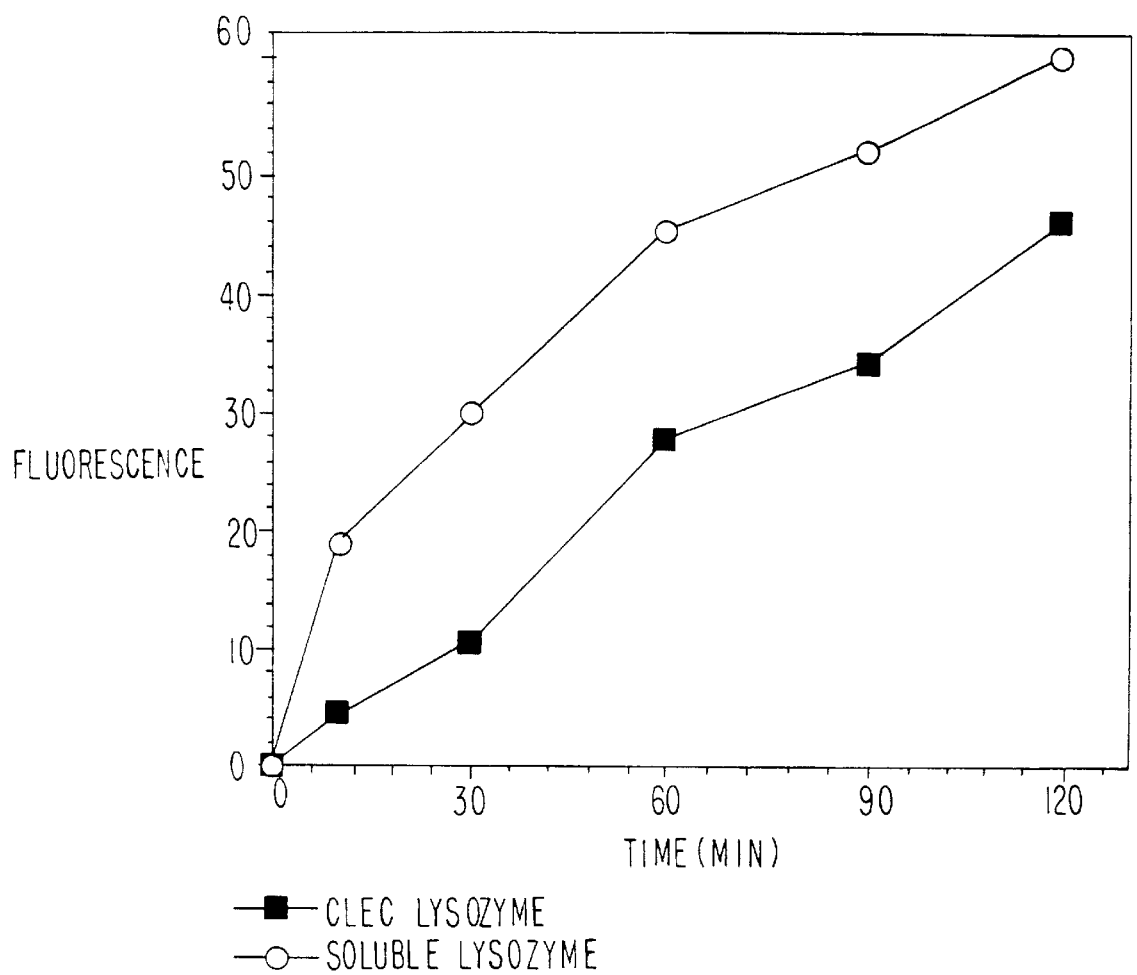
FIG. 11 is a graphic representation of results of the assessment of enzymatic activity for soluble lysozyme and the corresponding lysozyme CLEC.

The method of the present invention has also been used to produce lysozyme CLECs which have been assessed as to their activity and resistance to exogenous proteolysis. Lysozyme CLECs were compared to soluble lysozyme as described in detail in Example 7 and FIG. 11. Results of the assessment demonstrated that lysozyme CLECs retain approximately 50% activity compared to soluble enzyme.

Assessment of Asparaginase CLECs

The method of the present invention has also been used to produce asparaginase CLECs which have been assessed as to their activity. Asparaginase CLECs were compared to soluble asparaginase, as described in detail in Example 8 and FIG. 12. Results of the assessment demonstrated the following asparaginase CLECs retain approximately 77% activity compared to soluble enzyme.

Assessment of Urease CLECs

The method of the present invention has also been used to produce urease CLECs which have been assessed as to their activity. Urease CLECs were compared to soluble urease, as described in detail in Example 9 and FIGS. 13–16 and, in addition, urease CLEC activity in an aqueous buffer was compared with its activity in sera, which is a biologically relevant medium. (Example 9 and FIG. 17) Results of the assessment demonstrated that urease CLECs retain significant enzymatic activity and that there was comparable urease activity in aqueous buffer and in sera.

General Applicability of CLECs

As disclosed here, CLECs represent a novel technology with broad use in many areas, including, but not limited to, industrial scale syntheses, laboratory tools, biosensors, and medical applications. Examples of various systems using conventionally immobilized enzyme methods in their execution are given in Tables 2–5 below. One skilled in the art should be able to adapt these, and similar systems, to the CLEC technology disclosed in this application. To illustrate this, specific examples are discussed in more detail from each of the categories listed.

Table 2 below lists examples which use conventionally immobilized enzymes in an industrial process, which examples can be readily adapted to the CLEC technology disclosed here.

TABLE 2

| Enzyme | Production or application | Substrates | References (including those cited) |
|---|---|---|---|
| • thermolysin | • aspartame precursor | Z—Asp, L—Phe—OMe | Oyama et al., J. Org. Chem. 46: 5242–5244 (1981) Nakanishi et al., Trends in Biotechnology 3: 459–464 (1985) |
| • subtilisin | • aspartame | L—Asp—L—Phe, OMe | Davino, A.A., U.S. Pat. 4293648(1981) |
| • lipase | • cocoa fat substitutes | palm oils | Harwood, J., Trends in Biochemical Sciences 14: 125–126(1989) Macrae, A.R., J. Am. Oil Chem Soc. 60: 291–294 (1983) |
| • nitrile hydratase, nitrilases, amidase | • acrylamide | acrylonitrile | Nagasawa, T. and Yamada, H., Trends in Biotechnology 7: 153–158 (1989) |
| • amino acylase (fungal) • amino acid esterase, • subtilisin • amidases • hydantionases • specific dehydrogenases • amino peptidase • transaminase | • amino acid resolution | N-acyl-D,L amino acids esters of D,L amino acids amides of D,L amino acids hydantoins a-hydroxycarboxylic acids | Schmidt-Kastner, G. & Egerer, P. in Biotechnology vol 6a: 387–421 (1984) and references therein. Fusee, M.C., Methods in Enzymology 136: 463 (1987) Fusee, M.C., Methods in Enzymology 136: 463 (1987) |
| • amino acid dehydrogenase + formate dehydrogenase | • amino acid production: general • amino acid production: specific | keto or hydroxy acids | Rozzell, J.D., Methods in Enzymology 136: 479 (1987) Enzymes in Industry; Ed Gerhartz. W., VCH Press 1990 |
| • L-aspartase • L-aspartate 4-decarboxylase aspartase + L aspartate 4 decar-boxylase • ACL hydrolase • L-ACT hydrolase | L aspartic acid L-alanine L-lysine L-cysteine L-isoleucine L-methionine | fumarate/fumaric acid L-aspartic acid, ammonium fumarate D,L-a amino e-caprolactam (ACL) DL-2amino2 thiazoline 4carboxylic acid | |
| • lyase • L-tryptophan synthetase | L-phenylalanine L-tryptophan L-valine | cinnamate indole, L-serine | |
| • fumarase | L-malic acid | fumarate | |
| • hydantoinase | D n carbamoyl p-hydroxy- phenyl glycine | 5p-hydroxy hydantoin | |
| • lipases, esterases | • resolution of racemates by stereoselective synthesis | synthetic chemistry | Jones, J.B., Tetrahedron 42: 3351–3403 (1988) Butt, S. and Roberts, S.M., Natural Product Reports 489–503 (1986), and references cited therein for a more comprehensive review of this area |
| • fumarase | • L-malic acid | fumaric acid | Chibata et al., Methods in Enzymology 136: 455 (1987) |
| • lactase, β-galactosidases | • disaccharide synthesis eg galactosyl-N-acetyl galactosamine | lactose & N-acetyl galactosamine | Larsson et al., Methods in Enzymology 136: 230 (1987) |
| • lipase, esterase | • L-menthol | 4 isomer mix | Fukui, S., Tanaka, A., Methods in Enzymology 136: 293 (1987) |

TABLE 2-continued

| Enzyme | Production or application | Substrates | References (including those cited) |
|---|---|---|---|
| • amidases | • D-valine (intermediate for pyrethroid insecticide fluvinate) | D,L amino acid amide | Schmidt-Kastner, G. & Egerer. P. in Biotechnology vol 6a: 387–421 (1984) and references therein. |
| • lipase (Candida cylindricea) | • R(+)2 phenoxy-propionic acids (herbicides) | 2 chloro propionic acids | Biocatalysts in Organic Syntheses eds Tramper, van de Plas & Linko; Proceedings of International Symposium in Netherlands 1985 |
| • lipases, esterases, amidases, aldolases | • organic syntheses monoglycerides peptides | | Jones, J.B., Tetrahedron 42: 3351–3403.(1988) |
| • proteases, peptidases | | | Butt, S. and Roberts, S.M., Natural Product Reports 489–503 (1986), and references cited |
| • yeast lipase | • 2(p-chlorophenoxy) propionic acid: herbicide | resolution of racemic ester | therein for a more comprehensive review of this area |
| • strictodine synthetase | • alkaloid production eg strictosidine | | Pfitzner et al., Methods in Enzymology 136: 342 (1987) |
| • penicillin acylase | • 6-amino penicillinanic acid and 7-ADCA | penicillin G or, V | Enz Eng 6: 291 (1982) |
| • penicillin amidase | | | Enz Eng 8: 155 |
| • hydroxysteroid dehydrogenases | • steroid transformations | | Carrea et al, Methods in Enzymology 136: 150(1987) |
| • 5'phosphodiesterase, nucleases | • 5'-ribonucleotides | | Keller et al, Methods in Enzymology 136: 517 (1987) |
| • esterase | • β-lactam precursor (chiral mono esters eg βamino glutaric acid monoalkyl ester) | corresponding diesters | Japanese patent application: 82–159, 493 (1981) Biseibutsu Company |
| • lipases | • β-blockers | | Kloosterman, M et al., Trends in Biotechnology 6: 251–256 (1988) |

Production of Acrylamide Using CLEC Technology

The following is a description of one use of the method of the present invention: the adaptation of acrylamide production from immobilized cells which overproduce nitrile hydratase enzyme (Nagasawa, T. and Yamada, H., Trends in Biotechnology 7: 153–158 (1989)) to the CLEC technology previously disclosed herein.

Industrial scale production of acrylamide, an important commodity chemical, has been described by Yamada and collaborators (Nagasawa, T. and Yamada, H., Trends in Biotechnology 7: 153–158 (1989)). Kilotons of acrylamide per year are produced in chemical reactors loaded with entrapped cells selected as overproducers of the enzyme nitrile hydratase. Nitrile hydratase has also been reported as purified and crystallized from two sources, Brevibacterium R312 (Nagasawa et. al., Biochem. Biophys. Res. Commun. 139: 1305–1312 (1986) and P. chlororaphis B23 (Nagasawa et. al., Eur. J. Biochem. 162: 691–698 (1987). As disclosed here, these crystalline enzymes can each be immobilized by crosslinking with glutaraldehyde or other suitable crosslinking reagent to produce a CLEC. The nitrile hydratase CLECs can then be used in a conventional reactor, in place of the entrapped cells currently used. Adapting this process to CLEC technology leads to immediate advantages. These include; reduced plant size and improved throughput resulting from the enhanced activity per unit volume implicit in the higher enzyme concentration in the CLECs, and improved substrate and product diffusion rates; reduction in undesired contamination and side reactions, resulting from the higher purity of CLECs; and reduced sensitivity to microbial contamination in the absence of cells. In addition, there are other benefits available only to a CLEC-based method. These benefits include: higher temperature operation to improve reaction rates; the ability to operate in aqueous, organic and near-anhydrous solvents, allowing optimization of the acrylamide production reaction; and enhanced half-life in operation and storage, resulting from the higher chemical and mechanical stability of CLECs, particularly in unconventional solvents.

Medical Applications of CLEC Technology

The method of the present invention and an appropriately selected CLEC or set of CLECs can also be used for medical applications. A CLEC or a set of CLECs can be used, for example, to remove a component of a fluid, such as blood, generally by altering the component, and thus, converting it to a substance not detrimental to an individual or which can be removed by normal body processes (e.g., via detoxification, or degradation in the liver, excretion via the kidneys). In this application, an appropriately-selected CLEC or set of CLECs is brought into contact with body fluid, which contains the component to be altered, or a reactant (product or substrate) of a reaction in which the component participates, upon which the enzyme in the CLEC acts. As a result, the enzyme is able to act upon the component to be altered or with another substance which is a product of a reaction in which the component to be altered participates. The activity of the enzyme results in direct alteration of the component to be removed or in alteration of the product of the reaction in which the component participates (thus making continuation of the reaction impossible). This can be carried out through the use of an extracorporeal device which includes an appropriately-selected CLEC or set of CLECs and a retaining means which is made of a material; such as a porous material on which a CLEC is retained or a tube in which a CLEC is present, which allows contact between the component itself or the substance in the fluid which is a product of a reaction in which the component to be altered participates.

This might also be achieved by the insertion of an appropriate CLEC into a suitable body compartment, such as the peritoneum or a lymph node, where the CLEC would have access to bodily fluids. This insertion might be done surgically, or by injection of the CLEC slurry. Direct injection of CLEC into the blood stream would not be appropriate, given the high risk of embolism.

The use of appropriate CLECs in this area might serve as an alternative to genetic methods in enzyme replacement therapy to correct a natural deficiency, such as, e.g. phenylketonuria.

Table 3 illustrates some of the medical applications in which CLECs could be used. For the majority of these cases, the extra-corporeal treatment is still in the research phase, but the benefits that CLECs offer could provide novel treatments in areas in which there was previously no alternative treatment.

blood by employing a heparinase device at the effluent of the extracorporeal device which eliminates all heparin from the blood returned to the patient and thus avoids the current problems of heparinization.

Published research (Langer et al. Science 217: 261–263 (1982)); Bernstein et al., Methods in Enzymology 137: 515–529 (1987)), details the problems presented by conventionally immobilized enzymes used in extracorporeal devices. The principal problem is that conventional immobilization results in a low retention of enzyme activity per unit volume, thus requiring a large volume of immobilized enzyme to perform the necessary heparinization. This volume is too large to be of practical use in humans. However, the high retention of activity per unit volume in CLECs, due to the lack of inert support circumvents this problem and offers a practical solution to deheparinization of humans. The enhanced stability of CLECs will reduce the disassociation of enzyme from the crosslinked crystal. This is superior to the less stable, conventionally immobilized

TABLE 3

| Enzyme employed | Removal of:- | Disease/patients treated | References |
|---|---|---|---|
| • asparaginase | • asparagine | • leukemia (Removal of asparagine, an important cancer nutrient, harms leukemic cells which cannot manufacture the essential amino acid - asparagine; normal cells can manufacture asparagine and so are unaffected by this treatment.) | Klein, M., Langer, R., Trends in Biotechnology 4: 179–185 (1986) and references therein<br><br>Chang, T.M.S., Methods in Enzymology 137: 444–457 (1987) & references therein |
| • heparinase | • heparin | • deheparinization for hemoperfusion patients eg kidney dialysis | Langer, R., et al., Science 217: 261–263 (1982) |
| • bilirubin oxidase | • bilirubin | • neo-natal jaundice | Lavin, A., et al., Science 230: 543–545 (1985) |
| • carboxypeptidase | • methotrexate | • chemotherapy patients | Pitt, A.M., et al., Appl. Biochem. Biotechnol.8: 55–68 (1983) |
| • tyrosinase | • aromatic amino acids | • liver failure exhibiting pathological elevations of amino acids | Chang, T.M.S., Sem. Liver Dis.Ser. 6: 148 (1986) |
| • phenylalanine ammonium lyase | • phenylalanine | • phenylketonuria and liver failure | Ambrus, C.M., et al., J. Pharm. & Exp. Ther. 224: 598–602 (1983) |
| • multi-enzyme system including: urease, glutamate dehydro-genase, glucose, dehydrogenase & a transaminase | • urea (converted into glutamic and other amino acids, via ammonia) | • detoxification for chronic renal failure patients | Chang, T.M.S., Methods in Enzymology 137: 444–457 (1987) & references therein<br>Chang, T.M.S., Enzyme Eng 5:225 (1980) |
| • arginase | • arginine | • familial hyperargininaemia | Kanalas, J. J. et al, Biochem. Med. 27: 46–55 (1982) |
| • glutamate dehydrogenase & ammonia | • ammonia | • liver failure | Maugh, T.H., Science 223: 474–476 (1984) |

A particular application of the present method is the heparin lyase system for blood deheparinization (Bernstein et al., Methods in Enzymology 137: 515–529 (1987)), which is discussed below.

All extracorporeal devices perfused with blood, such as kidney dialysis, continuous arteriovenous hemofiltration or extracorporeal membrane oxygenators, require heparinization of the patient to avoid blood clotting. However, heparinization of the patient leads to hemorrhagic complications and remains a threat to human safety. These problems increase as the perfusion times increase, for example with the membrane oxygenator, and can lead to serious bleeding. After extracorporeal therapy, heparin may be removed from enzymes, because immune responses resulting from enzyme leakage will be reduced. CLEC temperature stability prevents denaturation of the enzyme due to high transient temperatures during storage; it is likely that CLECs may retain high activity, even when stored at room temperature. In addition, CLECs will be cheaper and more convenient to use than their conventionally immobilized counterparts because of their longer operational and storage lifetimes.

CLECs made by the present method can be used for additional medical purposes, both therapeutic and diagnostic. As described herein, enzymes which have potential for such uses have been crystallized and crosslinked and assessed as to their enzymatic activity and stability under various conditions. For example, lipase CLECs have been produced and shown to retain significant enzymatic activity. Such lipase CLECs can be used, for example, to treat individuals with pancreatic insufficiency and/or fat malasorption conditions, in which lipase secretion is abnormally low. This can be associated with steatorrhea, essential fatty acid deficiency, loss of a high calorie source (fat) or a fat-soluble vitamin deficiency. Presently available approaches to lipase supplementation have numerous shortcomings, which limit their effectiveness. For example, gastric acid inactivation of enzyme supplements or digestion by proteases of lipase-supplementation agents may occur, reducing the available amount of the agent(s) used. Possible supplementation strategies include high doses of pancreatic enzymes, use of pH sensitive enteric-coated microspheres and capsules, gastric acid modulation and use of acid resistant lipases (which presently are unavailable). Lipase CLECs can be used as therapeutic agents or drugs and, in this context, have several key advantages: they are stable to exogenous proteolysis, stable to pH levels which would inactivate or destroy other enzyme forms, stable to heat and solvents and easily stored because they can be lyophilized; as described herein. Other therapeutic uses include administration of or treatment with urease. CLECs and xanthine oxidase CLECs (e.g., in treating hyperuriocosuria, resulting in conversion, in the GI tract, of purines to uric acid, followed by excretion of the uric acid.

In therapeutic applications, design and use of CLECs which release the enzyme over time (e.g., slow or controlled release) might prove advantageous, such as to provide the activity over time or to delay its release (e.g., to allow the enzyme to pass through harsh pH conditions in the stomach by being protected in CLEC form and then being released). Production of CLECs in which crosslinking and/or crystallization is designed to permit slow or controlled release would provide useful agents.

Additional Applications of CLEC Technology: Biosensors

A CLEC or a set of CLECs can be used as a component of a sensor, referred to as a biosensor, useful for detecting and/or quantitating an analyte of interest in a fluid, such as body fluid (e.g., blood, urine), chemical and laboratory reaction media, organic media, water, culture medium and beverages. In some instances, the fluid in question can be a gas, as in an alcohol breath analyzer (Barzana, E., Klibanov, A., and Karell, M., NASA Tech Briefs 13:104 (1989)). In this application an appropriately-selected CLEC or set of CLECs is brought into contact with a fluid to be analyzed for the analyte of interest. The analyte of interest can be measured directly (e.g., blood glucose level) or indirectly (e.g., by detecting or quantitating a substance which is a reactant (product or substrate) in a reaction in which the analyte of interest participates). In either case, the CLEC is able to act upon the analyte or the substance which is a reactant in a reaction in which the analyte also participates. The activity of the enzyme results in a detectable change (e.g., change in pH, production of light, heat, change in electrical potential) which is detected and/or quantitated by an appropriate detecting means (e.g., pH electrode, light or heat sensing device, means for measuring electrical charge) (Janata, J., et al., Anal. Chem. 62: 33R–44R (1990)). Any means useful for detecting the change resulting from the enzyme-catalyzed method can be used. A biosensor of the present invention includes a CLEC or set of CLECs and a retaining means for the CLEC which allows contact between the CLEC(s) and the analyte of interest or the substance in the fluid which is a reactant in the reaction in which the analyte of interest participates.

Table 4 illustrates some of the biosensor applications in which CLECs could be used. Currently immobilized enzymes are used in these applications, but suffer from low stability, low enzyme density, short lifetimes and lack of reproducibility. These examples can be readily adapted to the CLEC technology disclosed here.

TABLE 4

| Enzyme Employed | Detection of:- | Application | Reference |
| --- | --- | --- | --- |
| • glucose oxidase | • glucose | • diabetics | • Daniles, B., Mossbach, K, Methods in Enzymology 137: 4–7 (1987)<br>• Hall,E "Biosensors" Open University Press (1990)<br>• Taylor, R., Proceed. Biotechnology Conference 1989; 275–287<br>• Anthony et al.,<br>• Biosensors, Fundamentals and Applications", Oxford University Press (1987) |
| • creatinine deiminase | • creatinine | • kidney function | • Tabata, M. et al., Anal. Biochem. 134: 44 (1983) |
| • urease | • urea | • kidney function | • Hsuie, G.H et al., Polym. Mater. Sci. Eng. 57: 825–829 (1987)<br>• Kobos, et al. Anal.Chem. 60: 1996–1998 (1988) |
| • lactate oxidase & dehydrogenase | • lactate | • clinical applications | • Blaedel, W.J. & Jenkins, R A., Anal. Chem. 48(8): 1240(1976)<br>• Sagaguchi, Y., et al., J. Appl. Biochem 3: 32 (1981) |
| • glucose-6-pyruvate dehydrogenase | • Glucose-6-phosphate, sucrose and ATP | • diabetics and other medical | • ibid as glucose oxidase |
| • alcohol dehydrogenase, alcohol oxidase | • ethanol & other alcohols; acetic, formic acids | • breathalysers and industrial applications | • Romette, J.L., et. al., Methods in Enzymology 137: 217–225 (1987) |

TABLE 4-continued

| Enzyme Employed | Detection of:- | Application | Reference |
|---|---|---|---|
| | | | • Ho, M.H., Methods in Enzymology 137: 271–288 (1987) |
| • β-fructosidase | • sucrose | • industrial applications | • Romette, J.L. et al., Methods in Enzymology 137: 217–225 (1987) |
| • cholesterol oxidase | • cholesterol | • cholesterol testing | • Satoh, I., Methods in Enzymology 137: 217–225 (1987) |
| • catalase | • uric acid, cholesterol | • atherosclerotic and other medical | • Satoh, I., Methods in Enzymology 137: 217–225 (1987) |
| • carboxy peptidase | • methotrexate | • cancer | • ibid as glucose oxidase |
| • carbonic anhydrase | • carbon dioxide | • industrial, laboratory & environmental applications | • ibid as glucose oxidase |
| • L-amino acid oxidase | • amino acids | • medical and industrial | • ibid as glucose oxidase |
| • β-lactamase penicillinase | • penicillin | • medical | • Anzai et al., Bull. Chem. Soc. Jpn. 60: 4133–4137 (1988) |
| • alkaline phosphatase | • phosphate | • metabolite monitoring | • ibid as glucose oxidase |
| • nitrate/nitrite reductase | • nitrates & nitrites | • metabolite and food monitoring | • ibid as glucose oxidase |
| • arylsulfatase | sulfate | • metabolite monitoring | • ibid as glucose oxidase |
| • succinate dehydrogenase | • succinate | • industrial | • ibid as glucose oxidase |
| • bacterial luciferase | $FMNH_2$ and coupled reactions | • detection of $10^{-18}$ molar quantities of $FMNH_2$ through measurement of photon release | • WannlundJ., et al., "Luminescent assays: Perspectives in endocrinology and clinical chemistry"; Eds Serio, M. and Pazzagli, M. I: 125 (1982)<br>• Kurkijarvi et al., Methods in Enzymology 137: 171–181 (1987) |
| • firefly luciferase | ATP and coupled reactions | • detection of $10^{-12}$ molar quantities of ATP through measurement of photon release | • Kurkijarvi et al, Methods in Enzymology 137: 171–181(1987)<br>• Murachi et al., Methods in Enzymology 137: 260–271 (1988) |

In the method of the present invention as it is carried out for the analysis of samples in a biosensor, it is particularly desirable to produce the largest possible detectable signal from the smallest possible quantity of substrate and catalyst. In this regard, the CLEC technology disclosed here is particularly attractive, since it achieves the highest possible concentration of enzyme catalyst in a given volume.

Often, considerable efforts are made to couple an ultimate enzymatic reaction of interest, either directly, or through suitable intermediates, to the production of light by enzymes like luciferase (Kurkijarvi et al., Methods in Enzymol. 137: 171–181 (1988)). This is done in order to take advantage of the unparalleled sensitivity and efficiency of photon detection equipment, which allows for the detection of femtomolar concentrations of enzyme reaction products under appropriate conditions. Following this principle, biosensor systems have been designed, using conventionally immobilized enzymes, to detect various substrates of clinical and other interest. Light producing reactions have been coupled to assay reactions detecting substrates like, D-glucose, L-lactate, L-glutamate and ethanol, among others, at extremely low concentration.

With regard to this application, the luciferase enzyme from Vibrio harveyii has been reported as crystallized (Swanson et al., J. Biol. Chem. 260: 1287–1289 (1985)). Crystals of this luciferase can be crosslinked with glutaraldehyde or other suitable reagent to form a CLEC of luciferase. For biosensor and analytical uses, a CLEC of luciferase offers many advantages over conventionally immobilized enzyme. In a CLEC, the entire volume of the luciferase CLEC would consist of light emitting enzyme. In a conventionally immobilized enzyme system, however, as much as 95% of the total volume is taken up by "inert" carrier material, which more likely functions as an absorber of the light emitted by enzyme. In addition, the enhanced stability of CLECs should facilitate storage at room temperature, and also makes possible novel sensing applications in harsh environments and elevated temperatures.

CLACs of the present invention should be useful for diagnostic and therapeutic purposes (e.g., delivery of an agent (such as a label or a cytotoxic agent) to a defined cell type (one recognized by the antibody).

Additional Applications of CLEC Technology—Laboratory Reactions

CLECs may be used as laboratory reagents in small columns or in batch processes, which can be used to carry out laboratory reactions. Some of the broad categories of reactions are in Table 5. In addition, appropriately selected antibodies, or antibody fragments (particularly monoclonal antibodies), which recognize process chemicals, clinical analytes, pesticides and other environmental residues can be turned into CLACs and used to selectively bind these substances, making their detection in and/or removal from a sample or other source possible. For example, a substance can be separated from a mixture by contacting the mixture with a crosslinked immobilized antibody crystal in which the antibody recognizes the substance, thereby producing a complex of the substance and the crystal, and separating from the mixture the resulting complex. The crosslinked crystal will generally be linked to a solid support, such as a column or a bead. For example, CLACs can be packed into an affinity column and a sample from which a selected component is to be removed can be run through the column resulting in binding of the component to the antibody and permitting its removal. This can be used, for example, on a small or a large scale to remove pesticides (e.g., Aldrin) from soil, water or other source. In this case, a pesticide binding monoclonal antibody CLAC is used in an affinity column or other appropriate structure. Because it is in CLAC form, the monoclonal antibody can withstand the harsh conditions used (e.g., organic solvents) and the antibody-bound pesticide is removed from the sample (e.g., by nature of the fact it is bound to antibody which is, itself, bound to a solid support, which can be separated from the sample.

experiments. Third, their high activity per unit volume will allow shorter reaction times and require smaller volumes of enzyme (per unit of activity). Thus, the advantages that CLECs offer over free or immobilized enzymes, provide organic chemists with an alternative, highly selective, synthetic tool.

Enzymes are catalytic proteins that make possible or greatly accelerate almost every biologically important chemical reaction. Enzymes perform oxidations, reductions, additions, eliminations, rearrangements, hydrolyses, dehydrations. They are thus responsible for manufacturing every biologically significant molecule in plants and animals, from sub-cellular organelles to bones and organ systems. Because an enzyme typically carries out one chemical step at a time in what may be a complex, multistep transformation (requiring twenty or more enzymes), chemists have for decades been intrigued by the potential for using enzymes as synthetic chemical catalysts.

Despite the great potential for using enzymes in synthetic chemistry, their utility outside living systems has been hampered by seemingly insurmountable problems:

TABLE 5

| Enzyme Employed | Reaction type catalyzed | Reference |
| --- | --- | --- |
| • lipases, phospholipases | • Stereoselective synthesis: including esterification, transesterification, aminolysis, lactonizations, polycondensations, acylation, oximolysis and resolution of racemic mixtures | • Zaks, A. & Klibanov, A.M. Proc. Nat. Acad. Sci. USA. 82: 3192–3196(1985)<br>• Klibanov, A.M. Acc. Chem. Res. 23: 114–120 (1990) and references therein<br>• Wong, C.H., Chemtracts-Organic Chemistry 3:91–111 (1990) and references therein |
| • esterases | • stereoselective synthesis and resolution | • Kobayashi et al., Tetrahedron Letters Vol 25, #24: 2557–2560(1984)<br>• Schneider et al., Agnew. Chem. Int. Ed. Engl. 23 (#1): 64–68 (1984) |
| • tyrosinase | • oxidation of phenols to produce quinones | • Kazandjian, R.Z and Klibanov, A.M. J. Am. Chem. Soc 110: 584–589 (1986) |
| • proteases, eg subtilisin | • stereoselective acylation of carbohydrates | • Riva et al. J. Am. Chem. Soc. 110: 584–589(1988) |
| • oxidases | • selective oxidation of hydrocarbons | • Klibanov, A.M. Acc. Chem. Res. 23: 114–120(1990) and references therein |
| • other enzymes not requiring co-factors: isomerases, lyases, aldolases, glycosyl transferases, glycosidases | • Stereoselective synthesis: | • Wong, C.H., Chemtracts-Organic Chemistry 3:91–111 (1990) and references therein |
| • other enzymes not requiring added co-factors: flavoenzymes, pyridoxal phosphate enzymes, metalloenzymes | • Stereoselective synthesis: | • Wong, C.H., Chemtracts-Organic Chemistry 3:91–111 (1990) and references therein |
| • enzymes requiring co-factors: kinases (ATP), oxidoreductatses (NAD/P), methyl transferases (SAM), CoA-requiring enzymes, sulfurases (PAPS) | • Stereoselective synthesis: | • Wong, C.H., Chemtracts-Organic Chemistry 3:91–111 (1990) and references therein |

Schneider et al. (Agnew. Chem. Int. Ed. Engl. 23 (No. 1): 64–68 (1984)) illustrates how enzymes may be used in organic syntheses. Pig liver esterase was employed in the meso-ester transformation into a chiral mono-ester in an aqueous phosphate buffer.

The advantages of CLEC catalyzed reactions for laboratory use are threefold. First, CLECs retain high activity in harsh environments (eg. aqueous, organic, near-anhydrous solvents and mixtures of these, and at high temperatures) that are typical of laboratory chemical synthesis experiments. Second, CLECs exhibit high operational and storage stability, which is appropriate for intermittent laboratory Isolation and purification of enzymes is difficult Enzymes are susceptible to degradation or inactivation by air, changes in pH, other enzymes, and organic compounds such as solvents The cost of enzymes and their chemical cofactors (small molecules required for enzymatic action) is high Relatively little is known about the interactions between enzymes and organic molecules which are not their natural substrates Fortunately, biotechnology is beginning to solve problems associated with isolation, purification, and cofactor regeneration, and innovative chemists are compiling data almost daily on adapting known enzymes to new substrates. However, the instability of enzymes and their aversion to solvents other than water have remained barriers to widespread use of these proteins in routine organic synthesis.

A CLEC (cross-linked enzyme crystal) contains more than one protein molecule organized in a crystalline lattice, which is either crosslinked or not crosslinked, or crosslinked by simple bifunctional organic molecules. A typical crosslinking agent, glutaraldehyde, contains two sites for attaching free amino groups found on proteins. As long as the amino group that attaches to glutaraldehyde is far from the enzyme's active site, crosslinking has no appreciable effect on enzymatic activity. After forming, the CLEC may be freeze-dried, air dried or left in a liquid state. In any of these storage conditions they may be stored indefinitely as a solid at room temperature. But most importantly, CLECs retain their high activity in real-world chemical reaction conditions, including harsh temperatures and pH, in many types of organic or mixed aqueous/organic solvent, and even in the presence of other enzymes that digest proteins.

Since so many industrial applications of enzymes depend on the molecule's stability and activity in sub-optimal conditions, CLECs will greatly expand the use of industrial and research enzymes, as well as non-enzyme proteins and a wide range of peptides. CLECs replace many conventional enzymes in applications where soluble or immobilized enzymes are already used, as well as in new applications where they cannot be used, e.g., in organic solvents or in mixed solutions of water and non-polar or polar organics, such as acetone, dioxane, acetonitrile, and tetrahydrofuran. Some potential chemical uses of CLECs in industry and research include:

Organic synthesis of important high-value intermediates and specialty chemicals.

Chiral synthesis and resolution for optically pure pharmaceuticals and specialty chemicals.

Bioprocessing of products produced through fermentation, as well as natural products harvested from plants, animals, and insects.

But CLEC technology is not just for enzymes. It is a general method for achieving unprecedented stability and activity in almost any protein and in smaller peptides. The most exciting applications of CLEC technology may arise not from chemical catalysis in the laboratory, but in therapeutics and diagnostics—both enzymatic and non-enzymatic—in the human body, tissues, or fluids.

There is considerable interest among pharmaceutical companies in proteins, protein fragments, and synthetic peptides as drugs and diagnostics. More and more drugs in research and development are peptides or "peptide-like" synthetic organic compounds. The trouble with peptides and peptide-like compounds—whether they are natural or synthetic—is stability. The human body contains thousands of proteolytic enzymes (proteases) that break down proteins and peptides into smaller and smaller units. Because of degradation by proteases, some peptides with potential therapeutic or diagnostic benefit have biological half-lives that are too short to enable them to work. Pharmaceutical scientists try to circumvent degradation of synthetic or semi-synthetic peptides by masking them with chemical groups that confer some protection from proteases. Unfortunately, because of strict requirements for chemical structure and molecular shape in biochemical interactions, the use of chemical protecting groups tends to lower a drug's affinity for target molecules or receptors.

Applied to non-enzymatic peptides and proteins, CLEC technology can produce therapeutic and diagnostic compounds with unprecedented in vivo stability and near-theoretical activity. Crosslinking may allow drug researchers to use native proteins or peptides and may eliminate the need, in certain instances, for designing structural analogues or implementing masking strategies to make drugs more resistant to degradation. Some potential medical uses of CLECs (or CLEC technology) include:

Therapeutic antibodies that bind to and inactivate viruses, bacteria, or proteins; antibodies against inflammatory mediators and mediators of nerve and tissue destruction; antibodies to messenger chemicals in conditions such as Alzheimer's disease, stroke, nervous system trauma, and autoimmune diseases; catalytic antibodies, which react with their immunologic targets after binding to them.

Diagnostic antibodies that bind to their targets to allow detection in vitro or in vivo.

Therapeutic proteins and enzymes that replace proteins absent due to acute, chronic, or inherited diseases; enzymes that dissolve blood clots or cholesterol deposits.

"Super-Inhibitors" of enzymes, receptors, or small molecules made from fragments of naturally-occurring inhibitor molecules or even from synthetic peptides.

Radiology: Proteins or peptides connected to radioactive elements for medical diagnostics (imaging) and therapeutics (radiotherapy); combined radiotherapy/imaging.

Enzyme therapy for cancer nutrient deprivation, pancreatic insufficiency, and other enzyme or protein therapies which, by the use of an enzyme or a protein results in the elimination of an adverse health state, and extracorporeal treatment (in which blood, lymph, or other tissues are removed from the patient, treated, and re-introduced).

Oral peptide drug delivery —conventional peptide drugs are quickly broken down in the gut, mostly by proteases. The improved stability of CLECs toward proteolysis may make these compounds attractive alternatives to intravenously administered peptide and peptide-like drugs.

Other important applications of CLECs include biosensors. Biosensors include many types of devices and technologies that detect and quantify biologically important events. For our purposes, however, biosensors are immobilized molecules connected to some type of signal transducer—either optical, electrical, electromagnetic, or chemical—that produce a signal in the presence of an analyte biomolecule. Many biosensors simply detect the presence (or absence) of an analyte. More sophisticated sensors also quantify the amount of the analyte. Commercially available antibody-based biosensors are based on antibody-antigen interactions, one of the most specific chemical interactions known between two molecules.

Antibody-based biosensors have the same problems as other technologies based on purified enzymes: reduced operational and storage stability, vulnerability to contamination, and susceptibility to degradation when used in living tissues or on bodily fluids. Other technical hurdles to enzyme biosensors include difficulty in miniaturization, integration of a biomolecule and transducer, contamination and cross-reactivity.

CLEC technology for biosensors and diagnostics is applicable to enzyme antibodies, catalytic antibodies and other reaction proteins. These products may include:

Agricultural testing for pesticides, parasites, toxins, drug residues, and food composition.

Environmental monitoring and control

Medical and veterinary diagnostic tests for home, clinics, hospitals, clinical laboratories, and physician offices.

Industrial process monitoring, primarily in biotechnology

Real-time monitoring and sensing for research and therapy using animals, tissues, or cells.

CLECs offer many advantages over non-crosslinked enzymes. These advantages also hold for non-enzymatic proteins, and perhaps for smaller peptides as well:

Superior Stability—The intermolecular contacts and crosslinks between enzymes in the crystal lattice of a CLEC stabilize the enzyme and prevent denaturation. CLECs remain active and are resistant to proteolysis, extremes of temperature, and organic solvents. CLECs are stable at room temperature indefinitely.

Solid Form—Soluble enzymes require immobilization in most applications. CLECs, which can be either soluble or insoluble enzyme particles, eliminate the need for an inert support.

Highest Possible Concentration—the activity, per unit volume, of CLECs is significantly higher than that of conventionally immobilized enzymes or concentrated soluble enzymes. Enzyme concentrations within a CLEC are close to theoretical limits.

Superior Uniformity—As crystals, individual CLEC particles are uniform and monodisperse, in contrast to undefined, and often random attachment of conventional enzymes. CLECs remain monodisperse on reconstitution, even in organic solvents.

Operational Convenience—CLECs can easily be freeze-dried or air dried and, in that form, can be stored indefinitely at room temperature.

CLECs have special advantages over soluble or conventionally immobilized enzymes for bioprocessing, including:

Improved yield under harsh conditions or situations requiring high throughput, enabling process chemists to concentrate on maximizing yield with less concern about reaction conditions.

Cleaner, faster reaction—Because they are not soluble, CLEC enzymes can be easily separated from the product via settling or filtration, thereby eliminating a source of contamination.

Longer catalyst life and faster reaction times.

Environmentally benign—biocatalysts are easier to dispose of than most synthetic catalysts.

Mechanical strength—allowing continuous flow rather than batch processes.

As biosensors, CLECs have all the advantages of immobilized enzymes and none of the drawbacks:

High specificity, sensitivity, and accuracy.

Extended operational lifetime and storage stability.

Miniaturization—Since CLECs are insoluble crystals, they do not require an inert carrier and exhibit the highest protein density possible. The high specific activity means a CLEC will generate the largest possible signal from even the smallest substrate (analyte) concentration.

Uniform Signal—Proteins in crystal form are uniformly arranged. This uniformity should produce a linear and predictable signal.

Resistance to Contamination—Soluble enzymes are vulnerable to proteolysis as well as contamination in many biosensor environments. Since CLECs are crystalline they are less susceptible to contamination and may be reused with minimum effort.

CLECs will have a primary impact on companies involved in industrial and research enzymes, medical therapeutics and diagnostics, and biosensors. These firms will now be able to direct their research efforts toward producing biocatalysts, drugs, and other products with less concern for the stability of their molecules and more concern for function.

Most CLECs retain nearly 100% of the activity of soluble enzymes after two weeks or more in conditions that denature soluble proteins within hours. Improvements in efficiency and throughput per weight of protein can therefore easily reach a hundred-fold or more. That may mean, in the short term, selling less of an enzyme or antibody compared to the soluble form. However, the improved performance of CLECs may expand the commercial potential for proteins as much as ten-fold for existing applications, and thousands of times for as-yet undiscovered uses.

CLEC technology will cause pharmaceutical and specialty chemical manufacturers to re-think the catalytic potential of many enzyme processes (and non-enzyme proteins and peptides) that may have been shelved due to the low efficiency of idealized soluble or supported proteins, the high cost of multi-phase reactions, or difficulties in product isolation or biocatalyst removal.

Pharmaceutical companies concerned about the in vivo proteolysis or unacceptable biological half-life of protein or peptide therapeutics can now focus on pharmacologic activity rather than on masking peptide bonds from circulating degrading enzymes.

Of course, some proteins may not have free primary amine groups to combine with glutaraldehyde. In others, the free amines may be too close to the active site or may be required to retain tertiary structure necessary for activity. So although the prototype CLEC uses glutaraldehyde conjugated with primary amines, this approach may not be appropriate to every protein, enzyme, antibody, or peptide. For these molecules, other suitable crosslinkers can be employed.

In general, CLECs will greatly expand the uses of industrial proteins, especially enzymes and antibodies. It is difficult to pinpoint, from this vantage point, the improvement in efficiency required to make a run-of-the-mill peptide interesting scientifically. Predicting which molecules will turn a profit is even more difficult, especially in highly regulated healthcare fields. However, with hundred-fold improvements in protein stability easily attainable via crosslinking, CLECs will resurrect thousands of peptide research programs and greatly expand the scope of currently successful research efforts.

Computer databases of proteins and peptides might lead to a nearly limitless supply of leads for crosslinking, resulting in dozens or hundreds of new products. Modifying refractory proteins through residues containing sulfhydryl or hydroxyl groups might be another way to crosslink proteins that are poor candidates for joining through free amine groups.

Other applications can include, for example, deposition of crystallized enzymes, proteins, peptides, or amino acids on an inert substrate. Also, coating can be formed over crystallized amino acid chains by crosslinking any outer portion of the crystals with a suitable crosslinking agent, such as an aldehyde or an oligomer of the aldehyde. An example of a suitable aldehyde is glutaraldehyde.

In all of these instances described above, but not limited to these, the method of this invention can be adapted by one of ordinary skill in the art, to convert a process using a conventionally immobilized enzyme catalyst to the use of a CLEC of the appropriate enzyme. CLECs can not only replace conventional immobilized enzymes, but can also be used in cell mediated transformations.

The present invention will now be illustrated by the following Examples, which are not intended to be limiting in any way.

EXAMPLE 1

Crystallization and Crosslinking of Thermolysin for Synthesis of the Aspartame Precursor, Z—Asp—Phe—Ome Crystallization 250 mg of thermolysin from *Bacillus thermoproteolyticus* was purchased from Boehringer-Mannheim GmbH, and dissolved in 4 ml of 45% dimethyl sulfoxide (DMSO) and 55% 1.40M calcium acetate, 0.50M sodium cacodylate at pH 6.5. These starting conditions are similar to those described by Matthews et. al. for the production of diffraction quality thermolysin crystals (see, eg., Holmes and Matthews, J. Mol. Biol. 160: 623–639 (1982)). The protein solution was then concentrated to 1 ml in a Centricon 10 micro-concentrator. A good yield of microcrystals was obtained by a process of flash crystallization, now disclosed here, in which 1 ml of water, or 1.40M calcium acetate, 0.50M sodium cacodylate at pH 6.5, was rapidly injected into either of the thermolysin-DMSO solutions described above. A shower of hexagonal micro-crystals of approximately uniform dimensions (approx. $10^{-1}$ mm in length) results from this process.

Crosslinking of Thermolysin Microcrystals

The protocol used in this specific example of the method of this invention is an adaptation of that described by Nakanishi et. al. (Biotechnology 3: 459–464 (1985)), in which protocol, thermolysin was first adsorbed onto a carrier bead composed of the ion-exchange resin Amberlite XAD-7, and subsequently immobilized by cross-linking with glutaraldehyde (Quiocho and Richards, Proc. Natl. Acad. Sci. (USA) 52:833–839 (1964)). In this exemplification, the microcrystals of thermolysin obtained above were centrifuged and pelleted, and the supernatant was discarded. 5 ml of 17.5% technical grade glutaraldehyde, in 2.5 % DMSO, 0.05M calcium acetate, and 0.025M sodium cacodylate at pH 6.5, were then added to the microcrystals. The mixture was incubated with gentle agitation at 37° C. for 4 hours. The crosslinking reaction was stopped by repeated washing of the crystals with 10 ml aliquots of water to remove the glutaraldehyde solution. The washed cross-linked thermolysin crystals constitute the thermolysin CLEC used below as a catalyst.

Synthesis of Z—Asp—Phe—OMe in an Aqueous Solution 5 ml of a thermolysin CLEC suspension were added to a continuous stirred-batch reactor incubated at 37° C. After centrifugation and decantation of the supernatant, an aqueous reaction mixture was added to the CLECs. This solution was prepared by mixing 80 mg of Z—L—Asp and 80 mg of L—Phe—Ome—HCl in 1 ml of water, with acetic acid added to obtain a pH of 7.0. Samples were taken for analysis by HPLC. Table 6 below shows the HPLC peak height of the Z—L—Asp substrate peak after the indicated time of reaction, normalized to 1 at time t=0. Since Z—L—Asp is rate limiting in this reaction, measuring its depletion is equivalent to measuring the appearance of product Z—L—Asp—L—Phe—OMe (Nakanishi et. al. Biotechnology 3: 459–464 (1985)). Table 6 also includes the normalized peak height of limiting Z—L—Asp substrate remaining, and an estimate of the degree of completion of the reaction. It is clear that the reaction proceeded to about 20% completion within the first 30 seconds and plateaued there. These results are consistent with the observations of Nakanishi et al. (Biotechnology 3: 459–464 (1985)) when using conventionally immobilized thermolysin in an aqueous reaction mixture as above, and are attributable to the sparing solubility of the Z—L—Asp—L—Phe—OMe product in water.

TABLE 6

| Reaction Time (sec) | Peak Height (Normalized) | Percent Completion |
|---|---|---|
| 0 | 1.000 | |
| 30 | 0.727 | 27.3% |
| 60 | 0.857 | 14.3% |
| 120 | 0.940 | 6.0% |
| 180 | 0.797 | 20.3% |

Synthesis of Z—Asp—Phe—OMe in a Near-anhydrous Solution 5 ml of a thermolysin CLEC suspension were added to a continuous stirred-batch reactor incubated at 37° C. After centrifugation and decantation of the supernatant, a near-anhydrous organic reaction mixture was added to the CLECs. This solution was prepared by mixing 80 mg of Z—L—Asp and 240 mg of L—Phe—OMe in 1 ml of 99% ethyl acetate and 1% water. Samples were taken for analysis by HPLC. Table 7 below shows the HPLC peak height of the Z—L—Asp substrate peak after the indicated time of reaction, normalized to 1 at time t=0. Since Z—L—Asp is rate limiting in this reaction, measuring its depletion is equivalent to measuring the appearance of product Z—L—Asp—L—Phe—OMe (Nakanishi et. al. Biotechnology 3: 459–464 (1985)). Table #7 also includes the normalized peak height of limiting Z—L—Asp substrate remaining, and an estimate of the degree of completion of the reaction. In this case, the reaction proceeded to about 70% completion within the first 30 seconds and plateaued there. These results are also consistent with the observations of Nakanishi et al. (Biotechnology 3: 459–464 (1985)) with conventionally immobilized thermolysin in a near-anhydrous reaction mixture, and are attributable to product inhibition of the enzyme.

TABLE 7

| Reaction Time (sec) | Peak Height (Normalized) | Percent Completion |
|---|---|---|
| 0 | 1.000 | |
| 30 | 0.323 | 67.7% |
| 60 | 0.314 | 68.6% |
| 120 | 0.305 | 69.5% |
| 180 | 0.272 | 72.8% |

EXAMPLE 2

Crystallization, Cross-Linking and Lyophilization of Thermolysin and Assessment of Characteristics of Resulting Product Crystallization of Thermolysin Thermolysin (Diawa Kasei K. K., Japan) was dissolved in 10 mM calcium acetate (Sigma), pH 10.0, to a concentration of 10% (w/v). The pH of the solution was maintained at 10.0 by titration with 2M NaOH. Following complete solubilization, the protein solution was titrated to pH 8.0 with 2M HCl. Solid calcium acetate was added to 1.2M. Dimethyl sulfoxide (Sigma) was then added to 30%. The protein was concentrated to 100 mg/ml by ultrafiltration in an Amicon stir cell (10,000 MWCO membrane). Concentrated enzyme was aliquoted and stored at −70° C. Thermolysin was crystallized by the addition of 9 volumes demineralized water to 1 volume concentrated (100 mg/ml) protein solution. The solution was briefly vortexed and allowed to stand overnight at room temperature. Crystals were washed with 10 volumes of 10 Mm calcium acetate pH 7.0 and recovered by low speed centrifugation (10 min at 1500×G, Beckman GPR centrifuge).

The rapid addition of water to a concentrated (100 mg/ml) solution of thermolysin induces the formation of crystals which become visible under low-power magnification within ten minutes. Crystal size is reproducibly dependent on the final protein concentration. Three volumes of water to one volume of thermolysin concentrate (100 mg/ml) will produce 0.5 mm long, X-ray diffraction quality hexagonal rods that correspond to the crystals described earlier by Colman et al. (Colman, P. M., Jansonius, J. N. and Matthews, B. W., J. Mol. Biol. 70: 701–724 (1972)), as confirmed by us by diffraction analysis. Adding ten volumes of water to one of protein concentrate reduces the length of the resulting crystals to 0.05 mm. These micro-crystals are preferred in CLEC applications, since they tend to minimize diffusion problems related to crystal size (see eg., Quiocho, F. A. and Richards, F. M. Biochemistry 5: 4062–4076 (1967)). Within a given batch of protein, crystal size was consistently uniform. (Crystals 0.05–0.10 mm in length were used in this study to facilitate accurate pipetting of crystalline suspensions.) Densitometer scans of SDS-PAGE showed a six-fold purification of the enzyme on crystallization, significantly increasing the specific activity of the CLECs. Crystallization resulted in a 20% decrease in the total activity of the CLEC protein compared to soluble thermolysin, when assayed by spectrophotometric cleavage of the dipeptide substrate furylacryloyl-glycyl-L-leucine-amide (FAGLA), as described below.

Crosslinking of Thermolysin Crystals

Thermolysin crystals were crosslinked for 3 hours at room temperature in a solution of 12.5% glutaraldehyde (Sigma), 5% DMSO and 50 mM Tris pH 6.5. The crosslinked crystals were washed 3 times in demineralized water and recovered by low speed centrifugation, as described in respect to crystallization of thermolysin. Chemical cross-linking of enzyme crystals stabilizes the crystal lattice and the constituent enzyme molecules in the crystal sufficiently so as to permit the practical use of CLECs in environments that are otherwise incompatible with enzyme function. There was no measurable difference in enzymatic activity between the crosslinked and un-crosslinked crystals when assayed (spectrophotometrically) by monitoring cleavage of the dipeptide substrate FAGLA (described below). Moreover, crosslinking stabilizes CLECs to the point that they can be lyophilized, with retention of full enzymatic activity upon reconstitution in aqueous, organic, and mixed aqueous-organic solvents as shown in FIG. 1 and Table 8. Although crystallization resulted in a 30% decrease in the specific activity of the CLEC protein compared to soluble thermolysin, crosslinking and lyophilization of the CLECs did not further diminish specific activity.

TABLE 8

Thermolysin Activity

| | | Absorbance 345 nm | |
|---|---|---|---|
| | Time (min) | CLEC | Soluble Enzyme |
| 1 | 0.0 | 0.314 | 0.315 |
| 2 | 1.0 | 0.272 | 0.271 |
| 3 | 3.0 | 0.235 | 0.218 |
| 4 | 5.0 | 0.204 | 0.198 |
| 5 | 10.0 | 0.184 | 0.185 |
| 6 | 15.0 | 0.183 | 0.184 |

Enzymatic Activity of Soluble and CLEC Thermolysin

The catalytic activity of soluble and CLEC thermolysin was assayed (Feder, J. and Schuck, J. M., Biochemistry 9: 2784–2791 (1970)) by hydrolysis of the blocked dipeptide substrate furylacryloyl-glycyl-L-leucine-amide (FAGLA) (Schweizerhall). Cleavage of the amide bond was measured spectrophotometrically by a decrease in absorbance at 345 nm. Initial enzyme concentration was $10^{-7}M$ by Bradford protein determination and densitometer scanning (Pharmacia LKB UltroScan XL) of Coomassie stained SDS-PAGE gels. CLEC enzyme is defined as reconstituted lyophilized crosslinked thermolysin crystals. Soluble enzyme is defined as thermolysin concentrated to 100 mg/ml. Enzyme was added to a 5 ml reaction volume containing substrate. Aliquots of the reaction mix were removed at the indicated times, and absorbance at 345 nm was measured. CLEC thermolysin was separated from the reaction mix by brief centrifugation (Beckman, microcentrifuge E) before reading absorbance. Absorbance was fitted to a pseudo first order rate equation and kcat/Km was calculated by dividing the fitted value by enzyme concentration (Multifit 2.0 Curve Fitting for the Apple Macintosh Computer, Day Computing P.O. Box 327, Milton, Cambridge CB4 6WL, U.K. (1990)).

pH Dependence and Stability

Figure 2:
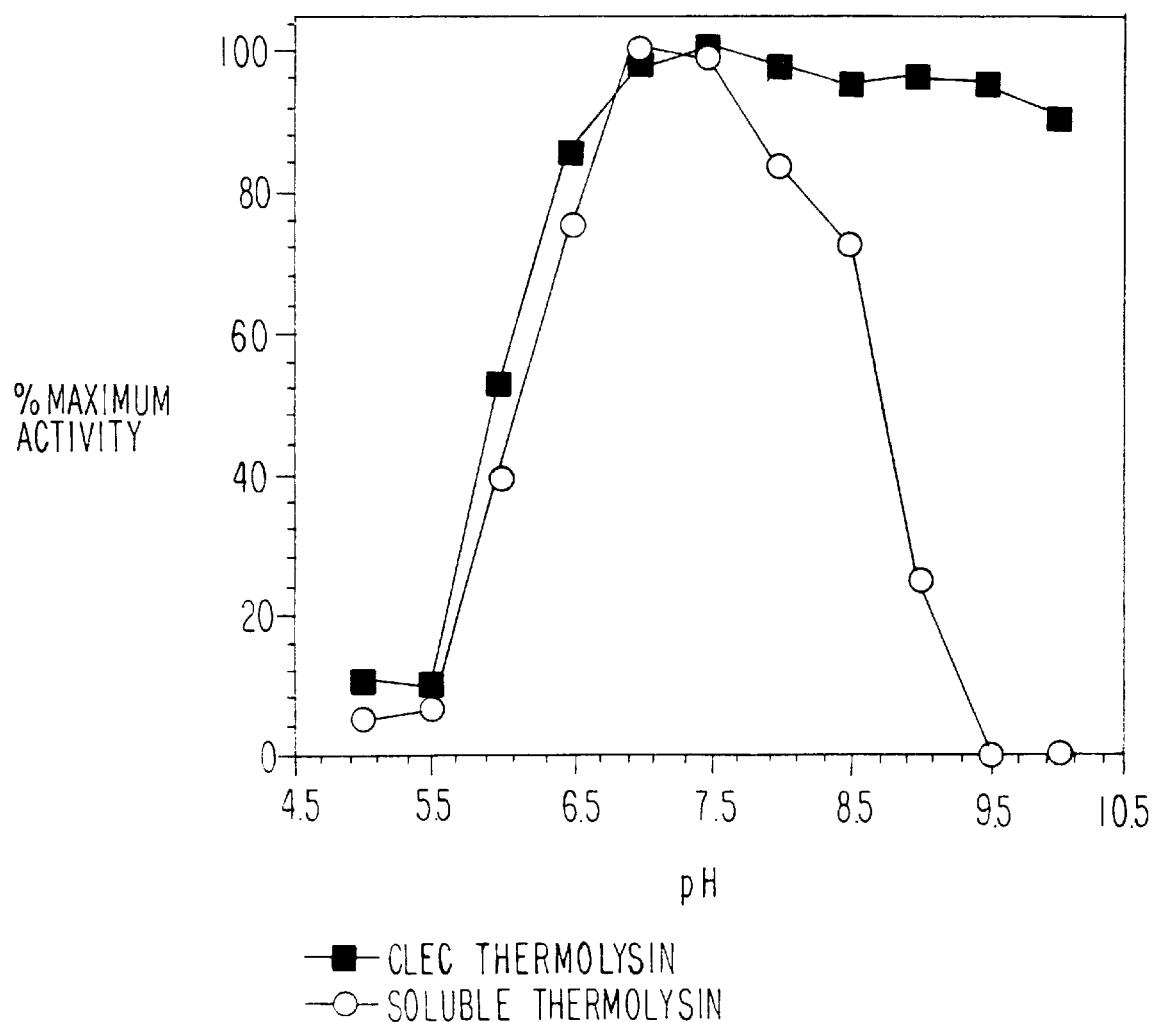
FIG. 2 is a graphic representation of results of a comparison of pH dependencies of thermolysin CLEC and soluble thermolysin.

The pH optimum and stability of the soluble enzyme were compared to that of thermolysin CLECs by cleavage of the dipeptide substrate FAGLA. Results are shown in FIG. 2 and Table 9. Both soluble and crystalline enzyme forms demonstrate maximum activity at pH 7. CLECs and soluble thermolysin also demonstrated similar activity in the acidic range and the bell shaped pH profile generated by the soluble enzyme was in good agreement with published data (Feder, J. and Schuck, J. M., Biochemistry 9: 2784–2791 (1970)). In the alkaline pH range, however, the crystalline enzyme maintains maximum activity, to pH 10, while the soluble enzyme has 75% activity at pH 8.5, and only 25% activity at pH 9. At pH 9.5, the soluble enzyme is completely inactive.

TABLE 9

Thermolysin pH Curve

| | | % Maximum Activity | |
|---|---|---|---|
| | pH | CLEC | Soluble Enzyme |
| 1 | 5.0 | 10.250 | 5.170 |
| 2 | 5.5 | 9.750 | 6.070 |
| 3 | 6.0 | 52.500 | 39.100 |
| 4 | 6.5 | 85.000 | 74.610 |
| 5 | 7.0 | 97.500 | 100.00 |
| 6 | 7.5 | 100.000 | 98.650 |
| 7 | 8.0 | 97.500 | 82.920 |
| 8 | 8.5 | 95.000 | 71.910 |

TABLE 9-continued

Thermolysin pH Curve

% Maximum Activity

| pH | | CLEC | Soluble Enzyme |
|---|---|---|---|
| 9 | 9.0 | 96.250 | 24.720 |
| 10 | 9.5 | 95.000 | 0.000 |
| 11 | 10.0 | 90.000 | 0.000 |

Stability at Elevated Temperature

One can achieve higher reaction rates and lower diffusion times for substrates and products by operating a given chemical process at higher temperature, where one is usually limited by the temperature stability of substrates and products. In enzyme-based catalysis, however, it is often the loss of enzymatic activity that sets the practical limit on the temperature that a process can be run. The additional stabilization achieved in CLECs allows for enzymatic activity at much higher temperatures than is possible for soluble enzyme.

The enhanced stability at lower temperatures simplifies the routine long term storage of the CLEC catalysts. For example, it was necessary to store concentrated (>50 mg/ml) solutions of soluble thermolysin at −80° C. to retain maximum specific activity. At room temperature, activity was usually lost within one day. In contrast, rehydrated thermolysin CLECs could be routinely stored for months at room temperature with no apparent loss of activity. Unreconstituted lyophilized CLECs of thermolysin appear to be viable indefinitely.

Figure 3:
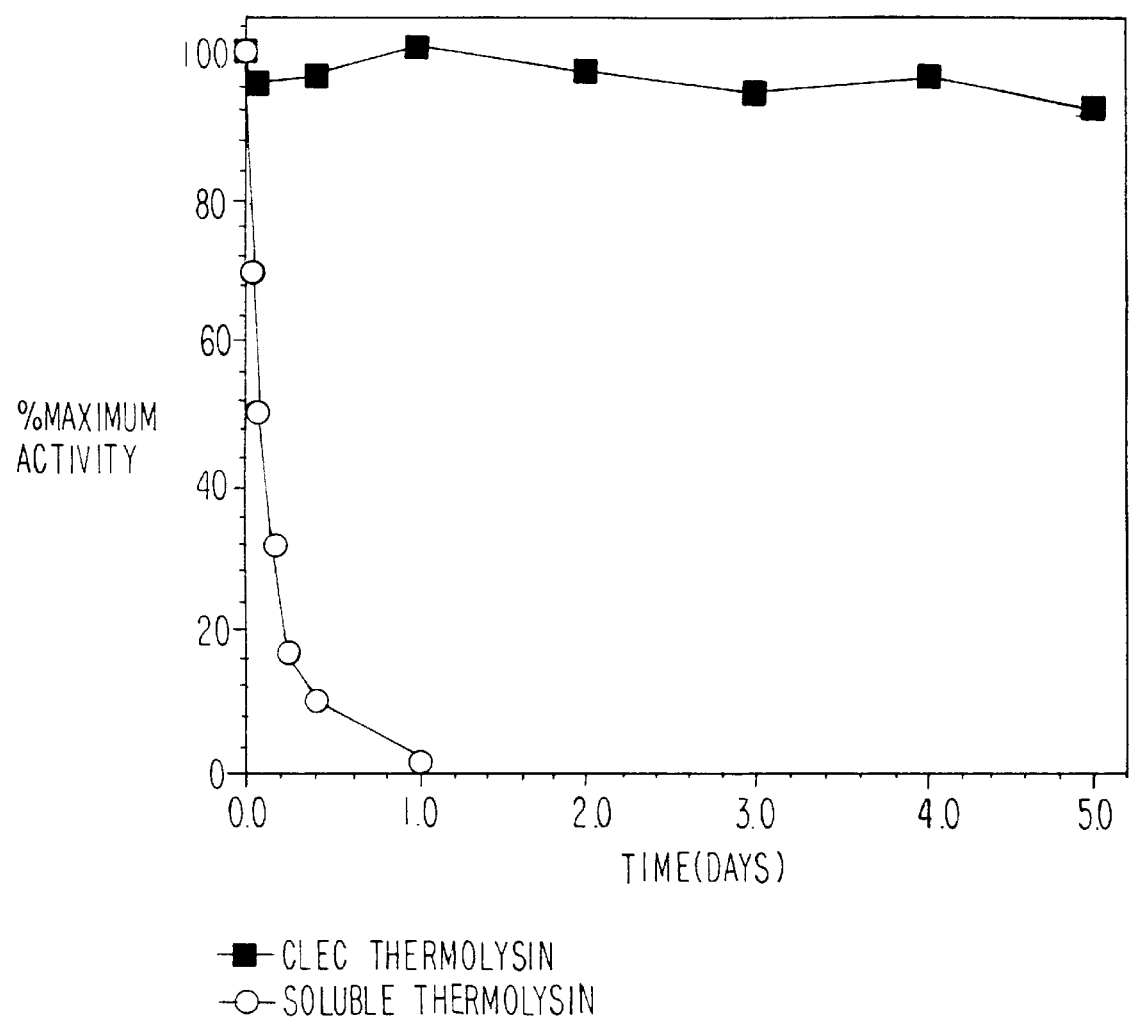
FIG. 3 is a graphic representation of measurement of the activity of soluble and crystalline thermolysin after incubation at 65° C.

Thermal stability and resistance to autolysis were demonstrated in thermolysin CLECs following incubation at 65° C. for five consecutive days (FIG. 3 and Table 10). Thermolysin CLECs retained maximum activity after five days incubation at elevated temperature. In contrast, the soluble thermolysin lost 50% of its initial activity after only two hours incubation and demonstrated negligible activity after 24 hours incubation at 65° C.

TABLE 10

Thermolysin Thermal Stability at 65° C.

% Maximum Activity

| | Time (days) | CLEC | Soluble Enzyme |
|---|---|---|---|
| 1 | 0.000 | 100.000 | 100.000 |
| 2 | 0.041 | | 70.000 |
| 3 | 0.083 | 96.000 | 50.000 |
| 4 | 0.164 | | 32.000 |
| 5 | 0.246 | | 17.000 |
| 6 | 0.410 | 97.0 | 10.000 |
| 7 | 1.000 | 101.0 | 2.000 |
| 8 | 2.000 | 97.0 | |
| 9 | 3.000 | 94.0 | |
| 10 | 4.000 | 96.0 | |
| 11 | 5.000 | 92.0 | |

The activity of soluble and CLEC thermolysin was measured following incubation at 65° C. Soluble thermolysin was incubated in 10 mM calcium acetate, 50 mM Tris pH 7.0 in a 65° C. water bath. The reaction volume was 500 μl. Final protein concentration was 10 mg/ml. Aliquots were removed at times 0, 1, 2, 4, 6, 10, and 18 hours. The samples were assayed by SDS-PAGE and FAGLA cleavage at room temperature as described above. For the thermolysin CLECs, a 250 μl crystal suspension in 10 mM calcium acetate and 50 mM Tris was also incubated in a 65° C. water bath. Activity was assayed at times 0, 1, 6, 24, 48, 72, 96, and 120 hours by FAGLA cleavage.

Resistance to Exogenous Proteolysis

Assessment of the resistance of the thermolysin CLEC to the action of an exogenous protease was also carried out. SDS-PAGE (Sodium dodecyl sulfate poly acrylamide gel electrophoresis) analysis suggests that commercial enzymes can contain a substantial percentage of contaminants, some of which might have proteolytic activity against the principal soluble enzyme species. Given the packing of enzyme molecules in a crystal lattice one might assume that the interior enzyme molecules in a CLEC would be protected from proteolysis. To test this possibility, thermolysin CLECs and a soluble enzyme preparation were incubated in the presence of the streptococcal protease, Pronase®, a nonspecific protease capable of digesting most proteins to free amino acids (Calbiochem 1990 Catalog; LaJolla, Calif.).

Soluble and CLEC thermolysin were incubated in 50 mM Tris, pH 7.5, at 40° C. in the presence of the protease Pronase® (Calbiochem). The Pronase® to thermolysin ratio was 1/40. To inhibit thermolysin autolysis and prevent the proteolytic destruction of pronase by the thermolysin, EDTA was added to the soluble enzyme reaction to a final concentration of 100 mM (EDTA inhibits thermolysin activity but not Pronase®). At the times indicated aliquots were removed from the reaction mix and activity was assayed spectrophotometrically by cleavage of the dipeptide substrates FAGLA. To offset thermolysin inhibition due to the presence of EDTA, the spectrophotometric assay of soluble enzyme activity was performed in 0.5M calcium acetate buffer pH 7.0 and enzyme concentration was increased two fold. Crosslinked crystalline enzyme was assayed as described above.

Figure 4:
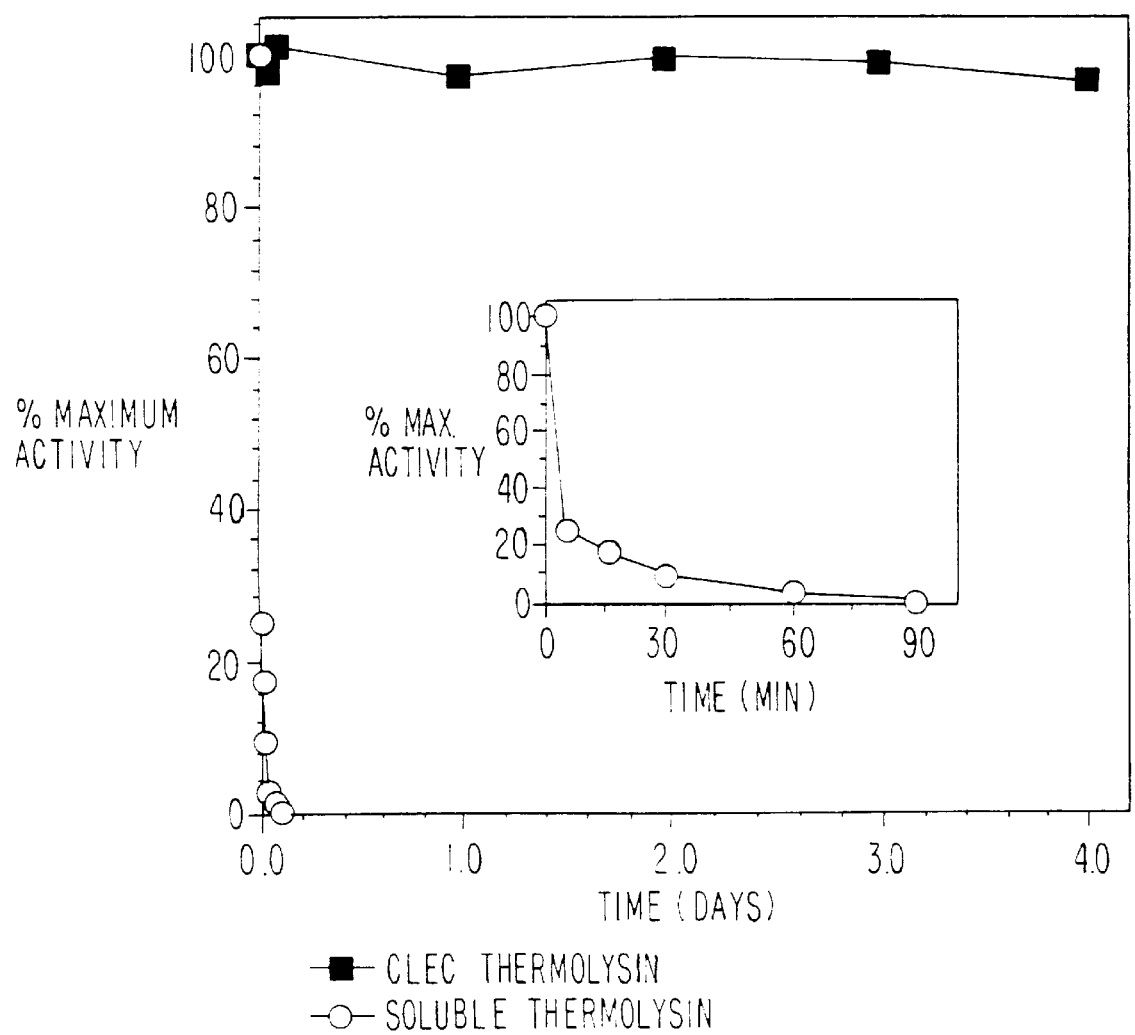
FIG. 4 is a graphic representation of results of assessment of resistance of soluble and thermolysin CLEC to exogenous proteolytic degradation.

As can be seen in FIG. 4 and Table 11, the soluble thermolysin was rapidly degraded and lost all activity after 90 minutes incubation. In contrast, the activity of the thermolysin CLEC was unaffected by four days incubation in the presence of protease. This near imperviousness to proteolysis is of particular interest in diagnostic biosensor applications where a suitable CLEC might be called upon to act in the presence of an unknown cocktail of naturally occurring proteolytic enzymes.

TABLE 11

Protease Resistance

| | Time (days) | % Maximum Activity | | Time (min) |
|---|---|---|---|---|
| | | CLEC | Soluble Enzyme | |
| 1 | 0.000 | 100.0 | 100.0 | 0.000 |
| 2 | 0.003 | | 25.0 | 5.000 |
| 3 | 0.010 | | 17.5 | 15.000 |
| 4 | 0.021 | | 9.5 | 30.000 |
| 5 | 0.042 | 98.0 | 3.0 | 60.000 |
| 6 | 0.063 | | 1.0 | 90.000 |
| 7 | 0.084 | 101.0 | 0.0 | |
| 8 | 1.000 | 97.0 | | |
| 9 | 2.000 | 99.0 | | |
| 10 | 3.000 | 98.0 | | |
| 11 | 4.000 | 96.0 | | |

Stability in the Presence of Organic Solvent

In order for enzymes to gain ideal acceptance as viable industrial catalysts, they must be able to function without excessive intervention in the practical environment of manufacturing processes. In particular, this would include the use of aqueous, polar and non-polar organic solvents, and mixtures of these. In commercial applications, aqueous-organic solvent mixtures allow manipulation of product formation by taking advantage of relative solubilities of products and substrates.

Soluble thermolysin and thermolysin CLECs exhibited markedly different stability in the presence of organic solvents. (Table 12). Soluble enzyme concentrations which could be incubated in organic solvent were limited to a maximum of 10 mg/ml. Concentrations greater than this value resulted in the instantaneous precipitation of thermolysin upon addition of organic solvent. In contrast, thermolysin CLEC concentrations were limited only by the volume occupied by the crystals. Soluble thermolysin retained the greatest activity (75%) following incubation in acetone, and the least (36%) in tetrahydrofuran. Following a one hour incubation in the presence of acetonitrile or dioxane the soluble enzyme lost approximately 50% of its initial activity. The CLEC thermolysin retained greater than 95% maximum activity following incubation with all organics assayed.

TABLE 12

|  | % Maximum Activity | |
| --- | --- | --- |
|  | Soluble Enzyme | CLEC |
| Acetonitrile | 42 | 102 |
| Dioxane | 66 | 97 |
| Acetone | 75 | 99 |
| THF* | 36 | 96 |

*Tetrahydro Furan

Stability in Organic Solvents

Thermolysin CLECs or soluble thermolysin preparations were incubated in 50% (v/v) solutions of the indicated organic solvents. A 100 µl slurry of thermolysin CLECs (10 mg/ml) in 10 mM Tris pH 7 was placed in a ½ dram glass vial. An equal volume of the indicated organic solvent was added and the mixture was briefly vortexed. Twenty µl of soluble thermolysin (100 mg/ml) was diluted in 80 µl of 0.015M Tris buffer pH 7.0 in a ½ dram glass vial. A 100 µl volume of organic solvent was then added to the protein solution and briefly vortexed. CLEC and soluble enzyme were incubated in the presence of organic solvent for one hour at 40° C. Following incubation, enzyme activity was assayed by cleavage of the dipeptide substrate FAGLA as described.

Low water concentration is thought to disfavor unfolding to intermediate states on the path to enzyme denaturation. In CLECs, this restriction of conformational mobility is provided by the inter-molecular contacts and cross-links between the constituent enzyme molecules making up the crystal lattice, rather than by the near-absence of water in the medium. As a result, intermediate water-organic solvent concentrations are readily tolerated by enzymes when formulated as CLECs, something previously unobserved with enzymes (see Table 12). This discovery opens up whole new areas of synthetic chemistry to exploitation using enzyme catalysis.

Even in near-anhydrous organic solvents, however, the routine use of enzymes has been hampered by their tendency to form ill-defined suspensions that are subject to clumping and other aggregation problems. This property makes these preparations inherently unattractive for large scale industrial processes. In contrast, CLECs and the constituent enzymes within the crystal lattice, remain mono-disperse in all these solvents.

Comparison with Other Immobilization Methods

A number of useful reviews of enzyme immobilization methods have appeared in the literature (Maugh, T. H., Science, 223: 474–476 (1984)); Tramper, J., Trends in Biotechnology 3: 45–50 (1985)) . In these, the enzyme always represents a small fraction of the total volume of the immobilized particle, the bulk of it being inert carrier material. The carrier increases the mean free path between the solvent exterior of the immobilized enzyme particle and the enzyme active sites, exacerbating diffusion problems (Quiocho, F. A. and Richards, F. M., Biochemistry 5: 4062–4076 (1967)).

In a CLEC, the crosslinked crystal matrix provides its own support, eliminating the need for a carrier. As a result, the concentration of enzyme in a CLEC is close to the theoretical packing limit that can be achieved for molecules of a given size, greatly exceeding densities achievable even in concentrated solutions. The entire CLEC consists of active enzyme, and thus, the diffusion-related reduction of enzyme reaction rates usually observed with conventionally immobilized enzymes relative to enzymes in solution are minimized (See FIG. 1), since the mean free path for substrate and product between active enzyme and free solvent will be greatly shortened for CLECs (compared to a conventional immobilized enzyme carrier particles). Importantly, the constituent enzyme in CLECs is intrinsically mono-disperse, and can be recovered by simple manipulations of the CLEC particles, such as filtration, centrifugation or decantation of solvent.

EXAMPLE 3

Soluble and CLEC Thermolysin-Catalysed Synthesis of the Aspartame Precursor Z—Asp—Phe—OMe Soluble and CLEC thermolysin catalysed synthesis of the aspartame precursor was performed in a repeated batch experiment. Three different experimental parameters were assessed: 1. thermolysin CLEC versus soluble thermolysin half-life, 2. thermolysin CLEC versus soluble thermolysin specific activity (equivalent protein concentration) and 3. thermolysin CLEC versus soluble thermolysin total activity (equivalent protein dry weight).

The reagents were prepared as follows:
Solvent—a buffer (50 mM MES—NaOH, 5 mM $CaCl_2$ (2-[N-morpholino]ethane-sulfonic acid)(Sigma) saturated ethyl acetate, pH 6.0) saturated solution of ethyl acetate (Nakanishi, K. et al., Biotechnology 3:459–464 (1985)). The MES buffer was prepared by dissolving 9.76 g MES and 0.102 g $CaCl_2$ in 90 ml deionized water. The pH was adjusted to 6.0 with 5N NaOH. The volume was adjusted to 100 ml. To prepare buffer saturated ethyl acetate, 10 ml MES buffer was combined with 90 ml ethyl acetate in separatory funnel, following agitation the organic phase was collected.
Substrates—240 mM L—Phe—O—Me, 80 mM CBZ—L-Aspartic Acid. L—Phe—O—Me was prepared by chloroform extraction of L—Phe—O—Me HCl. Equimolar amounts of L—Phe—O—Me HCl and $Na_2CO_3$ were dissolved in deionized water and agitated with an appropriate amount of chloroform to extract the L—Phe—O—Me. The chloroform was dehydrated with an appropriate amount of $MgSO_4$ and evaporated at 40° C. L—PheOMe was stored as a 2.4M solution in ethyl acetate at −20° C.
Thermolysin CLECS—0.216 mM thermolysin CLECs (7.5 mg/ml enzyme, approximately 15 mg/ml dry weight).

Procedure for 3 ml Batch Reaction 0.214 g of N—CBZ—L—Asp was dissolved in 9 ml buffer saturated ethyl acetate. 1 ml 2.4M Phe—O—Me stock as described above was added to the CBZ-aspartic acid. Lyophilized CLECs or lyophilized soluble thermolysin was added to 3 ml of the reaction mix containing buffered solvent and substrates. The reaction was incubated at 55° C. with agitation, pH was maintained at 6.0. The CLECs remained insoluble and were removed from the reaction by filtration and low speed centrifugation. The conversion of substrates to product was monitored by removing 0.1 ml of reaction mix at 1 hr intervals for TLC or HPLC. The reaction volumes were scaled to 19 ml for the 24 hour continuous batch reactions.

Assay of Aspartame Precursor Product

The progress of the reaction was followed by thin layer chromatography (TLC) (Lindeberg, G, *J. Chem. Education* 64:1062–1064 (1987)) (mobilr phsdr; 1:1:3 water:acetic acid:N-butanol). Solid phase; silica gel. Visualize by UV at 245 nm and ninhydrin, and by high performance liquid chromatography (HPLC) (Nakanishi, K. et al. *Biotechnology* 3:459–464 (1985): Oyama, K. et al., *Meth. in Enzymology* 136:503–516 (1984); Ooshima, H. et al., *Biotechnology Letters* 7:789–792 (1985)). The reaction was monitored at 214 and 280 n. One hundred per cent conversion to product is defined as one hundred per cent conversion of CBZ-aspartic acid to aspartame precursor.

Continuous Batch Synthesis of the Aspartame Precursor (Half-life)

Soluble and CLEC thermolysin catalysed synthesis of the aspartame precursor was performed continuously for 10 days in a repeated 24 hour batch experiment under the conditions described above. CLEC thermolysin concentration was 15 mg/ml dry weight. Soluble thermolysin (Diawa 10% protein) concentration was 37.5 mg/ml dry weight. Product was recovered and fresh substrate was added to the reaction every 24 hr. Enzyme was recovered from the reaction mix by centrifugation and filtration. The % product was assayed by TLC and HPLC as described above (FIG. 5).

Batch synthesis data (total activity)

| | % Product | |
|---|---|---|
| Time (hours) | CLECs | Soluble |
| 0 | 0 | 0 |
| 1 | 27 | 0 |
| 2 | 63 | 3 |
| 3 | 95 | 5 |
| 4 | 100 | 7 |

EXAMPLE 4

Crystallization, Cross-linking and Lyophilization of Elastase and Assessment of Characteristics of the Resulting Product Crystallization of Elastase Lyophilized porcine pancreatic elastase (Serva) was dissolved in 0.1M sodium acetate pH 5.0 to a concentration of 5 mg/ml (w/v) at room temperature. Rod shaped elastase crystals were visible within one minute of the complete salvation of the protein. The crystallization solution was transferred to 4° C. and crystallization was completed overnight. Crystals were recovered by centrifugation as previously described.

Cross-linking of Elastase Crystals

A 200 μl volume of elastase crystals was added to a 1.3 ml solution of 5.77% glutaraldehyde and 1.5M sodium acetate pH 5.0. The crystals were crosslinked for one hour with mild agitation (stir plate). Following crosslinking the crystals were washed with three 15 ml volumes of 0.2M Tris pH 8.0. The elastase CLEC was lyophilized as described in Example 2.

Enzymatic Activity of Soluble and CLEC Elastase

The catalytic activity of soluble and CLEC elastase was assayed spectrophotometrically by measuring hydrolysis of the substrate succinyl-$(Ala)_3$ p-nitroanilide (Bachem) [Bieth, et al. Biochem. Med 11:350–357 (1974)] (Table 13, FIG. 6). Cleavage was monitored by increasing absorbance at 410 nm. Initial substrate concentration was $2 \times 10^{-4}$. Enzyme concentration was $2.8 \times 10^{-7}$M. CLEC or soluble enzyme was added to a 5 ml reaction volume containing substrate in 0.2M Tris pH 8.0. As described previously, CLEC enzyme was removed from the reaction mix prior to measuring absorbance.

TABLE 13

Elastase Activity

| | | Absorbance 400 mn | |
|---|---|---|---|
| | Time (min) | CLEC | Soluble Enzyme |
| 1 | 0.0 | 0.000 | 0.000 |
| 2 | 1.0 | 0.103 | 0.205 |
| 3 | 2.0 | 0.195 | 0.390 |
| 4 | 3.0 | 0.366 | 0.672 |
| 5 | 3.0 | 0.523 | 0.923 |
| 6 | 4.0 | 0.657 | 1.098 |
| 7 | 5.0 | 0.780 | 1.227 |
| 8 | 6.0 | 0.888 | 1.326 |
| 9 | 7.0 | 0.974 | 1.393 |
| 10 | 10.0 | 1.170 | 1.512 |
| 11 | 15.0 | 1.365 | 1.586 |

Resistance to Exogenous Proteolysis

Assessment of the resistance of the elastase CLEC to the action of protease was also performed under identical conditions as described for thermolysin (Example 2). Activity of the soluble and CLEC enzyme, following incubation with protease, was assayed by hydrolysis of the nitroanilide substrate as described above (Table 14 and FIG. 7).

TABLE 14

Elastase Resistance to Proteolysis

| | | % Maximum Activity | |
|---|---|---|---|
| | Time | CLEC | Soluble Enzyme |
| 1 | 0.0 | 100.0 | 100.0 |
| 2 | 10.0 | | 53.0 |
| 3 | 20.0 | | 32.0 |
| 4 | 30.0 | 101.0 | 18.0 |
| 5 | 45.0 | | 11.0 |
| 6 | 60.0 | 102.0 | 8.0 |
| 7 | 120.0 | 101.0 | 3.0 |
| 8 | 180.0 | 103.0 | 2.0 |

EXAMPLE 5

Crystallization, Cross-linking and Lyophilization of Esterase and Assessment of Characteristics of the Resulting Product Crystallization of Esterase As disclosed here, 30 mg/ml ammonium sulfate suspension of pig liver esterase (Fluka) was dissolved in 0.25M calcium acetate pH 5.6 at room temperature. Esterase crystals were visible within several minutes following addition of the calcium acetate solution. The crystallization solution was allowed to stand at room temperature and crystallization was completed overnight. Crystals were recovered by centrifugation as previously described in Example 2.

Cross-linking of Esterase Crystals

As disclosed here, a 300 μl volume of esterase crystals were added to a 5 ml solution of 12.5% glutaraldehyde and 0.5M sodium acetate pH 5.5. The crystals were crosslinked for one hour with mild agitation (stir plate). Following cross-linking the crystals were washed with three 15 ml volumes of 0.5M calcium acetate pH 6.3. The esterase CLEC was lyophilized as previously described in Example 2.

Enzymatic Activity of Soluble and CLEC Esterase

Figure 8:
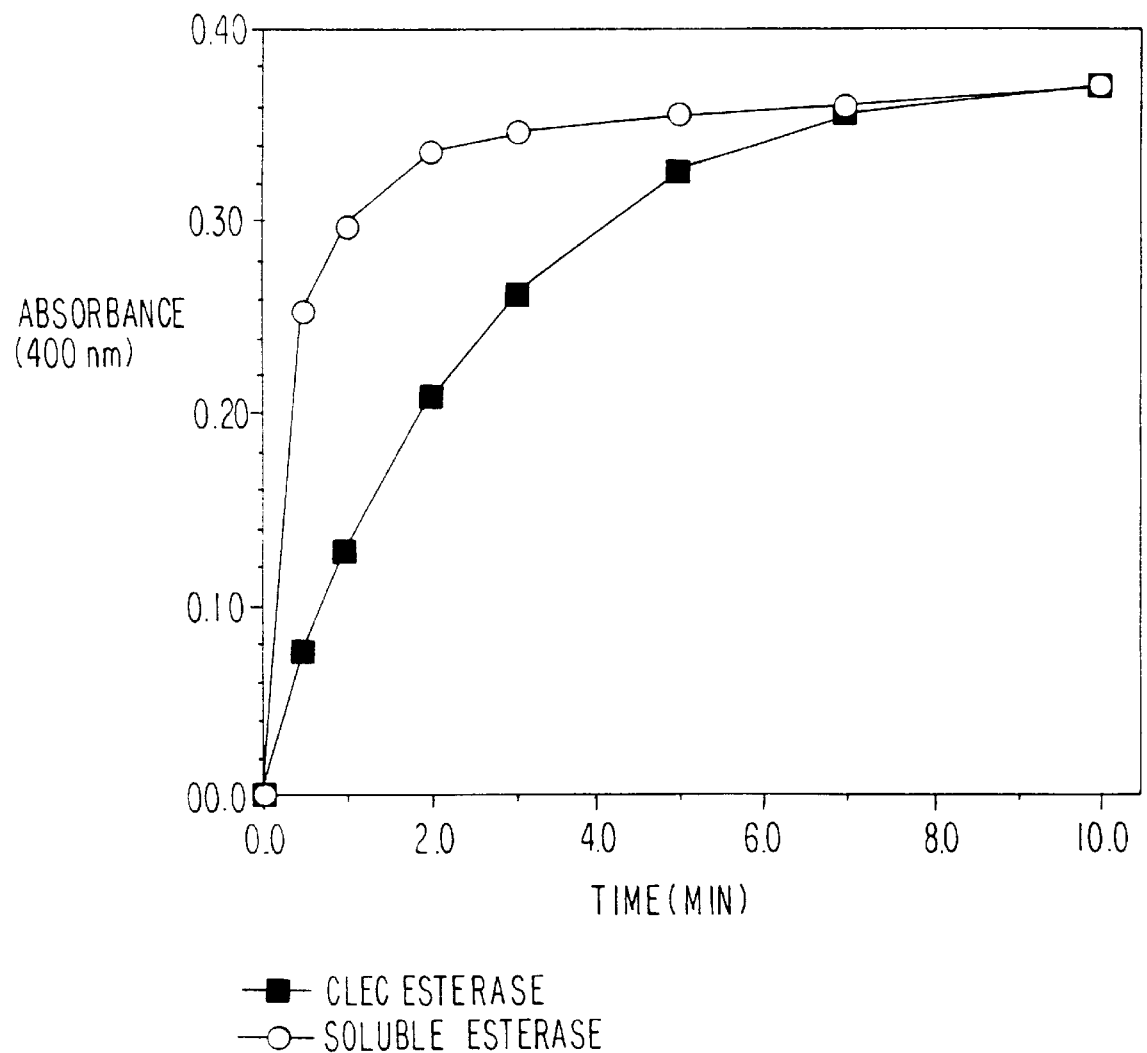
FIG. 8 is a graphic representation of results of the assessment of enzymatic activity for soluble esterase and the corresponding esterase CLEC.
Figure 9:
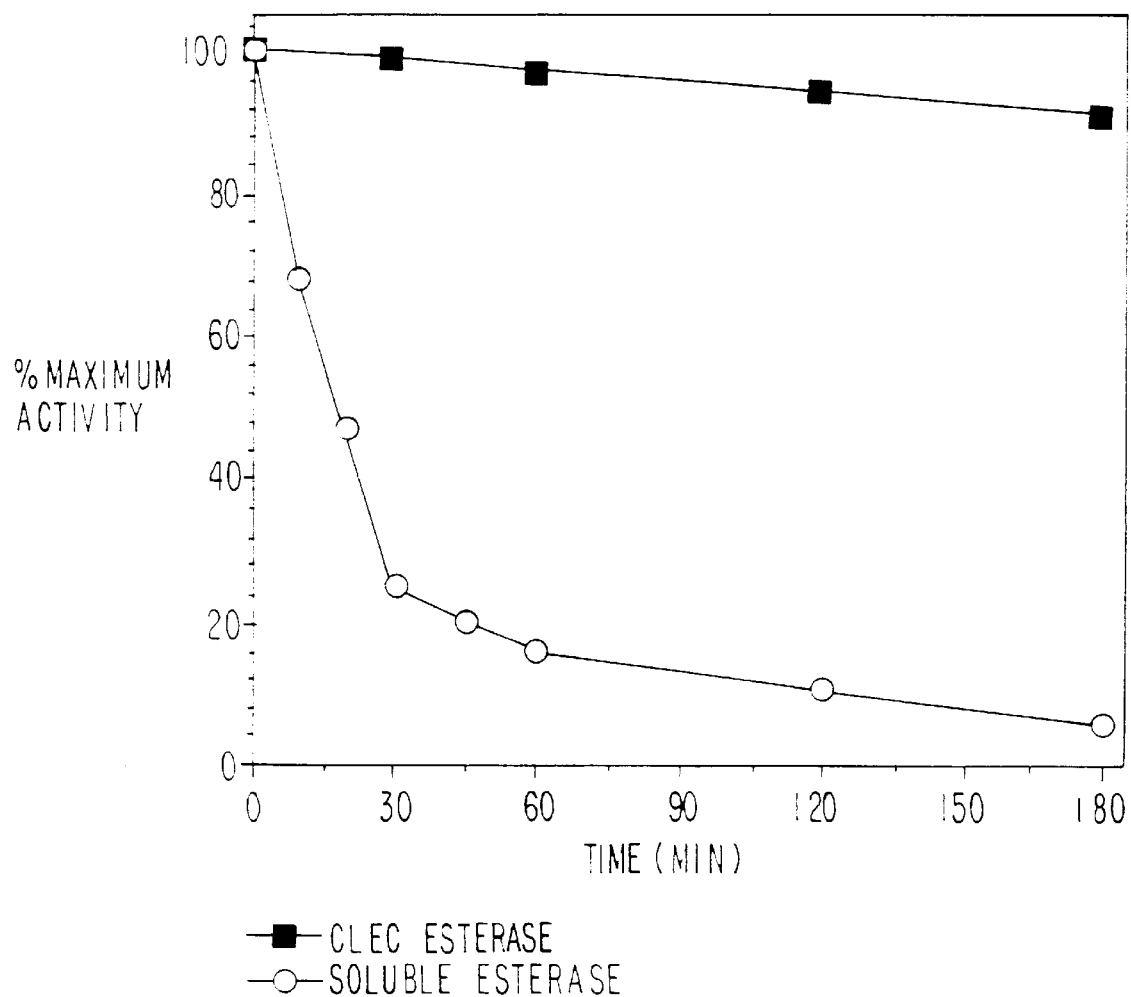
FIG. 9 is a graphic representation of the resistance of soluble esterase and the corresponding esterase CLEC to exogenous proteolytic degradation.

The catalytic activity of soluble and CLEC esterase was assayed spectrophotometrically by monitoring hydrolysis of the substrate p-nitrophenyl acetate (Fluka) (Table 15 and FIG. 8). Cleavage was monitored by increasing absorbance at 400 nm. Initial substrate concentration was 0.001%. Enzyme concentration was $1 \times 10^{-8}$M. CLEC or soluble enzyme was added to a 5 ml reaction volume containing substrate in 0.25M calcium acetate pH 6.3. As described previously in Example 2, CLEC enzyme was removed from the reaction mix by centrifugation prior to measuring absorbance.

TABLE 15

Esterase Activity

| | | Absorbance 400 nm | |
|---|---|---|---|
| | Time (min) | CLEC | Soluble Enzyme |
| 1 | 0.0 | 0.000 | 0.000 |
| 2 | 0.5 | 0.770 | 0.252 |
| 3 | 1.0 | 0.128 | 0.297 |
| 4 | 2.0 | 0.208 | 0.337 |
| 5 | 3.0 | 0.260 | 0.346 |
| 6 | 5.0 | 0.324 | 0.353 |
| 7 | 7.0 | 0.353 | 0.359 |
| 8 | 10.0 | 0.369 | 0.368 |

Resistance to Exogenous Proteolysis

Assessment of the resistance of the esterase CLEC to the action of protease was also performed under identical conditions as described for thermolysin (Example 2). Activity of the soluble and CLEC enzyme, following incubation with protease, was assayed by hydrolysis of the substrate p-nitrophenyl acetate as described above (Table 16 and FIG. 9).

TABLE 16

Esterase Resistance to Proteolysis

| | | % Maximum Activity | |
|---|---|---|---|
| | Time (min) | CLEC | Soluble Enzyme |
| 1 | 0.0 | 100.0 | 100.0 |
| 2 | 10.0 | | 68.0 |
| 3 | 20.0 | | 47.0 |
| 4 | 30.0 | 99.0 | 25.0 |
| 5 | 45.0 | | 20.0 |
| 6 | 60.0 | 97.0 | 16.0 |
| 7 | 120.0 | 94.0 | 10.0 |
| 8 | 180.0 | 91.0 | 6.0 |

EXAMPLE 6

Crystallization, Cross-linking and Lyophilization of *Geotrichum candidum* Lipase and Assessment of Characteristics of the Resulting Product Crystallization of Lipase As disclosed here, the enzyme lipase (*Geotrichum* (*G.*) *candidum*) was crystallized by vapor diffusion from an aqueous solution of 20 mg/ml protein in 50 mM Tris pH 7 containing 8% ammonium sulfate. Bipyrimidal crystals were visible after 20 to 30 days incubation at room temperature. Crystals were recovered by centrifugation, as previously described in Example 2.

Cross-linking of Lipase Crystals

As disclosed here, lipase crystals were added to a solution of 12.5% glutaraldehyde and 50 mM Tris pH 5.6. The crystals were crosslinked for one hour. Following cross-linking the crystals were washed with three 15 ml volumes of 50 mM Tris pH 7.0. The lipase CLEC was lyophilized, as previously described in Example 2.

Enzymatic Activity of Soluble and CLEC Lipase

Figure 10:
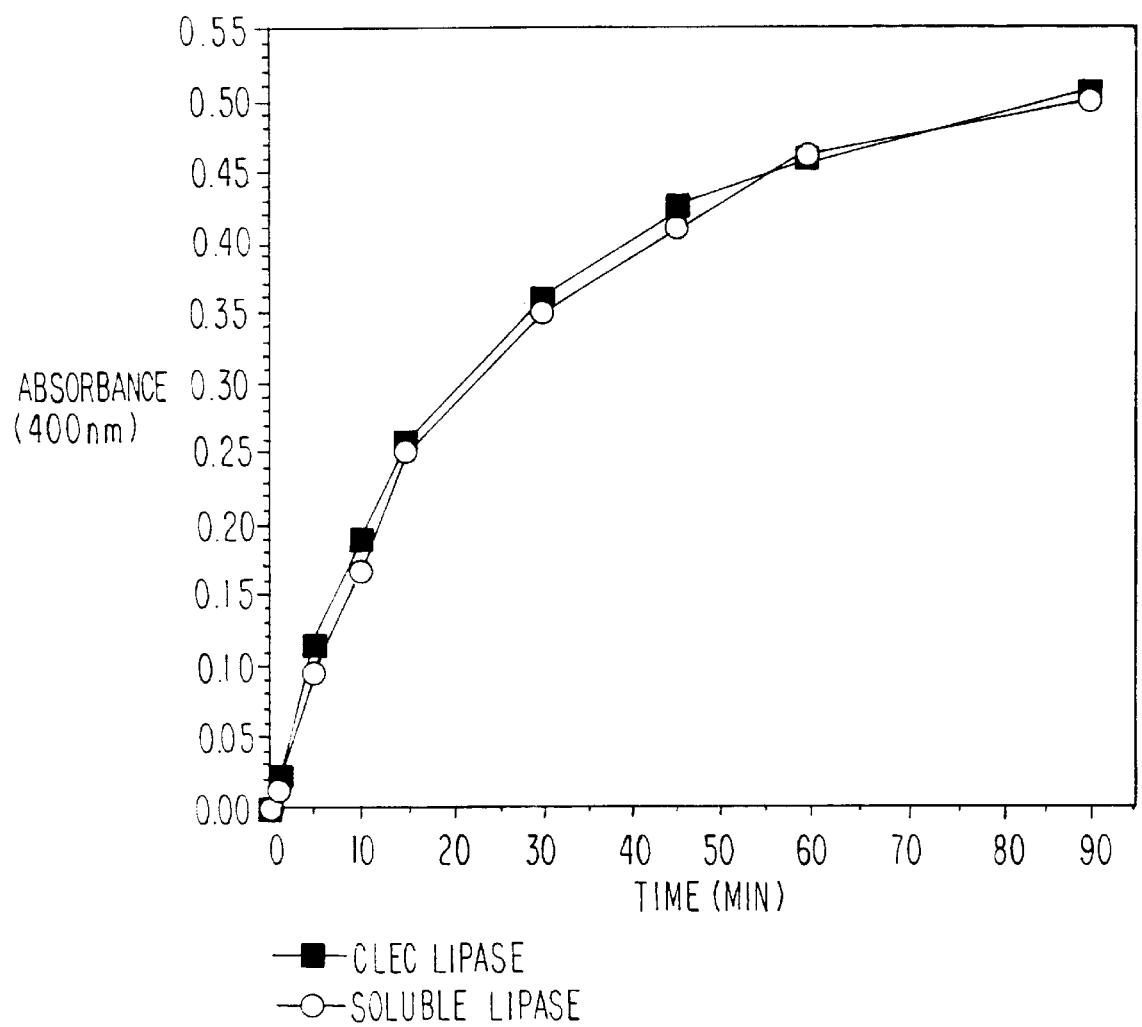
FIG. 10 is a graphic representation of results of the assessment of enzymatic activity for soluble lipase and the corresponding lipase CLEC.

The catalytic activity of soluble and CLEC lipase was assayed spectrophotometrically by monitoring hydrolysis of the substrate p-nitrophenyl acetate (Table 17 and FIG. 10). Cleavage was monitored by increasing absorbance at 400 nm. Initial substrate concentration was 0.005%. Enzyme concentration was $1.5 \times 10^{-8}$M. CLEC or soluble enzyme was added to a 5 ml reaction volume containing substrate in 0.2M Tris pH 7.0 at room temperature. As described previously in Example 2, CLEC enzyme was removed from the reaction mix by centrifugation prior to measuring absorbance.

TABLE 17

Lipase Activity

| | | Absorbance 400 nm | |
|---|---|---|---|
| | Time (min) | CLEC | Soluble Enzyme |
| 1 | 0.0 | 0.000 | 0.000 |
| 2 | 1.0 | 0.013 | 0.021 |
| 3 | 5.0 | 0.094 | 0.116 |
| 4 | 10.0 | 0.164 | 0.186 |
| 5 | 15.0 | 0.248 | 0.258 |
| 6 | 30.0 | 0.346 | 0.357 |
| 7 | 45.0 | 0.407 | 0.420 |
| 8 | 60.0 | 0.461 | 0.459 |
| 9 | 90.0 | 0.497 | 0.502 |

EXAMPLE 7

Crystallization, Cross-linking and Lyophilization of Lysozyme and Assessment of Characteristics of the Resulting Product Crystallization of Lysozyme Following the method of Blake, C. C. F. et al., Nature 196:1173 (1962) 200 mg of lyophilized hen egg white lysozyme (Boehringer Mannheim) was dissolved in 2.5 ml of 0.04M sodium acetate buffer pH 4.7 at room temperature. Following solvation of the protein, 2.5 ml of 10% sodium chloride were added to the lysozyme solution dropwise with stirring. The crystallization solution was allowed to stand overnight at room temperature, and crystallization was completed in forty-eight hours. Crystals were recovered by centrifugation, as previously described in Example 2.

Cross-linking of Lysozyme Crystals

As described here, a 500 μl volume of lysozyme crystals was added to 10 ml of 24% glutaraldehyde and 50 mM Tris pH 5.6 containing 20% sodium chloride. The crystals were crosslinked for 20 minutes with mild agitation (stir plate). Following cross-linking the crystals were washed with three 50 ml volumes of 20 mM calcium acetate and 50 mM potassium chloride pH 5.3. The lysozyme CLEC was lyophilized, as previously described in Example 2.

Enzymatic Activity of Soluble and CLEC Lysozyme

The catalytic activity of soluble and CLEC lysozyme was assayed by measuring the rate of hydrolysis of the substrate 4-methylumbelliferyl N-acetyl-chitrioside (Fluka) (Yang, Y. and Hamaguchi, K. J. Biochem. 8:1003–1014 (1980) (Table 18 and FIG. 11). The release of 4-methylumbelliferone was followed fluorimetrically (Perkin Elmer Model LS-50). Initial substrate concentration was $1.42 \times 10^{-3}$. Enzyme concentration was $3 \times 10^{-7}$. CLEC or soluble enzyme was added to a 2 ml reaction volume containing substrate in 20 mM calcium acetate and 50 mM potassium chloride pH 5.3 at 42° C. The amount of 4-methylumelliferone was determined fluorimetrically by measuring fluorescence intensities at 450 nm with excitation at 360 nm. Slit width for both excitation and emission was 10 mm. As described previously in Example 2, CLEC enzyme was removed from the reaction mix by centrifugation prior to measuring fluorescence.

TABLE 18

Lysozyme Activity

| Time (min) | Fluorescence | |
| | CLEC | Soluble Enzyme |
| --- | --- | --- |
| 1 | 0.000 | 0.000 | 0.000 |
| 2 | 10.000 | 4.400 | 18.900 |
| 3 | 30.000 | 10.500 | 29.400 |
| 4 | 60.000 | 27.500 | 44.800 |
| 5 | 90.000 | 33.800 | 51.700 |
| 6 | 120.000 | 45.900 | 59.800 |

EXAMPLE 8

Crystallization, Cross-linking and Lyophilization of Asparaginase and Assessment of Characteristics of the Resulting Product Crystallization of Asparaginase As a modification of the procedure described by Grabner et al. [U.S. Pat. No. 3,664,926 (1972)] 25 mg of lyophilized asparaginase (Worthington) were dissolved in 500 μl of 50 mM sodium phosphate buffer pH 7.2. The solution was cooled to 4° C. and the pH adjusted to 5.0 with 1M acetic acid. Cold (−20° C.) ethanol was then added dropwise to the asparaginase solution to a final concentration of 33%. The solution was incubated at 4° C. Crystallization was completed in forty-eight hours. Crystals were recovered by centrifugation as previously described.

Cross-linking of Asparaginase Crystals

As disclosed here, asparaginase crystals were crosslinked in a solution of 7.5% glutaraldehyde in 50 mM sodium phosphate buffer pH 5.6. Following crosslinking the crystals were washed with five 15 ml volumes of 50 mM tris pH 7.0. The asparaginase CLECs were lyophilized, as previously described in Example 2.

Enzymatic Activity of Soluble and CLEC Asparaginase

Figure 12:
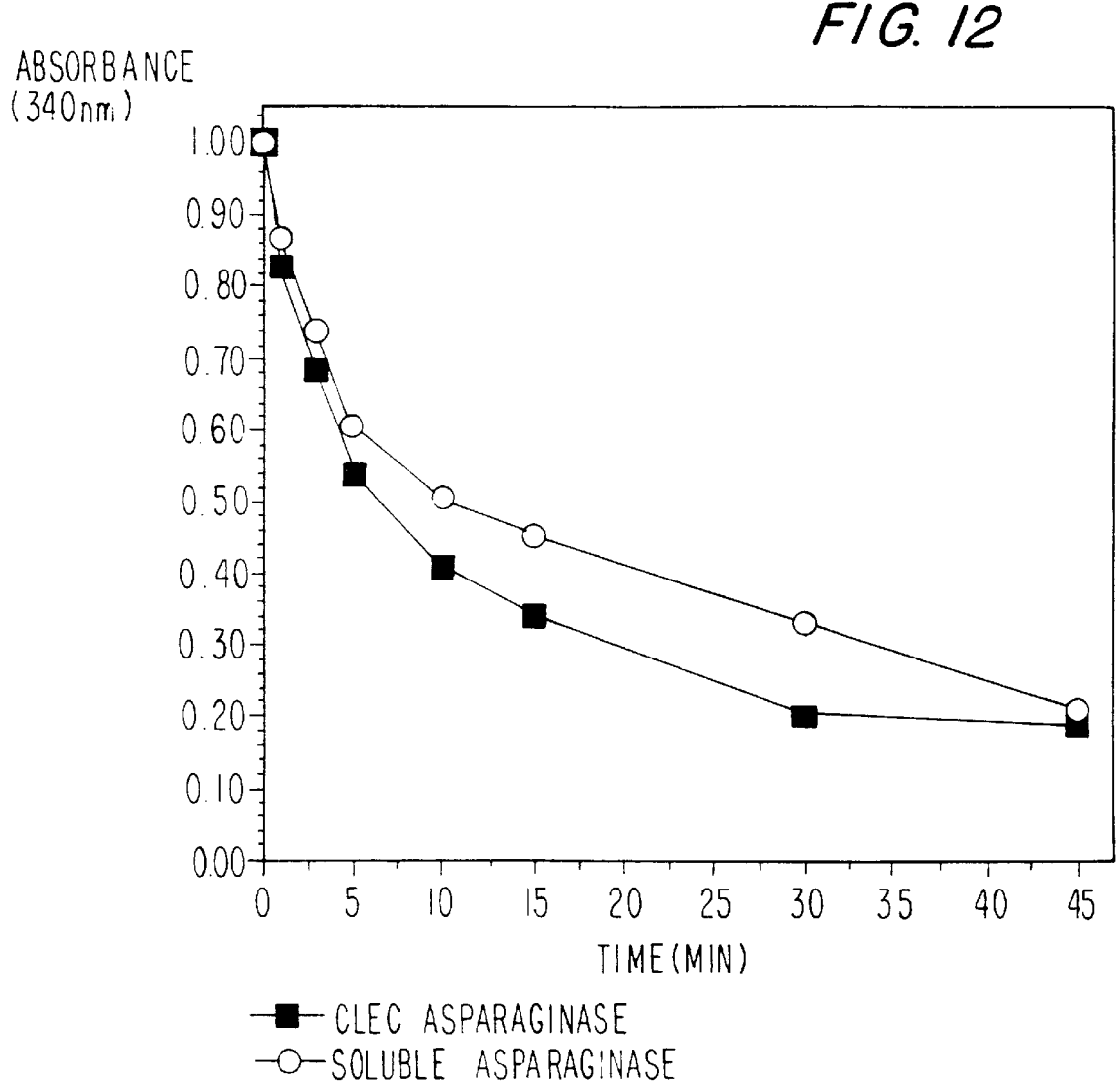
FIG. 12 is a graphic representation of results of the assessment of enzymatic activity for soluble asparaginase and the corresponding asparaginase CLEC.
Figure 13:
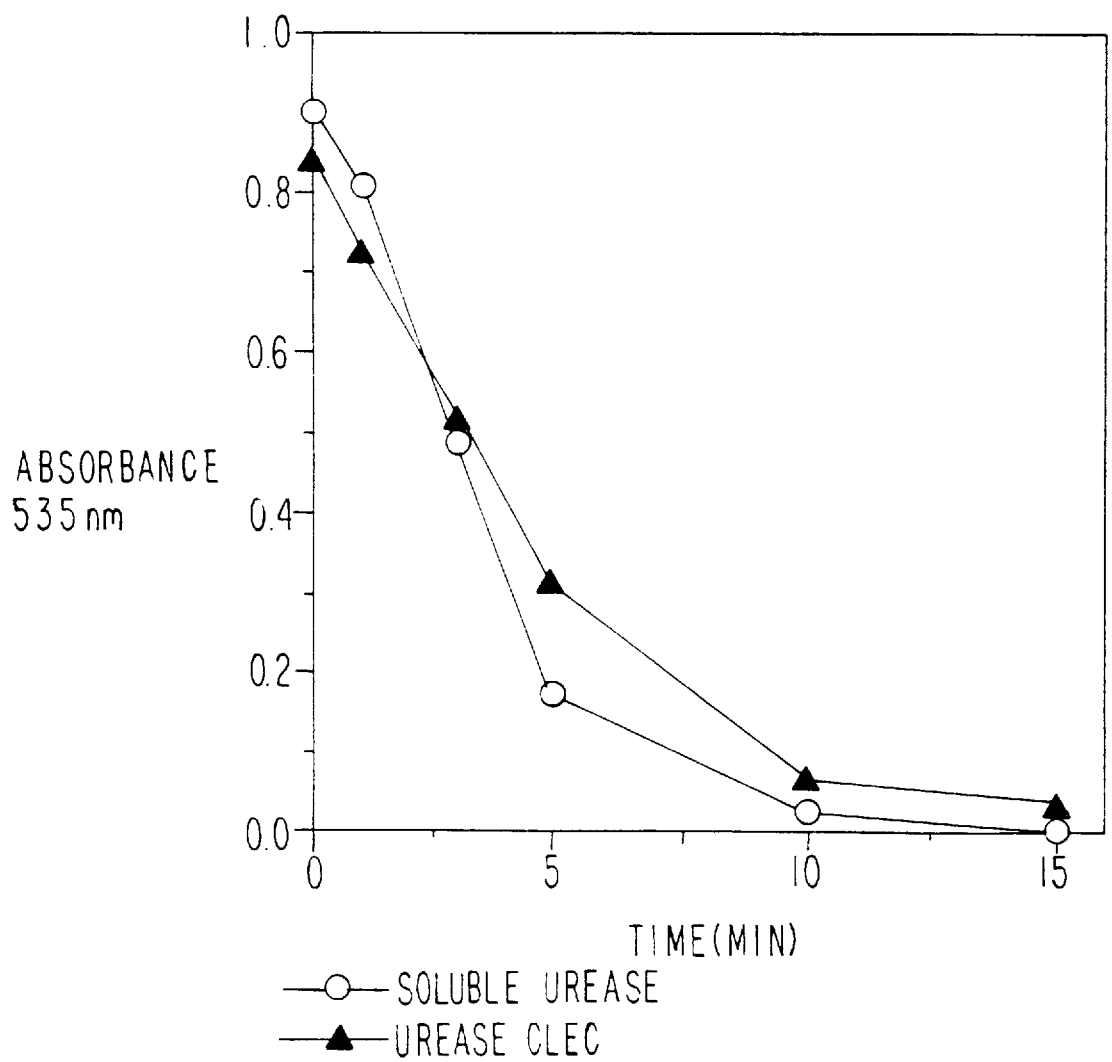
FIG. 13 is a graphic representation of results of the assessment of enzymatic activity of soluble urease and the corresponding urease CLEC.

The catalytic activity of soluble and CLEC asparaginase was assayed spectrophotometrically by measuring evolution of ammonium ion in the coupled enzymatic reaction described below (all reagents were purchased from Boehringer Mannheim) (Table 19 and FIG. 12).

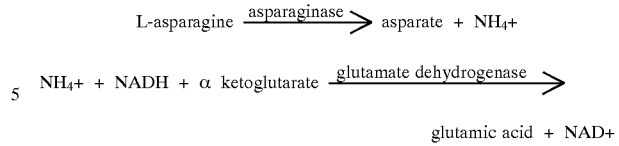

Oxidation of NADH was measured by decreasing absorbance at 340 nm. Initial NADH concentration was 1.4 mg/ml. Asparagine concentration was $10^{-3}$M. Alpha ketoglutarate concentration was $10^{-4}$M. Glutamate dehydrogenase concentration was $10^{-7}$M. Asparaginase concentration was $2.3 \times 10^{-8}$M. As described previously in Example 2, CLEC enzyme was removed from the reaction mix by centrifugation prior to measuring absorbance.

TABLE 19

Asparaginase Activity

| | Absorbance 340 nm | |
| Time (min) | CLEC | Soluble Enzyme |
| --- | --- | --- |
| 1 | 0.0 | 1.000 | 1.000 |
| 2 | 1.0 | 0.867 | 0.825 |
| 3 | 3.0 | 0.739 | 0.684 |
| 4 | 5.0 | 0.603 | 0.538 |
| 5 | 10.0 | 0.502 | 0.406 |
| 6 | 15.0 | 0.449 | 0.338 |
| 7 | 30.0 | 0.328 | 0.199 |
| 8 | 45.0 | 0.211 | 0.187 |

EXAMPLE 9

Crystallization, Crosslinking and Lyophilization of Urease and Assessment of Characteristics of the Resulting Product Crystallization of Urease Fifteen thousand units (approximately 180 mg) of lyophilized Jack Bean urease (Boehringer Mannheim) were dissolved in 3 ml of 150 mM sodium phosphate buffer pH 6.8. Acetone was added to the 3 ml urea solution by overnight vapor diffusion against 80 ml of 50% acetone/50% water. The solution was stirred gently during the addition of acetone. Crystallization was completed in sixteen hours. Crystals were recovered by centrifugation as previously described. Urease crystals were washed two times with 40% acetone in 50 mM sodium phosphate buffer pH 6.8. Crystals were recovered by centrifugation following washing. Crystallization resulted in a 40% decrease in the total activity of the CLEC urease compared to soluble urease, when assayed spectrophotometrically, as described below.

Cross-linking of Urease Crystals

As disclosed here, urease crystals were crosslinked in a solution of 2% glutaraldehyde, 30% acetone in 50 mM sodium phosphate buffer pH 6. Following cross-linking the crystals were washed with four, one liter volumes of 50M sodium phosphate buffer pH 6.8. Washed crystals were suspended in deionized water and lyophilized as previously described in Example 2.

TABLE 20

Urease Activity

| | | Absorbance 535 nm | |
|---|---|---|---|
| | Time (min) | CLEC urease | Soluble urease |
| 1 | 0 | 0.843 | 0.901 |
| 2 | 1 | 0.729 | 0.809 |
| 3 | 3 | 0.525 | 0.488 |
| 4 | 5 | 0.311 | 0.170 |
| 5 | 10 | 0.063 | 0.022 |
| 6 | 15 | 0.036 | 0.000 |

Enzymatic Activity of Soluble and CLEC Urease

The enzymatic activity of soluble and CLEC urease was assayed spectrophotometrically (Table 20 and FIG. 13) by hydrolysis of the substrate urea at room temperature (Table 20 and FIG. 1). Initial substrate concentration was 0.39 $\mu$g/ml ($6.5 \times 10^{-8}$M) as determined by Bradford protein determination. The reaction volume was 5 ml. Urea hydrolysis was quantified calorimetrically using the Sigma diagnostics blood urea nitrogen kit (procedure No. 535) according to the manufacturer's instructions. Absorbance was fitted to a first order rate equation and kcat/Km was calculated by dividing the fitted value by enzyme concentration as described in Example 2.

TABLE 21

Urease pH curve

| | | % Maximum Activity | |
|---|---|---|---|
| | pH | CLEC urease | Soluble urease |
| 1 | 5 | 0 | 0 |
| 2 | 6 | 62 | 51 |
| 3 | 7 | 100 | 100 |
| 4 | 8 | 97 | 91 |
| 5 | 9 | 74 | 69 | pH Dependence and Stability

Figure 14:
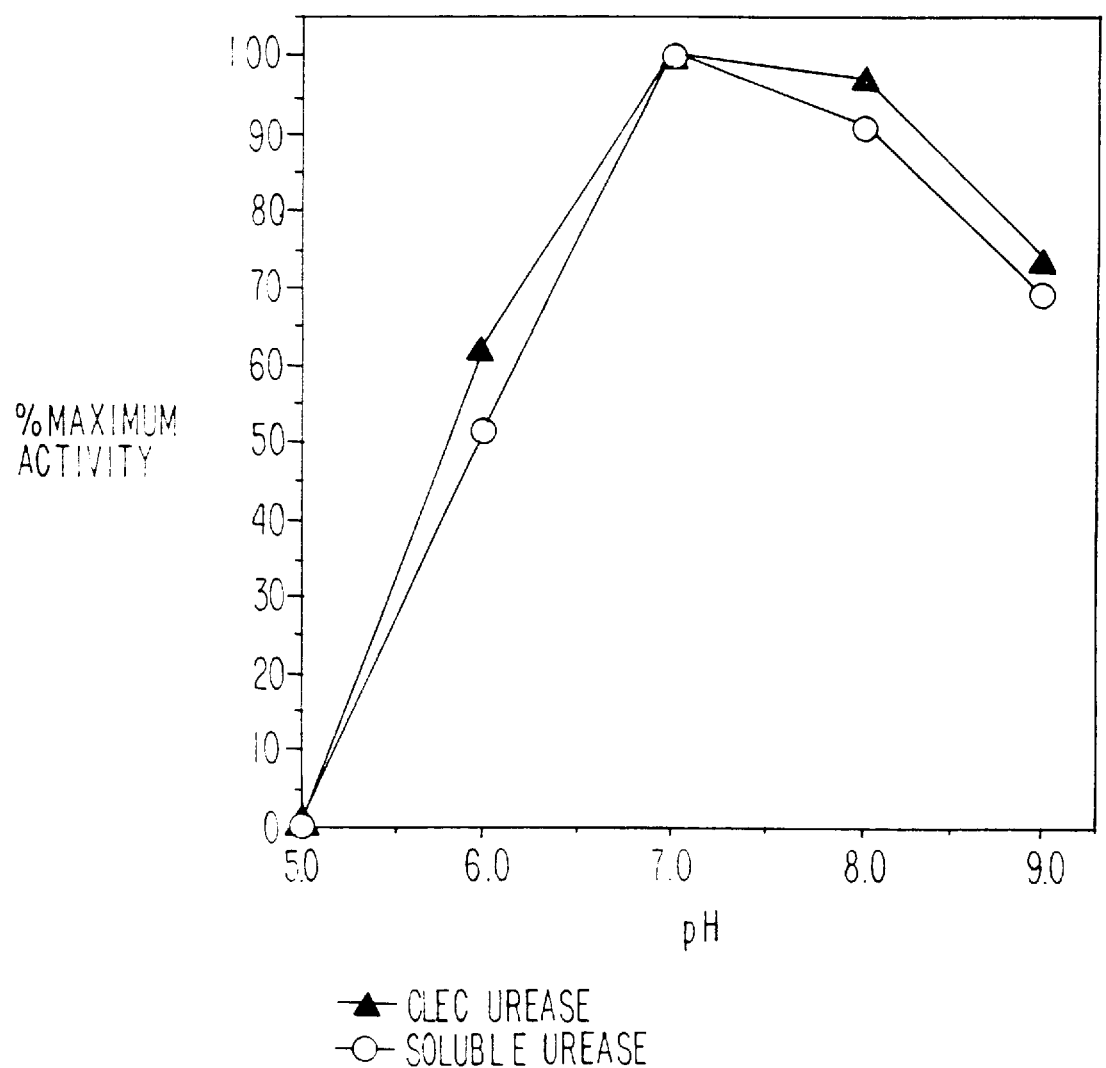
FIG. 14 is a graphic representation of results of assessment of pH dependence and stability of soluble urease and the corresponding urease CLEC.
Figure 15:
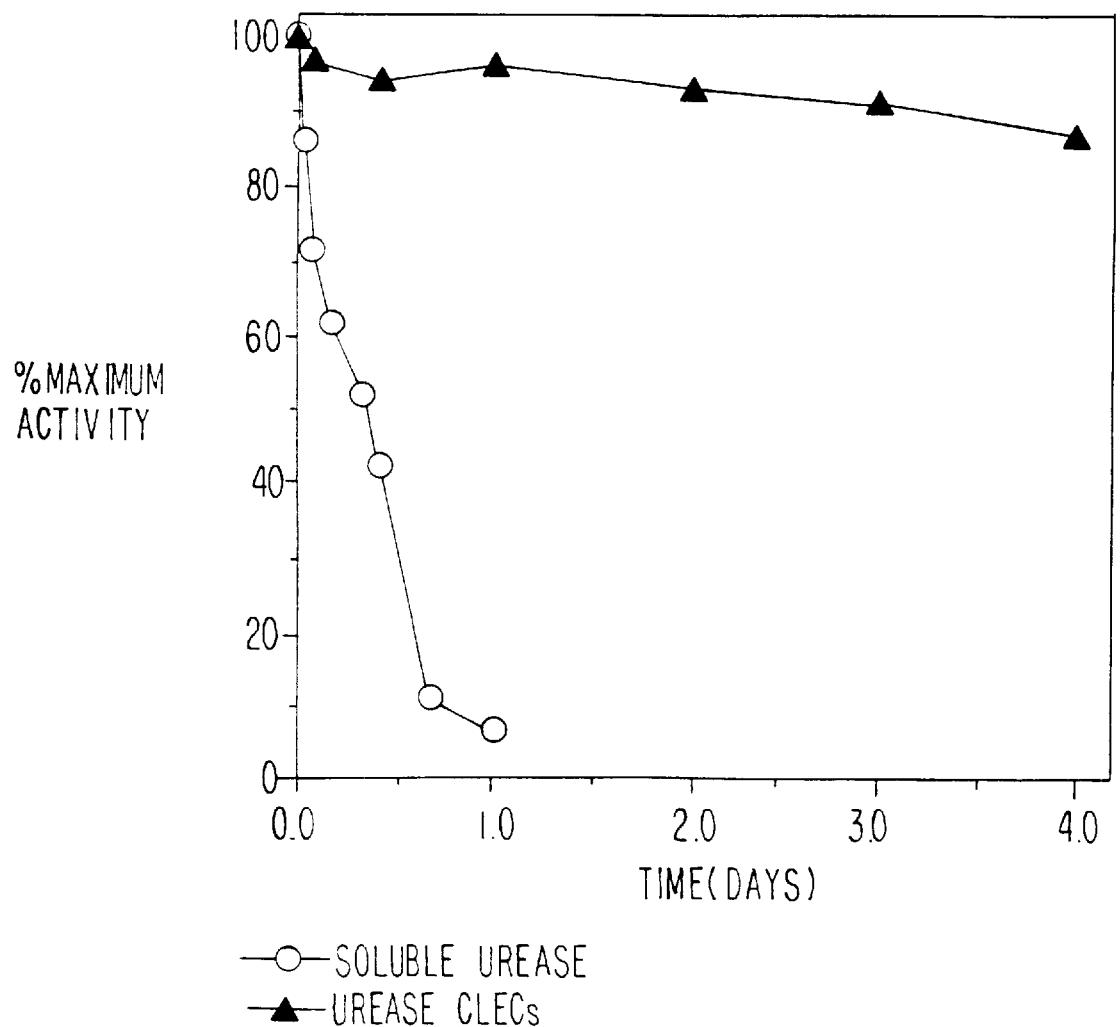
FIG. 15 is a graphic representation of results of assessment of thermal stability of soluble urease and the corresponding urease CLEC.
Figure 16:
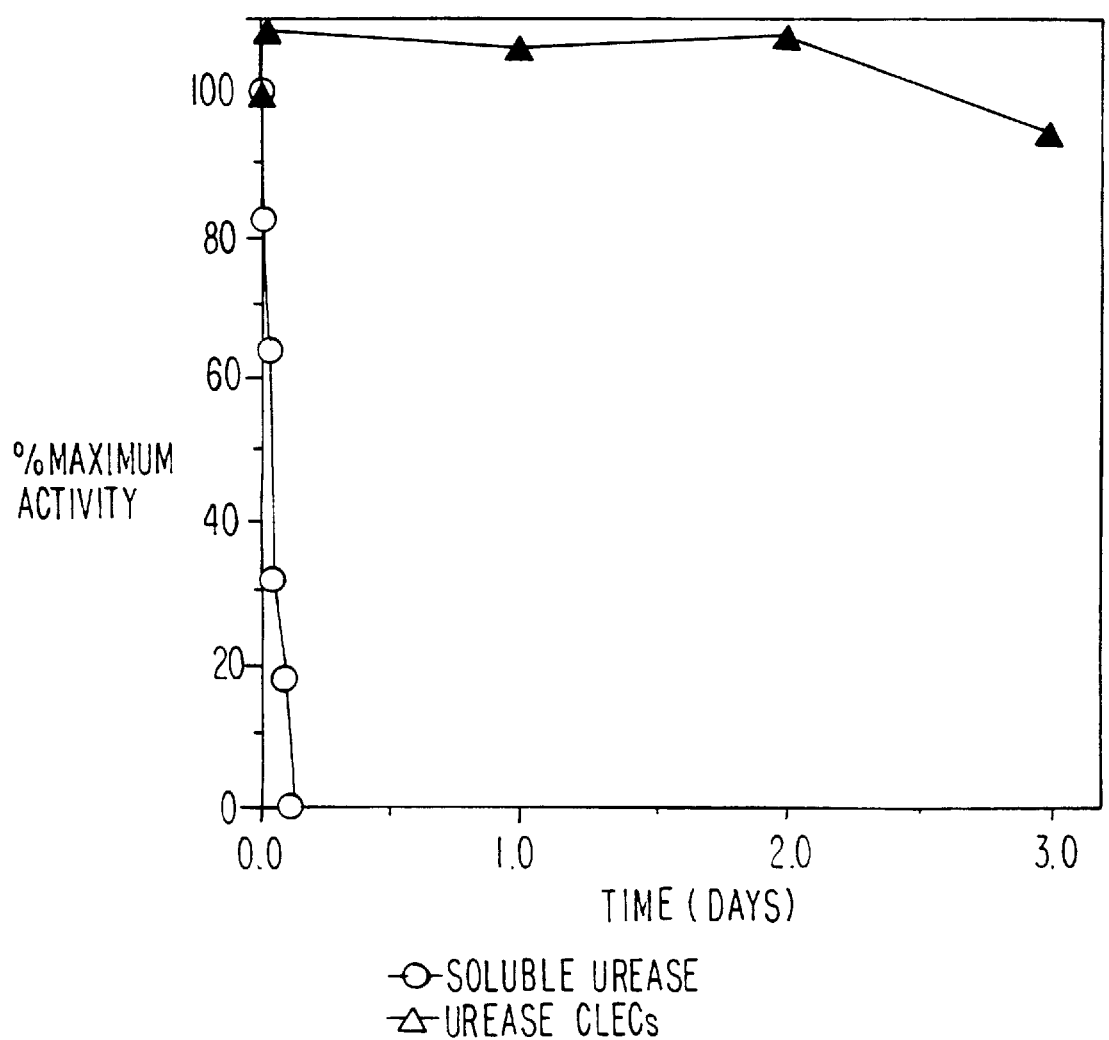
FIG. 16 is a graphic representation of results of assessment of resistance to exogenous proteolysis of soluble urease and the corresponding urease CLEC.

The pH optimum and stability of the soluble urease were compared to that of urease CLECs by cleavage of urea at the indicated pH (Table 21 and FIG. 14). Both CLEC and soluble urease show a similar pH profile, having optimum activity at pH 7.

TABLE 22

Urease thermal stability

| | | % Maximum Activity | |
|---|---|---|---|
| | Time (days) | CLEC urease | Soluble urease |
| 1 | 0.000 | 100 | 100.0 |
| 2 | 0.042 | | 86.0 |
| 3 | 0.083 | 97 | 71.5 |
| 4 | 0.166 | | 61.5 |
| 5 | 0.330 | | 52.0 |
| 6 | 0.416 | 94 | 42.0 |
| 7 | 0.666 | | 10.5 |
| 8 | 1.000 | 96 | 6.5 |
| 9 | 2.000 | 93 | |
| 10 | 3.000 | 91 | |
| 11 | 4.000 | 87 | |

Thermal Stability at 55° C.

The activity of soluble and CLEC urease was measured following incubation at 55° C. Soluble and CLEC urease were incubated with stirring in 50 mM sodium phosphate buffer pH 7.0 at 55° C. The reaction volume was one milliliter. Final protein concentration was 10 mg/ml. Aliquots of soluble urease were removed at times 0, 1, 2, 4, 8, 10, 16 and 24 hours. Aliquots of CLEC urease were removed at times 0, 2, 10, 24, 48, 72 and 96 hours. Enzymatic activity was assayed at room temperature as described above (Table 22 and FIG. 15).

TABLE 23

Urease protease resistance

| | | % Maximum Activity | |
|---|---|---|---|
| | Time (days) | CLEC urease | Soluble urease |
| 1 | 0.000 | 100 | 100 |
| 2 | 0.014 | | 74 |
| 3 | 0.028 | 108 | 54 |
| 4 | 0.042 | | 29 |
| 5 | 0.083 | | 13 |
| 6 | 0.104 | | 3 |
| 7 | 0.125 | | 0 |
| 8 | 1.000 | 106 | |
| 9 | 2.000 | 107 | |
| 10 | 3.000 | 94 | |

Resistance to Exogenous Proteolysis

Assessment of the resistance of the urease CLEC to the action of protease was also performed under identical conditions (excepting the substitution of 50 mM sodium phosphate pH 7.5 for 50 mM Tris pH 7.5 as the base buffer) as described for thermolysin (Example 2). Activity of the soluble and CLEC enzyme, following incubation with protease, was assayed as described above (Table 23 and FIG. 16).

TABLE 24

Urease stability in organic solvents

| | | % Maximum Activity | |
|---|---|---|---|
| | | CLEC urease | Soluble urease |
| 1 | Acetonitrile | 93 | 40 |
| 2 | Dioxane | 95 | 45 |
| 3 | Acetone | 90 | 61 |
| 4 | THF | 82 | 13 |

Stability in Organic Solvents

Urease CLECs and soluble urease were incubated for one hour at 40° C. in 50% (v/v) solutions of the indicated organic solvents (as described in Example 2) (Table 24). Following incubation, enzyme activity was assayed by measuring urea hydrolysis as described above.

TABLE 25

Urease CLEC catalytic activity in sera

| | | Absorbance 535 nm | |
|---|---|---|---|
| | Time (min) | Buffer | Sera |
| 1 | 0 | 1.066 | 1.059 |
| 2 | 3 | 0.769 | 0.714 |
| 3 | 5 | 0.672 | 0.644 |
| 4 | 10 | 0.537 | 0.489 |
| 5 | 20 | 0.206 | 0.225 |
| 6 | 30 | 0.146 | 0.140 |
| 7 | 45 | 0.030 | 0.025 |

Enzymatic Activity of Urease CLECs in Sera

The catalytic activity of urease CLECs in sera was compared to its activity in 50 mM Tris buffer pH 7.0. Urease CLECs were incubated in mouse sera for 16 hours at room temperature. Following incubation, urea was added to the sera to a concentration of 0.39 μg/ml. The rate of urea hydrolysis in sera was measured with a Sigma diagnostics blood urea nitrogen kit following the manufacturer's instructions. CLEC urease activity in 50 mM sodium phosphate pH 6.0 following 16 hours incubation in phosphate buffer at room temperature was used as a control. CLEC urease catalytic activity in sera, a biologically relevant medium, was comparable to activity in aqueous buffer (Table 25 and FIG. 17).

EXAMPLE 11

Crystallization and Crosslinking of *Candida cylindracea* Lipase and Assessment of Characteristics of the Resulting Product Crystallization of Lipase Lyophilized *Candida cylindracea* lipase (9.98 mg dry weight) (Boehringer Mannheim) was dissolved in 0.5 ml of deionized water. Final protein concentration was 6 mg/ml. To induce crystallization, the lipase was dialysed against a low salt buffer. Five buffer conditions produced crystals suitable for CLEC formulation: Condition 1, Dialysis against 5 mM sodium phosphate buffer pH 6; Condition 2, Dialysis against 5 mM sodium phosphate buffer pH 7; Condition 3, Dialysis against 5 mM sodium phosphate pH 8; Condition 4, Dialysis against 20 mM Tris HCl pH 6.8; Condition 5, Dialysis against 20 mM Tris HCl pH 6.8 containing 1 mM $CaCl_2$ and 1 mM $MgCl_2$. All dialysis conditions produced a showering of lipase crystals; thin square plates 0.1 mm–0.05 mm in size. Crystallization was completed in six hours. Crystals were recovered by centrifugation as previously described. Lipase crystals were washed ten times with 20 mM buffer pH 6.8. Following washing, crystals were again recovered by centrifugation.

Cross-linking of *Candida cylindracea* Lipase Crystals

As disclosed here, lipase crystals were cross-linked in a solution of 7.5% glutaraldehyde and 20 mM Tris HCl pH 6.8 for 30 minutes at room temperature. Following cross-linking the crystals were washed exhaustively with 20 mM Tris HCl pH 6.8.

Enzymatic Activity of CLEC Lipase

The catalytic activity of the lipase CLECs was assayed qualitatively by hydrolysis of the calorimetric substrate p-nitrophenyl acetate (Fluka) (M. Semeriva et al. *Biochem. Biophys. Res. Comm.* 58:808–813 (1974)). The presence of catalytic activity is indicated by the appearance of a yellow color in the assay solution. Several lipase CLECs were placed in a 100 μl solution of 3.12 mM p-nitrophenyl acetate containing 4% acetonitrile in 80 mM Tris HCl pH 7.5 at room temperature. To monitor spontaneous hydrolysis of the substrate, a negative control containing assay mix and buffer was prepared simultaneously. Soluble lipase was used as a positive control. Lipase CLECs were found to retain significant activity.

EXAMPLE 11

Porcine Pancreatic Lipase Purification

The purification was based in large part on the published procedure of Roberts et al., *Lipids* 20:42–45 (1985). The following are the differences between the purification procedure used herein and the published protocol.

1. The initial extraction buffer, "buffer A" in the publication, does not contain sodium azide.
2. The procedure was followed exactly as published up through the butanol extraction and then the following additional steps were taken.
    A. The "creamy interface" resultant from the butanol extraction was resuspended in 150 ml publication "buffer B".
    B. The butanol extraction was repeated as described in the publication.
    Two butanol extractions were performed instead of one.
3. The published procedure was followed up through the overnight dialysis and centrifugation. No column chromatography was run.
4. This procedure is run at 4× the published scale.
5. The final product is frozen at −20° C.

Original Crystallization

1. The frozen lipase was thawed and dialyzed vs. 5 mM cacodylate pH 7.0, 3.3 mM $CaCl_2$. Dialysate was centrifuged at 5000×G for 5 minutes. Supernatant was sequentially concentrated and diluted with 5 mM cacodylate pH 7.0 until the following conditions were reached:
    Protein concentration=97 mg/ml
    CaCl2 concentration=0.2 mM
    Na taurodeoxycholate concentration=0.5 mM
2. Vapor diffusion.
    Reservoir: 1.0 ml 10% (v/v) PEG 400 in $H_2O$
    Drop: 5 μl protein from step # 1+5 μl reservoir
    A large number of rods were observed overnight under these conditions.

Batch Crystallization

1. Purified lipase was allowed to sit undisturbed in the cold room under the following conditions:
    Protein concentration=46 mg/ml
    Buffer=5 mM cacodylate pH 7.0, 0.02 mm $CaCl_2$, 0.5 mM Na taurodeoxycholate
    Lipase sat from Dec. 6, 1991 to Jan. 7, 1992, when a large number of rod shaped crystals were observed.
2. These crystals were washed in 20% (v/v) PEG 400 and crushed. The following seeding was performed:
    100 μl purified lipase in 5 mM cacodylate, pH7.0 concentration=77 mg/ml
    5 μl PEG 400
    5 μl seeds
    The lipase rods were observed to "crash out" almost instantly at room temperature.

Cross-linking (Original Conditions)

Wash crystals in 30% PEG 400, 5 mM cacodylate, pH 7.0
Crosslink at room temperature in 3.3% glutaraldehyde for 1.5 hour
Wash in 20 mM Tris pH 8.0.

EXAMPLE 12

We have observed that crystal nucleation and growth will occur on a variety of forms and material surfaces. The following study was performed with the protease thermolysis.

Stainless steel forceps, glass beads, string and chromatography matrix, were each immersed in a crystallization solution of thermolysis protein prepared as described in U.S. patent application Ser. No. 07/720,237 as filed on Jun. 4, 1991 and allowed to incubate overnight at room temperature. Incubation resulted in the attachment of a coating of thermolysis crystals on all surfaces in contact with the protein solution.

The use of attached lyophilized (dried) or unlyophilized, crosslinked or uncrosslinked crystalline material as described in U.S. patent application Ser. No. 07/720,237, should significantly benefit the use of proteins and related compounds in industry and science, by permitting the coating of a variety of materials with any crystalline material of interest. Crystallization occurs at a density approaching theoretical packing limits for a given molecule. This phenomena may be of import in any application which requires a high density of protein per unit volume, such as bioelectronics, materials science and biosensors. Moreover, crystal deposition may be directed and controlled by a number of means including pretreatment or charging of the crystallization surface; limiting the rate and extent of crystallization and defining individual crystal size. A given crystal or crystalline surface could also be used as a site of attachment for a different crystalline material. For example, two enzymes, one of which generates a cofactor or substrate for a different enzyme, could both be effectively co-crystallized in the same functional space. Finally, isolated or clustered crystals or a crystalline layer or layers of the same or different crystalline material could be deposited on, between, or within various surfaces or layers to facilitate application in many fields of science and technology.

EXAMPLE 13

We have discovered that crosslinked enzyme crystals (CLECs), as described in U.S. patent application Ser. No. 07/720,237 as filed on June 4, 1991 are biocompatible and exhibit enzyme activity in vivo. The following experiments were performed with thermolysin and asparaginase CLECs prepared as described in U.S. patent application Ser. No. 07/720,237.

Five milligrams of enzymatically active thermolysin CLECs, and five milligrams of thermolysin CLECs inactivated by extensive chemical crosslinking were injected intraperitonealy into mice. The animal receiving active CLECs died within two hours. The animal receiving the inactivated CLECs survived several weeks until autopsy, with no observable effects.

In a preliminary experiment, asparaginase CLECs in doses of 1 to 200 IU were injected intraperitonealy into control and lymphoma induced mice. There was no difference in survival time between aparaginase treated and control (untreated) lymphoma induced mice. Asparaginase CLECs did not demonstrate any toxic effects.

There is significant potential to employ enzymes as therapeutics: for example, to remove toxins, drugs and metabolites in the treatment of several conditions, including acute lymphoid leukemias and inborn errors of metabolism. Immunogenicity and short half-life currently limit the use of proteins, peptides and related molecules as therapeutics. Crystalline uncrosslinked or crosslinked, proteins and peptides resist inactivation by proteolysis and acids, and are likely to be nonimmunogenic. CLECs also demonstrate chromatographic properties making them suitable for use in extracorporeal devices for treatment of diseases such as chronic renal failure. In addition, CLECs are insoluble, making the use of entrapment and implantation of the CLECs attractive. The size of the crystal can also be tightly controlled, making oral and injectable therapeutic delivery routes feasible.

EXAMPLE 14

We have discovered that crosslinked enzyme crystals (CLECs) as described in U.S. patent application Ser. No. 07/720,237 as filed on Jun. 4, 1991 demonstrate chromatographic properties. The following procedure was performed with CLECs of the protease thermolysin:

A 15 microliter volume of thermolysin CLECs prepared as described in U.S. patent application Ser. No. 07/720, 237 was placed in a small column forming a bed volume of 2 mm×200 mm. One hundred milliliters of water were passed through the column at a flow rate of 25 ml per hour. Protein assay of the flow through indicated that no protein was present. Twenty milliliters of a thermolysin spectrophotometric substrate as described in U.S. patent application Ser. No. 07/720, 237 was then passed through the column at a flow rate of 25 ml per hour. Spectrophotometric analysis of the flow through indicated that complete hydrolysis of the substrate had occurred. Further, the CLEC enzyme column bed showed no change in flow rate following a through put of greater than 700 bed volumes.

This is a novel observation to the best of our knowledge, and should significantly benefit the use of enzymes and proteins in industry and science by, among other things facilitating the use of CLEC proteins in applications where chromatographic properties are advantageous.

EXAMPLE 15

We have observed that crystal growth and hence size can be controlled by a number of different methods. We have demonstrated this on both the milligram and tens of gram scale. The following protocol was performed with the protease thermolysin.

Purified thermolysin crystals, 90% thermolysin enzyme protein by weight, were solubilized in a crystallization solution of 30% DMSO and 0.25M calcium acetate pH 6.5. Thermolysin crystallization was induced by reducing the DMSO concentration of the crystallization solution as described in U.S. patent application Ser. No. 07/720,237 as filed on Jun. 4, 1991. Crystal nucleation, growth and size were reproducibly controlled through manipulation of the crystallization solution protein concentration and magnitude of DMSO dilution. Two micron crystals were prepared by the dilution of a 100 mg/ml thermolysin solution with 5 volumes of calcium buffer where as 100 micron crystals were obtained by dilution of a 50 mg/ml solution with 3 volumes of buffer. Agitation, temperature, the addition of seed crystals, and combinations of these and other crystallization parameters may be used to reproducibly control crystal size.

These observations should significantly benefit the use of enzymes, proteins, and peptides in science industry and medicine. For example crosslinked enzyme crystals (CLECs), as described in U.S. patent application Ser. No. 07/720,237, could be designed for specific industrial applications to optimize catalytic efficiency and ease of recovery. Protein crystal applications in the fields of biosensors, bioelectronics and materials science may also derive benefit from crystals of defined dimensions. Therapeutic applications may also require a specific crystal size, for example crystals of less than ten microns may permit injection and oral delivery of crosslinked or uncrosslinked proteins, peptides and related molecules.

EXAMPLE 16

We have observed that protein crystals are stable and catalytically active for extended periods of time in buffered organic solvents, and aqueous solutions having sufficient osmolarity and buffering capacity to stabilize the crystalline structure. Further, altering the environment of the stabilized crystal by, for example, pH change, temperature change or osmotic pressure change, will induce the solubilization of the crystal to active soluble protein molecules. The following experiments were performed with the protease subtilisin carlsberg and *Candida cylindreacea* lipase.

A preparation of crystalline subtilisin carlsberg remained catalytically active and in crystal form at room temperature in a nonsterile aqueous solution of 17% sodium sulfate at pH 5.9 for 30 days. The crystals were then solubilized to active monomers by shifting the osmolarity of the crystal environment from 17% sodium sulfate <0.5% sodium sulfate pH 5.9 or to 10 mM sodium phosphate pH 5.9. Alternatively the crystals were solubilized by maintaining the osmotic environment and shifting the pH from acidic (pH 5.9) to basic (9.0) conditions. The rate of solubilization could be controlled by varying protein concentration and/or the magnitude of change in one or more parameters of the crystal environment. Spectrophotometric activity assay of the solubilized crystals showed that the formerly crystalline enzyme had activity comparable to that observed for a fresh preparation of soluble enzyme.

*Candida cylindracea* lipase crystals were used to catalyze the esterification of an alcohol in a buffered organic solvent. The enzyme crystals maintained their structural integrity during the 72 hour reaction. Approximately 10,000 units of candida lipse crystals were dried with phosphate buffered ethano pH 7.0. The lipase crystals were then added to a 2 ml reaction containing 130 mM dl menthol and 100 mM 5-phenylvaleric acid in phosphate buffer saturated isooctane pH 7.0. The reaction was incubated at 30° C. with shaking at 150 rpm for 72 hours. Thin layer chromatography of the reaction mix demonstrated the presence of the esterification product, menthol phenyl valerate.

The application of these observations should greatly benefit the use of enzymes in industry, science and medicine, by permitting the stabilization of enzymes, proteins, peptides and related molecules, in crystal form, followed by the controlled dissociation of the crystal lattice releasing the active free molecule.

Equivalents

Those skilled in the art will recognize or be able to ascertain, using no more than routine experimentation, many equivalents to the specific materials and components described herein. Such equivalents are intended to be encompassed in the scope of the following claims.

We claim:

1. A protein crystal crosslinked with a multifunctional crosslinking agent, said crosslinked protein crystal having resistance to exogenous proteolysis, such that said crosslinked protein crystal retains at least 91% of its stability, as measured in terms of degradation, after incubation for three hours in the presence of a concentration of Pronase™ that causes the soluble uncrosslinked form of the protein that is crystallized to form said protein crystal that is crosslinked to lose at least 94% of its stability, as measured in terms of degradation, under the same conditions.

2. The crosslinked protein crystal according to claim 1, wherein said crystal is a microcrystal.

3. The crosslinked protein microcrystal according to claim 2, wherein said microcrystal has a cross-section of $10^{-1}$ or less.

4. The crosslinked protein crystal according to claim 1 or 2, wherein said protein is a therapeutic protein.

5. The crosslinked protein crystal according to claim 1 or 2, wherein said protein crystal is in lyophilized form.

6. The crosslinked protein crystal according to claim 1 or 2, wherein said protein is an antibody.

7. The crosslinked antibody crystal according to claim 6, wherein said antibody is a therapeutic antibody.

8. The crosslinked antibody crystal according to claim 6, wherein said antibody is an antibody that binds to a protein.

9. The crosslinked antibody crystal according to claim 6, wherein said antibody is an antibody that binds to a virus or an antibody that binds to a bacteria.

10. An enzyme crystal crosslinked with a multifunctional crosslinking agent, said crosslinked enzyme crystal having resistance to exogenous proteolysis, such that said crosslinked enzyme crystal retains at least 91% of its initial activity after incubation for three hours in the presence of a concentration of Pronase™ that causes the soluble uncrosslinked form of the enzyme that is crystallized to form said enzyme crystal that is crosslinked to lose at least 94% of its initial activity under the same conditions, wherein said crystal is in lyophilized form.

11. A lipase crystal crosslinked with a multifunctional crosslinking agent, said crosslinked lipase crystal having resistance to exogenous proteolysis, such that said crosslinked lipase crystal retains at least 91% of its initial activity after incubation for three hours in the presence of a concentration of Pronase™ that causes the soluble uncrosslinked form of the lipase that is crystallized to form said lipase crystal that is crosslinked to lose at least 94% of its initial activity under the same conditions, wherein said lipase is selected from the group consisting of *Geotrichum candidum* lipase, *Candida cylindracea* lipase and porcine lipase.

12. An enzyme-catalyzed method of producing a selected product, comprising the steps of:

(a) combining at least one substrate and at least one enzyme which acts upon the substrate, said enzyme being an enzyme crystal crosslinked with a multifunctional crosslinking agent, said crosslinked enzyme crystal having resistance to exogenous proteolysis, such that said crosslinked enzyme crystal retains at least 91% of its initial activity after incubation for three hours in the presence of a concentration of Pronase™ that causes the soluble uncrosslinked form of the enzyme that is crystallized to form said enzyme crystal that is crosslinked to lose at least 94% of its initial activity under the same conditions; and (b) maintaining the combination produced in step (a) under conditions which permit said enzyme to act upon the substrate, thereby producing the selected product.

13. The method according to claim 12, wherein said product is selected from the group consisting of peptides, carbohydrates and lipids.

14. The method according to claim 12, wherein the conditions in step (b) include a pH between about 5 and about 10.

15. The method according to claim 12, wherein said substrate is an organic polymer.

* * * * *